US008067406B2

(12) United States Patent
Kimura et al.

(10) Patent No.: US 8,067,406 B2
(45) Date of Patent: Nov. 29, 2011

(54) PREVENTIVE/REMEDY FOR RETINAL NERVE DISEASES CONTAINING ALKYL ETHER DERIVATIVES OR SALTS THEREOF

(75) Inventors: Tatsuo Kimura, Toyama (JP); Noboru Iwakami, Takaoka (JP); Akihito Saitoh, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/008,982

(22) Filed: Jan. 19, 2011

(65) Prior Publication Data
US 2011/0112066 A1 May 12, 2011

Related U.S. Application Data

(60) Division of application No. 12/542,074, filed on Aug. 17, 2009, now Pat. No. 7,897,594, which is a continuation of application No. 10/553,120, filed as application No. PCT/JP2004/005355 on Apr. 15, 2004, now abandoned.

(30) Foreign Application Priority Data

Apr. 17, 2003 (JP) ................................. 2003-112539

(51) Int. Cl.
*A61K 31/00* (2006.01)
(52) U.S. Cl. ................................... 514/210.19; 514/912
(58) Field of Classification Search ............. 514/210.19, 514/912
See application file for complete search history.

(56) References Cited

U.S. PATENT DOCUMENTS

| 7,087,594 B2 | 8/2006 | Saitoh et al. |
| 7,342,043 B2 | 3/2008 | Nakada et al. |

FOREIGN PATENT DOCUMENTS

| CA | 2141729 | 8/1995 |
| EP | 0 873 990 A1 | 10/1998 |
| EP | 1 325 744 A1 | 7/2003 |
| FR | 2 521 136 | 8/1983 |
| JP | 7-304717 | 11/1995 |
| JP | 8-506807 | 7/1996 |
| JP | 8-511783 | 12/1996 |
| JP | 11-263773 | 9/1999 |
| JP | 4398247 | 10/2009 |
| WO | 95/00486 | 1/1995 |
| WO | 97/11054 | 3/1997 |
| WO | 02/30420 | 4/2002 |
| WO | 02/100833 | 12/2002 |
| WO | 03/035647 | 5/2003 |

OTHER PUBLICATIONS

Mayo Clinic, Stargardt's disease: Can it be treated?, 2006, printed May 27, 2008, MayoClinic.com, http://www.mayoclinic.com/print/stargardts-disease/AN00846/METHOD=print, 2 pages.*
www.AMD.org, What Is AMD?, printed from http://www.amd.org/what-is-amd.html on Aug. 3, 2010, 2 pages.*
Masuzawa et al., A Model of Retinal Ischemia-Reperfusion Injury in Rats by Subconjunctival Injection of Endothelin-1, 2006,Experimental Biology and Medicine, 231:1085-1089.*
Rosenbaum et al., Functional and Morphologic Comparison of Two Methods to Produce Transient Retinal Ischemia in the Rat, Mar. 2001, Journal of Neuro-Ophthalmology, 21(1):62-68.*
Youn et al., Effects of 400 nm, 420 nm, and 435.8 nm radiations on cultured human retinal pigment epithelial cells, 2009, Journal of Photochemistry and Photobiology B: Biology, vol. 95, Issue 1, pp. 64-70.*
Anderson et al., Characterization of beta amyloid assemblies in drusen: the deposits associated with aging and age-related macular degeneration, Exp Eye Res. Feb. 2004;78(2), printed from http://www.ncbi.nlm.nih.gov/pubmed/14729357, Abstract only, 1 page.*
Deutman et al., Dominantly inherited drusen of Bruch's membrane, Br J Ophthalmol. Jun. 1970.; 54(6): 373-382.*
Rosenbaum, et al., Functional and Morphologic Comparison of Two Methods to Produce Transient Retinal Ischemia in the Rat, Journal of Neuro-Opthalmology, vol. 21, No. 1, pp. 62-68 (Mar. 2001).
Masuzawa, et al., A Model of Retinal Ischemia-Reperfusion Injury in Rats by Subconjunctival Injection of Endothelin-1, Experimental Biology and Medicine, vol. 231, pp. 1085-1089 (2006).
http//www.wrongdiagnosis.com, Prognosis of Age-related macular degeneration, http://www.wrongdiagnosis.com/a/age_related_macular_degeneration/prognosis.htm 3 pages (printed May 7, 2009).
Pang, et al., Acute effects of glaucoma medications on rat intraocular pressure, Experimental Eye Research, vol. 80, No. 2, pp. 207-214 (Feb. 2005).
Mayo Clinic staff, Diabetic retinopathy-Treatments and drugs, www.mayoclinic.com, printed from http://www.mayoclinic.com/health/diabetic-retinopathy/DS00447/DSECTION=treatments%2Dand%2Ddrugs, 4 pages (2008) (printed on May 7, 2009).
The Foundation Fighting Blindness, Animal Models for Studying, Inherited Degenerative Retinal Disease, The Foundation Fighting Blindness, printed from www.retina-international.org/sci-news/animmod.doc, 23 pages (2000) (printed on Jan. 11, 2009).

(Continued)

*Primary Examiner* — Zohreh A Fay
(74) *Attorney, Agent, or Firm* — Oblon, Spivak, McClelland, Maier & Neustadt, L.L.P.

(57) ABSTRACT

An alkyl ether derivative represented by the following general formula [1]

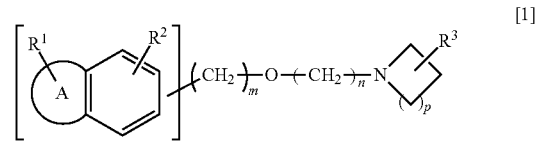

or its salt: wherein $R^1$ and $R^2$ represent each a substituent such as hydrogen, halogeno or alkyl; $R^3$ represents alkylamino, amino or hydroxyl; the ring A represents a 5- or 6-membered aromatic heterocycle or a benzene ring; m and n are each an integer of from 1 to 6; and p is an integer of from 1 to 3; shows an effect of protecting retinal nerve cells and, therefore, is useful as a preventive and/or a remedy for retinal nerve diseases such as glaucoma, diabetic retinopathy, retinal artery obstruction, retinal venous obstruction, macular degeneration and retinopathy of prematurity.

2 Claims, No Drawings

OTHER PUBLICATIONS

Mayo Clinic Stargardt's disease: Can it be treated?, http://www.mayoclinic.com/print/stargardts-desease/AN00846/METHOD=print, 2 pages (2006).

National Eye Institute, Retinopathy of Prematurity (ROP), http://www.nei.nih.gov/helath/rop/, 6 pages (2008)(printed on May 7, 2009).

Zhang, et al., Activation of the Mitochondrial Apoptotic Pathyway in a Rat Model of Central Retinal Artery Occlusion, Investigative Opthalmology and Visual Science, vol. 46, pp. 2133-2139 (2005).

Newman, Hereditary Optic Neuropathies: From the Mitochondria to the Optic Nerve, American Journal of Opthalmology, vol. 140, pp. 517-523 (Sep. 2005).

Schmidt-Erfurth, et al., Management of neovascular age-related macular degeneration, Progress in Retinal and Eye Research, vol. 26, pp. 437-451 (2007).

Merck Manual Online Medical Library, Age-Related Macular Degeneration, Merck Manual-printed from http://www.merck.com/mmpe/print/sec09/ch106/ch106b.html, 2 pages (2005) (printed on Oct. 20, 2008).

Moalem, et al., Differential T cell response in central and peripheral nerve injury: connection with immune privilege, The FASEB Journal, vol. 13, pp. 1207-1217 (1999).

Stedman's Medical Dictionary $27^{th}$ Edition, remedy, printed from http://www.thomsonhc.com/pdrel/librarian/PFDefaultActionId/pdrcommon.Stedmans, 1 page (2000) (printed on Oct. 20, 2008).

Merck Manual Online Medical Library, Diabetic Retinopathy, Merck Manual-printed from http://www.merck.com/mmpe/print/sec09/ch106/ch106e.html, 2 pages (2005) (printed on Oct. 20, 2008).

Hyojun Ganka Gaku, $7^{th}$ Edition, pp. 103-107, Igaku-Shoin Ltd. (1998).

Haruki, Abe: Atarashii Ganka, vol. 19, No. 7, pp. 903-912 (2002) (with English abstract).

"Agouron buys drug discovery company" "Chiroscience slaps up licensing talks", SCRIP, No. 2229, p. 13 (May 6/9, 1997).

"Allergan's1997 sales fall", SCRIP, No. 2307, p. 10 (Feb. 8, 1998).

MedlinePlus, Retinal artery occlusion, Apr. 22, 2008, U.S. National Library of Medicine and National Institutes of Health, printed from http://www.nlm.nih.gov/medlineplus/ency/article/001028.htm on Apr. 7, 2010,3 pages.

MayoClinic.com, Dry macular degeneration, Aug. 26, 2008, MayoClinic.com, printed from http://www.mayoclinic.com/health/macular-dengeneration/DS00284/METHOD=print &DSECTION=all on Apr. 7, 2010, 13 pages.

Merck Manuals, Hereditary Optic Neuropathies, 2005, http://www.merck.com/mmpe/print/sec09/ch107/ch107b.html printed May 27, 2008, 2 pages.

Merck Manuals, Retinitis Pigmentosa, 2005, http.//www.merck.com/mmpe/print/sec09/ch106/ch106h.html printed May 27, 2008, 2 pages.

Youn, et al, Effects of 400 nm, 420 nm, and 435.8 nm radiations on cultured human retinal pigment epithelial cells, Journal of Photochemistry and Photobiology B: Biology, vol. 95, Issue 1, pp. 64-70 (2009).

U.S. Appl. No. 12/985,616, filed Jan. 6, 2011, Saitoh, et al.

* cited by examiner

PREVENTIVE/REMEDY FOR RETINAL NERVE DISEASES CONTAINING ALKYL ETHER DERIVATIVES OR SALTS THEREOF

This is a divisional application of U.S. application Ser. No. 12/542,074, filed Aug. 17, 2009, which is a continuation application of U.S. application Ser. No. 10/553,120, filed Oct. 14, 2005, which is a 371 of PCT/JP04/05355 filed on Apr. 15, 2004.

TECHNICAL FIELD

The present invention relates to a preventive and/or remedy for retinal nerve diseases, which comprise a novel alkyl ether derivative or a salt thereof as an active ingredient.

BACKGROUND ART

The retina acting as a photoreceptive tissue is located at the inner surface of the wall of eyeball. When pathologic lesion occurs on the retina, eyesight fails, sometimes resulting in blindness. Such retina is broadly divided into sensory retina and retinal pigment epithelium. Such sensory retina is divided into 9 layers, and comprises visual cells as first neuron, bipolar cells as second neuron, ganglion cells as third neuron, and other cells (*Hyojun Ganka Gaku*, 7$^{th}$ edition, pp. 103-107, Igaku-Shoin Ltd., 1998).

Various retinal diseases are developed depending on the causes of diseases or onset forms. Examples of a disease affecting the retinal nerve may include glaucoma, diabetic retinopathy, retinal artery obstruction, retinal venous obstruction, macular degeneration, and retinopathy of prematurity.

It has been considered that the cell death of retinal nerve cells is deeply associated with dysfunction of the retinal nerve. Factors, which contribute the cell death of retinal nerve cells, may include apoptosis, neurotoxicity caused by glutamic acid, the absence of a neurotrophic factor, the abnormality of mitochondria, caspase activation, nitric oxide, and autoimmunity (*Atarashii Ganka*, 19(7), 903-912, 2002). For example, from the viewpoint of suppression of the cell death with an excitatory neurotransmitter such as glutamic acid, compounds having antagonistic action to N-methyl-D-aspartic acid have been studied (JP-A-8-506807; Scrip No. 2229, p. 13, 1997; Scrip No. 2307, p. 10, 1998).

As stated above, various factors are associated with the cell death of retinal nerve cells. Other than compounds having antagonistic action to N-methyl-D-aspartic acid, compounds useful as remedies for diseases such as glaucoma, diabetic retinopathy, retinal artery obstruction, retinal venous obstruction, macular degeneration, and retinopathy of prematurity, are required.

DISCLOSURE OF THE INVENTION

The present inventors have found that an alkyl ether derivative represented by the general formula [1] described below or a salt thereof shows the effect of protecting retinal nerve cells, and thus that it is useful as a preventive and/or remedy for retinal nerve diseases, thereby completing the present invention.

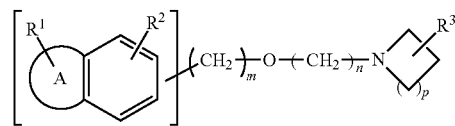

In the formula, R$^1$ and R$^2$, which may be the same or different, each represent one or more groups selected from a hydrogen atom, a halogen atom, a substituted or unsubstituted alkyl, aryl, aralkyl, alkoxy, aryloxy, alkylthio, arylthio, alkenyl, alkenyloxy, amino, alkylsulfonyl, arylsulfonyl, carbamoyl or heterocyclic group, a protected or unprotected amino, hydroxyl or carboxyl group, a nitro group and an oxo group; R$^3$ represents a substituted or unsubstituted alkylamino group or a protected or unprotected amino or hydroxyl group; the ring A represents a 5- or 6-membered aromatic heterocyclic ring or a benzene ring; m and n each represent an integer between 1 and 6; and p represents an integer between 1 and 3.

BEST MODE FOR CARRYING OUT THE INVENTION

The present invention will be described in detail below.
In the present specification, the terms have the following means, unless otherwise specified.

The term "halogen atom" is used to mean a fluorine atom, a chlorine atom, a bromine atom, or an iodine atom; the term "alkyl group" is used to mean a linear or branched C$_{1-12}$ alkyl group such as a methyl, ethyl, propyl, isopropyl, butyl, isobutyl, tert-butyl, pentyl, hexyl, heptyl, or octyl group; the term "lower alkyl group" is used to mean a linear or branched C$_{1-6}$ alkyl group such as a methyl, ethyl, propyl, isopropyl, butyl, isobutyl, tert-butyl, pentyl, or hexyl group; the term "alkenyl group" is used to mean a C$_{2-12}$ alkenyl group such as a vinyl, propenyl, butenyl, pentenyl, hexenyl, heptenyl, or octenyl group; the term "lower alkenyl group" is used to mean a C$_{2-6}$ alkenyl group such as a vinyl, propenyl, butenyl, pentenyl, or hexenyl group; the term "alkynyl group" is used to mean a C$_{2-6}$ alkynyl group such as an ethynyl, 2-propynyl, or 2-butynyl group; the term "cycloalkyl group" is used to mean a cyclopropyl, cyclobutyl, cyclopentyl, or cyclohexyl group; the term "alkoxy group" is used to mean a linear or branched C$_{1-12}$ alkyloxy group such as a methoxy, ethoxy, propoxy, isopropoxy, butoxy, isobutoxy, tert-butoxy, pentyloxy, hexyloxy, heptyloxy, or octyloxy group; the term "lower alkoxy group" is used to mean a linear or branched C$_{1-6}$ alkyloxy group such as a methoxy, ethoxy, propoxy, isopropoxy, butoxy, isobutoxy, tert-butoxy, pentyloxy, or hexyloxy group; the term "alkenyloxy group" is used to mean a C$_{2-12}$ alkenyloxy group such as a vinyloxy, propenyloxy, butenyloxy, pentenyloxy, hexenyloxy, heptenyloxy, or octenyloxy group; the term "lower alkenyloxy group" is used to mean a C$_{2-6}$ alkenyloxy group such as a vinyloxy, propenyloxy, butenyloxy, pentenyloxy, or hexenyloxy group; the term "alkylthio group" is used to mean a C$_{1-12}$ alkylthio group such as a methylthio, ethylthio, propylthio, isopropylthio, butylthio, isobutylthio, tert-butylthio, pentylthio, hexylthio, heptylthio, or octylthio group; the term "lower alkylthio group" is used to mean a C$_{1-6}$ alkylthio group such as a methylthio, ethylthio, propylthio, isopropylthio, butylthio, isobutylthio, tert-butylthio, pentylthio, or hexylthio group; the term "aryl group" is used to mean a phenyl group, naphthyl group, indanyl group, or indenyl group; the term "aryloxy group" is used to mean a phenyloxy, naphthyloxy, indanyloxy, or indenyloxy group; the term "aralkyl group" is used to mean an ar $C_{1-6}$ alkyl group such as a benzyl, diphenylmethyl, trityl, or phenethyl group; the term "arylthio group" is used to mean a phenylthio, naphthylthio, indanylthio, or indenylthio group; the term "acyl group" is used to mean a formyl group, a $C_{2-12}$ alkanoyl group such as acetyl, isovaleryl, propionyl, or pivaloyl, an aralkylcarbonyl group such as benzylcarbonyl, or an aroyl group such as benzoyl or naphthoyl; the term "alkylsulfonyl group" is used to mean a $C_{1-12}$ alkylsulfonyl group such as methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, hexylsulfonyl, heptylsulfonyl, or octylsulfonyl; the term "lower alkylsulfonyl group" is used to mean a $C_{1-6}$ alkylsulfonyl group such as methylsulfonyl, ethylsulfonyl, propylsulfonyl, isopropylsulfonyl, butylsulfonyl, isobutylsulfonyl, sec-butylsulfonyl, tert-butylsulfonyl, or pentylsulfonyl; the term "arylsulfonyl group" is used to mean a phenylsulfonyl, p-toluenesulfonyl, or naphthylsulfonyl group; the term "lower alkylsulfonyloxy group" is used to mean a $C_{1-6}$ alkylsulfonyloxy group such as methylsulfonyloxy, ethylsulfonyloxy, propylsulfonyloxy, isopropylsulfonyloxy, butylsulfonyloxy, isobutylsulfonyloxy, sec-butylsulfonyloxy, tert-butylsulfonyloxy, or pentylsulfonyloxy; the term "arylsulfonyloxy group" is used to mean a phenylsulfonyloxy, p-toluenesulfonyloxy, or naphthylsulfonyloxy group; the term "alkylamino group" is used to mean a mono- or di-$C_{1-6}$ alkylamino group such as methylamino, ethylamino, propylamino, isopropylamino, butylamino, dimethylamino, diethylamino, diisopropylamino, or dibutylamino; the term "monoalkylamino group" is used to mean a mono-$C_{1-6}$ alkylamino group such as methylamino, ethylamino, propylamino, isopropylamino, or butylamino; the term "dialkylamino group" is used to mean a di-$C_{1-6}$ alkylamino group such as dimethylamino, diethylamino, diisopropylamino, or dibutylamino; the term "heterocyclic group" is used to mean a heterocyclic group including a 5- or 6-membered ring, condensed ring, or crosslinked ring, containing at least one heteroatom selected from a nitrogen atom, an oxygen atom, and a sulfur atom, such as pyrrolidinyl, piperidinyl, piperazinyl, homopiperazinyl, homopiperidinyl, morpholinyl, thiomorpholinyl, tetrahydroquinolyl, quinuclidinyl, imidazolinyl, pyrrolyl, imidazolyl, pyrazolyl, pyridyl, pyrimidyl, quinolyl, quinolizinyl, thiazolyl, tetrazolyl, thiadiazolyl, pyrrolyl, pyrazolinyl, pyrazolidinyl, purinyl, furyl, thienyl, benzothienyl, pyranyl, isobenzofuranyl, oxazolyl, isoxazolyl, benzofuranyl, indolyl, benzimidazolyl, benzoxazolyl, benzisoxazolyl, benzothiazolyl, quinoxalyl, dihydroquinoxalyl, 2,3-dihydrobenzothienyl, 2,3-dihydrobenzopyrrolyl, 2, 3-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, oxadiazolyl, pyridazinyl, isoindolyl, isoquinolyl, 1,3-benzodioxanyl, or 1,4-benzodioxanyl group; and the term "cyclic amino group" is used to mean a cyclic amino group including a 5-, 6-, or 7-membered ring, condensed ring, or crosslinked ring, which contains at least one nitrogen atom as a heteroatom that forms the above ring, and may further contain at least one oxygen atom or sulfur atom, such as pyrrolidinyl, piperidinyl, piperazinyl, homopiperazinyl, homopiperidinyl, morpholinyl, thiomorpholinyl, tetrahydroquinolyl, tetrahydroisoquinolyl, or imidazolidinyl.

A 5- or 6-membered aromatic heterocyclic ring as the ring A may be a heterocyclic ring containing one or more heteroatoms selected from an oxygen atom, a nitrogen atom, and a sulfur atom as a heteroatom forming the above ring. Examples may include 5- or 6-membered aromatic heterocyclic rings such as triazine, pyridazine, pyrimidine, pyrazine, pyridine, furan, thiophene, pyrrole, oxazole, thiazole, imidazole, isoxazole, isothiazole, pyrazole, or pyran.

Substituents for an alkyl group, an aryl group, an aralkyl group, an alkoxy group, an aryloxy group, an alkylthio group, an arylthio group, an alkenyl group, an alkenyloxy group, an amino group, an alkylsulfonyl group, an arylsulfonyl group, a carbamoyl group, and a heterocyclic group in $R^1$ and $R^2$, and an alkylamino group in $R^3$, may include a halogen atom, a lower alkyl group, a cycloalkyl group, an aryl group, a lower alkoxy group, an aryloxy group, a lower alkylthio group, an arylthio group, a lower alkenyl group, a lower alkylsulfonyl group, an arylsulfonyl group, an alkylamino group, an amino group that may be protected, a hydroxyl group that may be protected, a carboxyl group that may be protected, an acyl group, and a heterocyclic group.

Protecting groups for a carboxyl group may include all groups that can be used as common protecting groups for a carboxyl group. Examples of such a protecting group may include: a lower alkyl group such as methyl, ethyl, propyl, isopropyl, 1,1-dimethylpropyl, butyl, or tert-butyl; an aryl group such as phenyl or naphthyl; an ar lower alkyl group such as benzyl, diphenylmethyl, trityl, 4-nitrobenzyl, 4-methoxybenzyl, or bis(4-methoxyphenyl)methyl; an acyl-lower alkyl group such as acetylmethyl, benzoylmethyl, 4-nitrobenzoylmethyl, 4-bromobenzoylmethyl, or 4-methanesulfonylbenzoylmethyl; an oxygen-containing heterocyclic group such as 2-tetrahydropyranyl or 2-teterahydrofuranyl; a halogeno-lower alkyl group such as 2,2,2-trichloroethyl; a lower alkylsilyl-lower alkyl group such as 2-(trimethylsilyl)ethyl; an acyloxy-lower alkyl group such as acetoxymethyl, propionyloxymethyl, or pivaloyloxymethyl; a nitrogen-containing heterocyclic ring-lower alkyl group such as phthalimidomethyl or succinimidomethyl; a cycloalkyl group such as cyclohexyl; a lower alkoxy-lower alkyl group such as methoxymethyl, methoxyethoxymethyl, or 2-(trimethylsilyl)ethoxymethyl; an ar-lower alkoxy-lower alkyl group such as benzyloxymethyl; a lower alkylthio-lower alkyl group such as methylthiomethyl or 2-methylthioethyl; an arylthio-lower alkyl group such as phenylthiomethyl; a lower alkenyl group such as 1,1-dimethyl-2-propenyl, 3-methyl-3-butenyl, or allyl; and a substituted silyl group such as trimethylsilyl, triethylsilyl, triisopropylsilyl, diethylisopropylsilyl, tert-butyldimethylsilyl, tert-butyldiphenylsilyl, diphenylmethylsilyl, or tert-butylmethoxyphenylsilyl.

Protecting groups for a hydroxyl group may include all groups that can be used as common protecting groups for a hydroxyl group. Examples of such a protecting group may include: alkoxy and alkylthio-carbonyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)

ethoxycarbonyl, 2-furfuryloxycarbonyl, 1-adamantyloxycarbonyl, vinyloxycarbonyl, allyloxycarbonyl, 4-ethoxy-1-naphthyloxycarbonyl, 8-quinolyloxycarbonyl, or S-benzylthiocarbonyl; an acyl group such as acetyl, formyl, chloroacetyl, dichloroacetyl, trichloroacetyl, trifluoroacetyl, methoxyacetyl, phenoxyacetyl, pivaloyl, or benzoyl; a lower alkyl group such as methyl, tert-butyl, 2,2,2-trichloroethyl, or 2-trimethylsilylethyl; a lower alkenyl group such as allyl; a lower alkynyl group such as propargyl; an ar-lower alkyl group such as benzyl, 4-methoxybenzyl, 3,4-dimethoxybenzyl, diphenylmethyl, or trityl; oxygen-containing and sulfur-containing heterocyclic groups such as tetrahydrofuryl, tetrahydropyranyl, or tetrahydrothiopyranyl; lower alkoxy- and lower alkylthio-lower alkyl groups such as methoxymethyl, methylthiomethyl, benzyloxymethyl, 2-methoxyethoxymethyl, 2,2,2-trichloroethoxymethyl, 2-(trimethylsilyl) ethoxymethyl, 1-ethoxyethyl, or 1-methyl-1-methoxyethyl; lower alkyl- and aryl-sulfonyl groups such as methanesulfonyl or p-toluenesulfonyl; and a substituted silyl group such as trimethylsilyl, triethylsilyl, triisopropylsilyl, diethylisopropylsilyl, tert-butyldimethylsilyl, tert-butyldiphenylsilyl, diphenylmethylsilyl, or tert-butylmethoxyphenylsilyl.

Protecting groups for an amino group may include all groups that can be used as common protecting groups for an amino group. Examples of such a protecting group may include: an alkoxycarbonyl group such as methoxycarbonyl, 2,2,2-trichloroethoxycarbonyl, 2,2,2-tribromoethoxycarbonyl, 2-trimethylsilylethoxycarbonyl, 1,1-dimethylpropoxycarbonyl, tert-butoxycarbonyl, vinyloxycarbonyl, allyloxycarbonyl, 1-adamantyloxycarbonyl, benzyloxycarbonyl, 4-nitrobenzyloxycarbonyl, 2-bromobenzyloxycarbonyl, 4-methoxybenzyloxycarbonyl, 2,4-dichlorobenzyloxycarbonyl, diphenylmethoxycarbonyl, 4-(phenylazo)benzyloxycarbonyl, 2-furfuryloxycarbonyl, or 8-quinolyloxycarbonyl; an acyl group such as (mono-, di-, tri-)chloroacetyl, trifluoroacetyl, phenylacetyl, formyl, acetyl, benzoyl, phthaloyl, succinyl, alanyl, or leucyl; an ar lower alkyl group such as benzyl, diphenyl, methyl, or trityl; an arylthio group such as 2-nitrophenylthio or 2,4-dinitrophenylthio; an alkyl- or arylsulfonyl group such as methanesulfonyl or p-toluenesulfonyl; a di-lower alkylamino-lower alkylidene group such as N,N-dimethylaminomethylene; an ar-lower alkylidene group such as benzylidene, 2-hydroxybenzylidene, 2-hydroxy-5-chlorobenzylidene, or 2-hydroxy-1-naphthylmethylene; a nitrogen-containing heterocyclic alkylidene group such as 3-hydroxy-4-pyridylmethylene; a cycloalkylidene group such as cyclohexylidene, 2-ethoxycarbonylcyclohexylidene, 2-ethoxycarbonylcyclopentylidene, 2-acetylcyclohexylidene, or 3,3-dimethyl-5-oxycyclohexylidene; a diaryl- or diar-lower alkylphosphoryl group such as diphenylphosphoryl or dibenzylphosphoryl; an oxygen-containing heterocyclic alkyl group such as 5-methyl-2-oxo-2H-1,3-dioxole-4-yl-methyl; and a substituted silyl group such as trimethylsilyl.

A salt of the compound represented by the general formula [1] may include salts in commonly known basic groups such as an amino group or acidic groups such as a hydroxyl or carboxyl group.

Examples of such salts in basic groups may include: salts with mineral acids such as hydrochloric acid, hydrobromic acid, nitric acid, or sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, or trifluoroacetic acid; and salts with sulfonic acids such as methanesulfonic acid, benzenesulfonic acid, p-toluenesulfonic acid, mesitylenesulfonic acid, or naphthalenesulfonic acid.

Examples of salts in acidic groups may include: salts with alkaline metals such as sodium or potassium; salts with alkaline-earth metals such as calcium or magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

Among the aforementioned salts, pharmacologically acceptable salts are preferable.

When isomers (for example, optical isomers, geometric isomers, and tautomers) are present in the alkyl ether derivative represented by the general formula [1] or a salt thereof, the present invention includes all these isomers, and further includes hydrates, solvates, and all crystal forms.

Preferred examples of the alkyl ether derivative represented by the general formula [1] or a salt thereof of the present invention may be compounds wherein, the following portion:

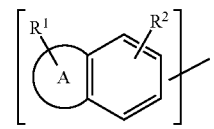

is any one of the following (A), (B), and (C):

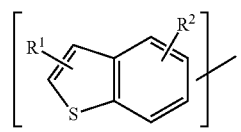

(A)

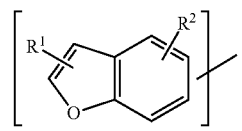

(B)

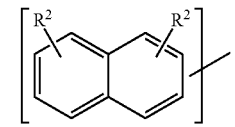

(C)

wherein, preferably, $R^1$ represents a hydrogen atom; and $R^2$ represents a hydrogen atom, a halogen atom or an alkoxy group.

Moreover, the above compound wherein, in general formula [1], m is 2 and n is an integer of 2 or 3, is preferable. Furthermore, the above compound wherein, in the above formula, p is an integer of 1 or 2, is more preferable.

A compound wherein, in the above (A), each of $R^1$ and $R^2$ represents a hydrogen atom; $R^3$ represents a hydroxyl group; m is 2; n is 3; and p is 1, is most preferable.

Next, the production method of the alkyl ether derivative represented by the general formula [1] or a salt thereof will be described.

The alkyl ether derivative represented by the general formula [1] or a salt thereof can be produced by known methods or by appropriately combining such methods. For example, it can be produced by the following production method.

[Production Method 1]
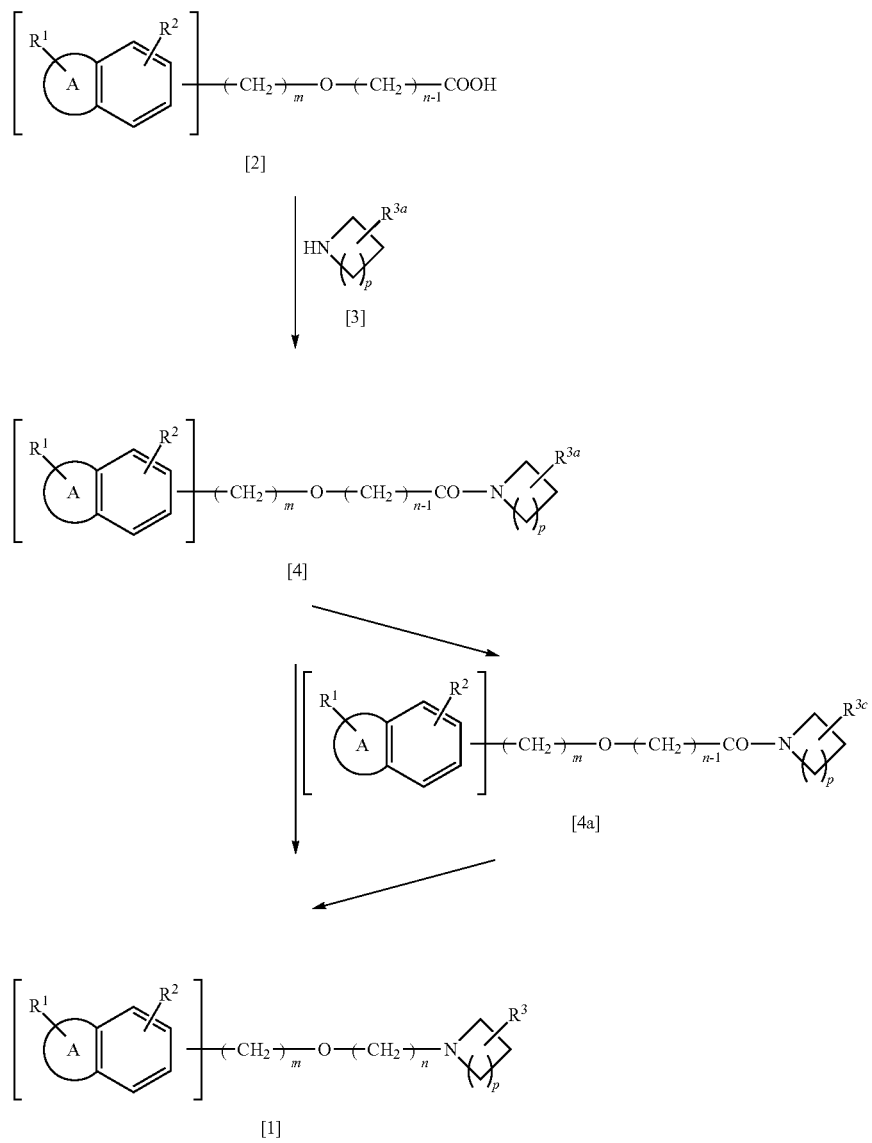
[Production Method 2]    [Production Method 3]
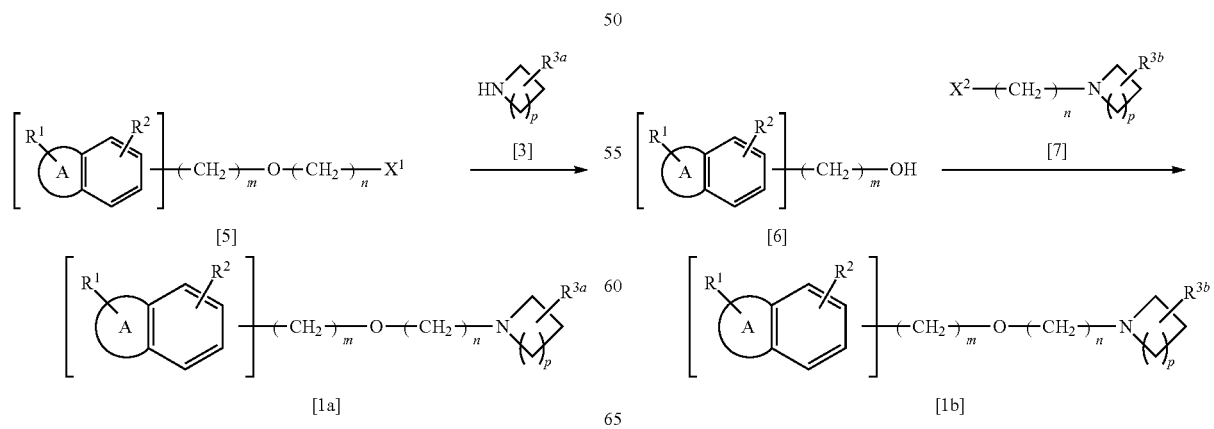

[Production Method 4]

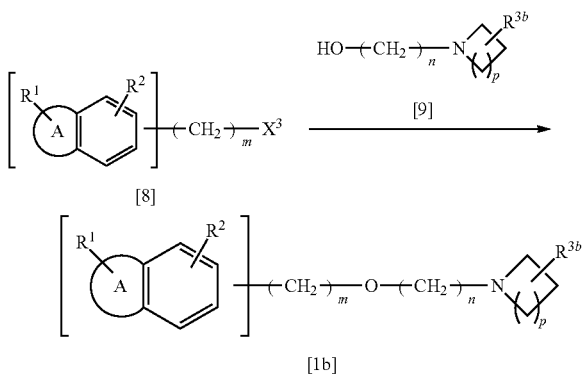

[Production Method 5]

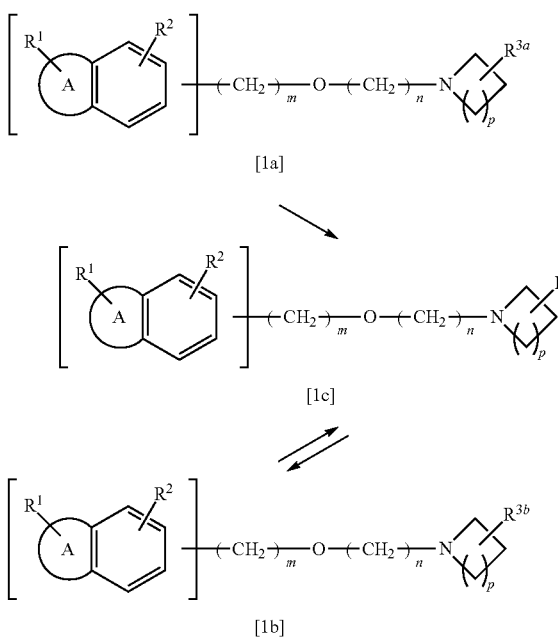

wherein $R^1$, $R^2$, $R^3$, A, m, n, and p have the same meanings as defined above; $R^{3a}$ represents a dialkylamino group, a monoalkylamino group that is protected, an amino group that is protected, or a hydroxyl group that may be protected; $R^{3b}$ represents a dialkylamino group, a monoalkylamino group that is protected, an amino group that is protected, or a hydroxyl group that is protected; $R^{3c}$ represents a hydroxyl group that is protected; $R^{3d}$ represents a dialkylamino group, a monoalkylamino group, an amino group, or a hydroxyl group; and each of $X^1$, $X^2$, and $X^3$ represents a leaving group.

Examples of such a leaving group may include a halogen atom, a lower alkylsulfonyloxy group, and an arylsulfonyloxy group.

Next, each production method will be described.
[Production Method 1]
(1-1) The compound represented by the general formula [3] is allowed to react with the compound represented by the general formula [2] or a reactive derivative thereof, so as to produce the compound represented by the general formula [4].

This reaction may be carried out by known methods, for example, by the method described in *Jikken Kagaku Koza, Vol.* 22, The Chemical Society of Japan, pp. 137-173, 1992, (Maruzen), or a method equivalent thereto.

Examples of the reactive derivative of the compound represented by the general formula [2] may include an acid halide, an acid anhydride, an active amide, and an active ester.

When the compound represented by the general formula [2] is used in the form of a free acid, the reaction is preferably carried out in the presence of a condensing agent.

Examples of such a condensing agent may include: carbodiimides such as N,N'-dicyclohexylcarbodiimide; halogenating agents such as thionyl chloride or oxalyl chloride; acid halides such as ethoxycarbonyl chloride; active amidation agents such as carbonyldiimidazole; and azidation agents such as diphenylphosphoric azide.

A condensing agent may be used at a molar ratio to the compound represented by the general formula [2] of 1 or greater:1, and more preferably between 1:1 and 5:1.

Any solvent may be used in this reaction, as long as it does not affect the reaction. Examples of such a solvent may include: water; halogenated hydrocarbons such as methylene chloride or chloroform; ethers such as tetrahydrofuran or dioxane; aromatic hydrocarbons such as benzene, toluene, or xylene; sulfoxides such as dimethyl sulfoxide; amides such as N,N-dimethylformamide; esters such as ethyl acetate; ketones such as acetone or methyl ethyl ketone; nitriles such as acetonitrile; and heteroaromatics such as pyridine. These solvents may also be used in combination.

This reaction can be carried out in the presence of a base.
Examples of such a base may include organic bases and inorganic bases, such as triethylamine, diisopropylethylamine, 1,8-diazabicyclo[5.4.0]undec-7-ene (DBU), pyridine, potassium tert-butoxide, sodium carbonate, sodium bicarbonate, potassium carbonate, or sodium hydroxide.

Such a base is used to the compound represented by the general formula [2] at a molar ratio of 0.5 or greater:1, and preferably at a molar ratio between 1:1 and 10:1.

The compound represented by the general formula [3] is used to the compound represented by the general formula [2] at a molar ratio of 1 or greater:1, and preferably at a molar ratio between 1:1 and 20:1.

This reaction may be carried out generally between −100° C. and 200° C., and preferably between −60° C. and 100° C., for 10 minutes to 20 hours.

The obtained compound represented by the general formula [4] may directly be used in the subsequent reaction without being isolated.
(1-2) When $R^{3a}$ in the compound represented by the general formula [4] is a hydroxyl group that is not protected, the above compound of the general formula [4] is subjected to a common hydroxyl group-protecting reaction, so as to induce it to the compound represented by the general formula [4a].

This reaction may be carried out by known methods, for example, by the method described in Protective Groups in Organic Synthesis, pp. 10-118, 1991, Theodora W. Green, John Wiley & Sons, Inc., or a method equivalent thereto.

Examples of a compound used in such a hydroxyl group-protecting reaction may include: acid anhydrides such as acetic anhydride; acid halides such as benzoyl chloride, pivaloyl chloride, methoxycarbonyl chloride, or ethoxycarbonyl chloride; halides such as methoxymethyl chloride, benzyloxymethyl chloride, benzyl chloride, benzyl bromide, trityl chloride, or triethylsilyl chloride; organic carboxylic acid compounds such as benzoic acid; dialkoxyalkyl compounds such as dimethoxymethane; and noncyclic and cyclic alkoxyvinyl compounds such as 2-methoxypropene or 3,4-dihydro-2H-pyran.

The compound used in a hydroxyl group-protecting reaction is used at a molar ratio to the compound represented by the general formula [4] of 1 or greater:1, and preferably between 1:1 and 2:1.

A hydroxyl group-protecting reaction using an acid anhydride, an acid halide, or a halide, is generally carried out in the presence of a base or a dehalogenating agent. Examples of a base used herein may include organic bases and inorganic bases, such as triethylamine, N,N-diisopropylethylamine, 1,8-diazabicyclo[5.4.0]undec-7-ene (DBU), pyridine, 4-dimethylaminopyridine, potassium tert-butoxide, sodium hydroxide, potassium hydroxide, or sodium hydride. Examples of a dehydrogenating agent may include silver compounds such as silver oxide.

A hydroxyl group-protecting reaction using an organic carboxylic acid compound is carried out in a dehydrating agent. Examples of a dehydrating agent used herein may include triphenylphosphine-diisopropyl=azodicarboxylate.

In addition, a hydroxyl group-protecting reaction using an acid anhydride, a dialkoxyalkyl compound, or a noncyclic or cyclic alkoxyvinyl compound, is generally carried out in the presence of an acid catalyst. Examples of an acid used herein may include: organic sulfonic acids such as p-toluenesulfonic acid; inorganic acids such as hydrochloric acid or sulfuric acid; and Lewis acids such as boron trifluoride, a boron trifluoride-diethyl ether complex, or a boron trifluoride-tetrahydrofuran complex.

A base, a dehalogenating agent, or a dehydrating agent used in this reaction may be used at a molar ratio to the compound used in the hydroxyl group-protecting reaction of 1 or greater:1, and preferably between 1:1 and 2:1. An acid catalyst may be used at a molar ratio to the compound represented by the general formula [4] between 0.001:1 and 10:1, and preferably between 0.01:1 and 1:1.

Any solvent may be used in this reaction, as long as it does not affect the reaction. Examples of such a solvent may include: halogenated hydrocarbons such as methylene chloride or chloroform; ethers such as tetrahydrofuran or dioxane; aromatic hydrocarbons such as benzene, toluene, or xylene; sulfoxides such as dimethyl sulfoxide; amides such as N,N-dimethylformamide; esters such as ethyl acetate; ketones such as acetone or methyl ethyl ketone; nitriles such as acetonitrile; and heteroaromatics such as pyridine. These solvents may also be used in combination.

This reaction may be carried out generally between −100° C. and 200° C., and preferably between −60° C. and 100° C., for 10 minutes to 30 hours.

Moreover, the reaction reagent or base used in each of the aforementioned production methods may also be used as a solvent, depending on the properties thereof.

The obtained compound represented by the general formula [4a] may be used in the subsequent reaction without being isolated.

(1-3) The compound represented by the general formula [4] or [4a] is subjected to a common reduction reaction, so as to produce the compound represented by the general formula [1].

This reduction reaction may be carried out by known methods, for example, by the method described in *Shin Jikken Kagaku Koza*, Vol. 15, [II], The Chemical Society of Japan, pp. 29-244, 1977, (Maruzen), or a method equivalent thereto.

Any solvent may be used in this reaction, as long as it does not affect the reaction. Examples of such a solvent may include: halogenated hydrocarbons such as methylene chloride or chloroform; ethers such as tetrahydrofuran or dioxane; aromatic hydrocarbons such as benzene, toluene, or xylene; and alcohols such as methanol, ethanol, or isopropanol. These solvents may also be used in combination.

Examples of a reducing agent may include: aluminum hydrides such as lithium aluminum hydride; and boron hydrides such as diborane, a borane-tetrahydrofuran complex, a borane-dimethyl sulfide complex, or sodium borohydride.

When sodium borohydride is used as a reducing agent, the reaction is preferably carried out in the presence of Lewis acid such as boron trifluoride, a boron trifluoride-diethyl ether complex, or a boron trifluoride-tetrahydrofuran complex.

Such a reducing agent may be used at a molar ratio to the compound represented by the general formula [4] or [4a] of 0.2:1 or greater, and preferably between 0.5:1 and 10:1.

Lewis acid may be used at a molar ratio to such a reducing agent of 1 or greater:1, and preferably between ⅔:1 and 2:1.

This reaction may be carried out generally between −50° C. and 200° C., and preferably between 0° C. and 110° C., for 10 minutes to 20 hours.

[Production Method 2]

The compound represented by the general formula [3] is allowed to react with the compound represented by the general formula [5] in the presence or absence of a base, so as to product the compound represented by the general formula [1a].

Any solvent may be used in this reaction, as long as it does not affect the reaction. Examples of such a solvent may include: water; halogenated hydrocarbons such as methylene chloride or chloroform; aromatic hydrocarbons such as benzene, toluene, or xylene; ethers such as tetrahydrofuran or dioxane; alcohols such as methanol and ethanol; nitriles such as acetonitrile; amides such as N,N-dimethylformamide; sulfoxides such as dimethyl sulfoxide. These solvents may also be used in combination.

Examples of a base that is used as necessary may include organic bases and inorganic bases, such as triethylamine, diisopropylethylamine, 1,8-diazabicyclo[5.4.0]undec-7-ene (DBU), pyridine, potassium tert-butoxide, sodium carbonate, sodium bicarbonate, potassium carbonate, or sodium hydroxide.

Such a base may be used at a molar ratio to the compound represented by the general formula [5] of 0.5 or greater:1, and preferably between 1:1 and 20:1.

Moreover, this reaction may also be carried out in the presence of a catalyst.

Examples of a catalyst may include potassium iodide and sodium iodide.

Such a catalyst may be used at a molar ratio to the compound represented by the general formula [5] of between 0.01:1 and 10:1, and preferably between 0.1:1 and 1:1.

The compound represented by the general formula [3] may be used to the compound represented by the general formula [5] at a molar ratio of 1 or greater:1, and preferably at a molar ratio between 1:1 and 20:1.

This reaction may be carried out generally between 0° C. and 200° C., and preferably between 20° C. and 150° C., for 10 minutes to 20 hours.

Moreover, the reaction reagent or base used in each of the aforementioned production methods may also be used as a solvent, depending on the properties thereof.

[Production Method 3]

The compound represented by the general formula [7] is allowed to react with the compound represented by the general formula [6] in the presence of a base, so as to produce the compound represented by the general formula [1b].

This reaction may be carried out by known methods, for example, by the methods described in Tetrahedron Letters, Vol. 38, pp. 3251-3254, 1975, and *Shin Jikken Kagaku Koza*, Vol. 14, [I], The Chemical Society of Japan, pp. 567-611, 1977, (Maruzen), or methods equivalent thereto.

Examples of a base may include sodium hydride, sodium hydroxide, potassium hydroxide, and potassium tert-butoxide.

Any solvent may be used in this reaction, as long as it does not affect the reaction. Examples of such a solvent may include: halogenated hydrocarbons such as methylene chloride or chloroform; ethers such as tetrahydrofuran or dioxane; aromatic hydrocarbons such as benzene, toluene, or xylene; sulfoxides such as dimethyl sulfoxide; amides such as N,N-dimethylformamide; and water. These solvents may also be used in combination.

This reaction can be carried out in the presence or absence of a catalyst.

Examples of a catalyst used herein may include commonly known phase-transfer catalysts of quaternary ammonium salts. Preferred examples may include tetra-n-butyl ammonium hydrogen sulfate and tetra-n-butyl ammonium bromide.

In this reaction, each of the compound represented by the general formula [7] and a base may be used to the compound represented by the general formula [6] at a molar ratio of 1 or greater:1, and preferably at a molar ratio between 1:1 and 20:1. A catalyst is used to the above compound at a molar ratio between 0.001:1 and 1:1.

This reaction may be carried out generally between −50° C. and 200° C., and preferably between 0° C. and 150° C., for 10 minutes to 20 hours.

[Production Method 4]

The compound represented by the general formula [9] is allowed to react with the compound represented by the general formula [8] in the presence or absence of a base, so as to produce the compound represented by the general formula [1b].

This reaction may be carried out by known methods, for example, by the same method as Production method 3.

[Production Method 5]

(5-1) The compound represented by the general formula [1a] or the compound represented by the general formula [1b] is subjected to a common deprotection reaction, so as to produce the compound represented by the general formula [1c].

This reaction may be carried out by known methods, for example, by the method described in Protective Groups in Organic Synthesis, pp. 10-118 and 309-405, 1991, Theodora W. Green, John Wiley & Sons, Inc., or a method equivalent thereto.

This deprotection reaction is carried out, for example, under conditions consisting of hydrolysis and transesterification in the presence of an acid or base, substitution and dissociation reaction in the presence of an acid catalyst, or hydrogenation in the presence of a metal catalyst. Examples of a base used herein may include inorganic bases such as sodium hydroxide, potassium hydroxide, or sodium hydride. Examples of an acid used herein may include: organic sulfonic acids such as p-toluenesulfonic acid; organic carboxylic acids such as formic acid, acetic acid, or trifluoroacetic acid; inorganic acids such as hydrochloric acid or sulfuric acid; and Lewis acids such as boron trifluoride, a boron trifluoride-diethyl ether complex, or a boron trifluoride-tetrahydrofuran complex. Examples of a metal catalyst may include transition metals such as platinum, palladium, palladium carbon, or palladium hydroxide.

The base used in this reaction may be used at a molar ratio to the compound represented by the general formula [1a] or [1b] of 1 or greater:1, and preferably between 1:1 and 5:1. The acid may be used to the compound represented by the general formula [1a] or [1b] at a molar ratio of 1 or greater:1, and preferably at a molar ratio between 1.1:1 and 100:1. In addition, the metal catalyst may be used to the compound represented by the general formula [1a] or [1b] at a catalytic amount, and preferably at a weight ratio between 0.01% and 30%.

Any solvent may be used in this reaction, as long as it does not affect the reaction. Examples of such a solvent may include: halogenated hydrocarbons such as methylene chloride or chloroform; ethers such as tetrahydrofuran or dioxane; aromatic hydrocarbons such as benzene, toluene, or xylene; sulfoxides such as dimethyl sulfoxide; amides such as N,N-dimethylformamide; esters such as ethyl acetate; ketones such as acetone or methyl ethyl ketone; nitriles such as acetonitrile; alcohols such as methanol or ethanol; organic carboxylic acids such as formic acid or acetic acid; and water. These solvents may also be used in combination.

This reaction may be carried out generally between −100° C. and 200° C., and preferably between −60° C. and 120° C., for 10 minutes to 20 hours.

Moreover, the base used in each of the aforementioned production methods may also be used as a solvent, depending on the properties thereof.

(5-2) The compound represented by the general formula [1c] is subjected to a common protection reaction for a hydroxyl group and an amino group or to an alkylation reaction of an amino group, so as to induce it to the compound represented by the general formula [1b].

The hydroxyl group-protecting reaction may be carried out by known methods, for example, by the method described in Protective Groups in Organic Synthesis, pp. 10-118, 1991, Theodora W. Green, John Wiley & Sons, Inc., or a method equivalent thereto. This reaction may be carried out by the same method as in Example (1-2).

The amino group-protecting reaction may be carried out by known methods, for example, by the method described in Protective Groups in Organic Synthesis, pp. 309-405, 1991, Theodora W. Green, John Wiley & Sons, Inc., or a method equivalent thereto.

Examples of a compound used in the amino group-protecting reaction may include: acid anhydrides such as acetic anhydride; and acid halides such as acetyl chloride, benzoyl chloride, methanesulfonyl chloride, or tosyl chloride. Such a compound may be used at a molar ratio to the compound represented by the general formula [1c] of 1 or greater:1, and preferably between 1:1 and 2:1.

This reaction is generally carried out in the presence of a base. Examples of such a base may include organic bases and inorganic bases, such as triethylamine, diisopropylethylamine, 1,8-diazabicyclo[5.4.0]undec-7-ene (DBU), pyridine, potassium tert-butoxide, sodium carbonate, sodium bicarbonate, potassium carbonate, or sodium hydroxide.

Such a base may be used at a molar ratio to the compound represented by the general formula [1c] of 0.5 or greater:1, and preferably between 1:1 and 10:1.

Any solvent may be used in this reaction, as long as it does not affect the reaction. Examples of such a solvent may include: halogenated hydrocarbons such as methylene chloride or chloroform; ethers such as tetrahydrofuran or dioxane; aromatic hydrocarbons such as benzene, toluene, or xylene; sulfoxides such as dimethyl sulfoxide; amides such as N,N-dimethylformamide; esters such as ethyl acetate; ketones such as acetone or methyl ethyl ketone; nitriles such as acetonitrile; alcohols such as methanol or ethanol; and water. These solvents may also be used in combination.

This reaction may be carried out generally between −100° C. and 200° C., and preferably between −60° C. and 100° C., for 10 minutes to 20 hours.

Furthermore, an alkylation reaction of an amino group may be carried out by known methods, for example, by the method described in *Shin Jikken Kagaku Koza*, Vol. 14, [III], The Chemical Society of Japan, pp. 1332-1399, 1977, (Maruzen), or a method equivalent thereto.

Examples of a compound used in such an alkylation reaction of an amino group may include carbonyl compounds such as formalin, paraformaldehyde, acetaldehyde, or acetone.

Such a compound may be used at a molar ratio to the compound represented by the general formula [1c] of 1 or greater:1, and preferably between 1:1 and 5:1.

This reaction is generally carried out in the presence of a reducing agent. Examples of a reducing agent may include boron hydrides such as sodium borohydride.

Such a reducing agent may be used at a molar ratio to a carbonyl compound of 0.5 or greater:1, and preferably between 1:1 and 10:1.

Any solvent may be used in this reaction, as long as it does not affect the reaction. Examples of such a solvent may include: water; halogenated hydrocarbons such as methylene chloride or chloroform; aromatic hydrocarbons such as benzene, toluene, or xylene; ethers such as tetrahydrofuran or dioxane; and alcohols such as methanol or ethanol. These solvents may also be used in combination.

This reaction may be carried out generally between −100° C. and 200° C., and preferably between 0° C. and 100° C., for 10 minutes to 30 hours.

The reaction reagent used in each of the aforementioned production methods may also be used as a solvent, depending on the properties thereof.

In addition, in the aforementioned production methods, the compounds represented by the general formulas [1a], [1b], [1c], [2] to [9], and [4a], can also be used in the form of salts. Examples of such salts are the same as those of the compound represented by the general formula [1].

When isomers (for example, optical isomers, geometric isomers, and tautomers) are present in the compounds represented by the general formulas [1a], [1b], [1c], [2] to [9], and [4a], all these isomers can be used. Further, hydrates, solvates, and all crystal forms can also be used.

Furthermore, the compounds represented by the general formulas [1a], [1b], [1c], [2] to [9], and [4a], may directly be used in the subsequent reaction without being isolated.

When the compounds represented by the general formulas [1], [1a], [1b], [1c], [2] to [9], and [4a], comprise a hydroxyl group, an amino group, or a carboxyl group, such a hydroxyl group, an amino group, or a carboxyl group has previously been protected with a common protecting group, and after completion of the reaction, such a protecting group can be dissociated by known methods, as necessary. Moreover, the alkyl ether derivatives represented by the general formulas [1], [1a], [1b], and [1c], or salts thereof are subjected, for example, to the appropriate combined use of known methods such as an oxidization reaction, a reduction reaction, an alkylation reaction, a halogenation reaction, a sulfonylation reaction, a substitution reaction, a dehydration reaction, and a hydrolysis reaction, so as to induce them to another type of alkyl ether derivative represented by the general formula [1] or a salt thereof.

The thus obtained alkyl ether derivatives represented by the general formulas [1], [1a], [1b], and [1c], or salts thereof, can be isolated and purified by common methods such as extraction, crystallization, distillation, or chromatography.

Next, a method for producing the compounds represented by the general formulas [2] and [5] used as raw materials for producing the compound of the present invention will be described.

The compound represented by the general formula [2] can be produced by known methods or by appropriately combining such methods, for example, by the following production method A.

Production Method A

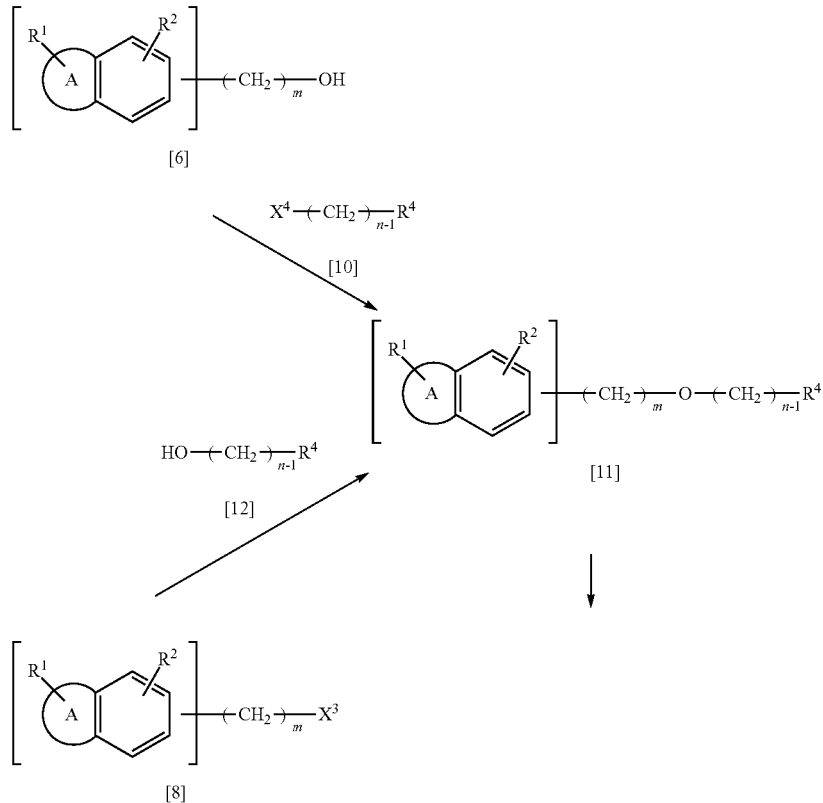

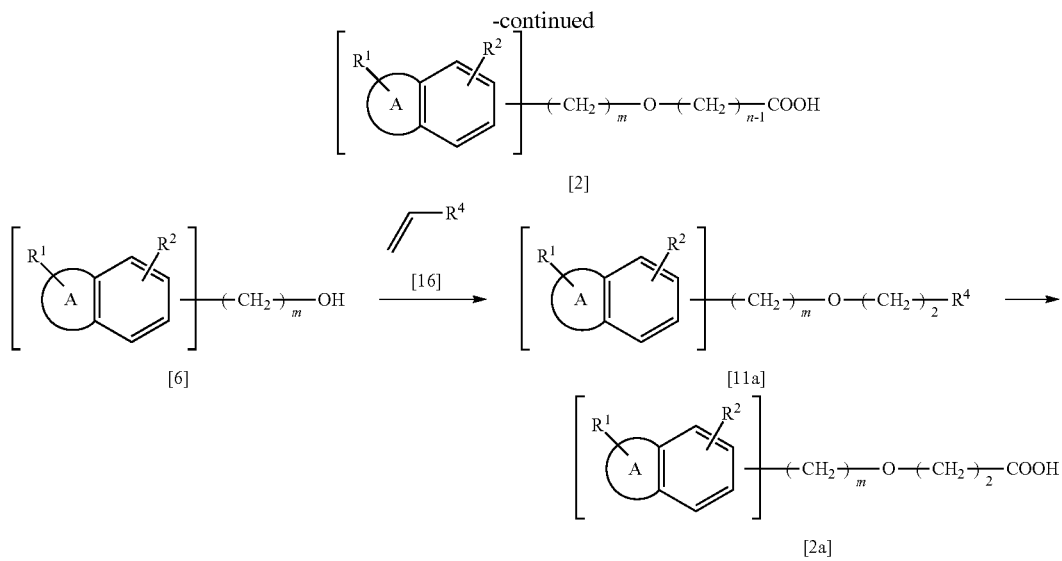

wherein $R^1$, $R^2$, A, $X^3$, m, and n have the same meanings as defined above; $R^4$ represents a cyano group, a lower alkoxycarbonyl group, a dialkylaminocarbonyl group, or a cyclic aminocarbonyl group; and $X^4$ represents a leaving group.

(A-1) The compound represented by the general formula [10] is allowed to react with the compound represented by the general formula [6] in the presence of a base, so as to produce the compound represented by the general formula [11].

This reaction may be carried out by known methods, for example, by the method described in *Shin Jikken Kagaku Koza*, Vol. 14, [I], The Chemical Society of Japan, pp. 567-611, 1977, (Maruzen), or a method equivalent thereto.

(A-2) The compound represented by the general formula [12] is allowed to react with the compound represented by the general formula [8] in the presence of a base, so as to produce the compound represented by the general formula [11].

This reaction may be carried out by known methods, for example, by the same method as Production method (A-1).

(A-3) The compound represented by the general formula [11] is subjected to a common hydrolysis reaction of a nitrile, ester, or amide, so as to produce the compound represented by the general formula [2]. This reaction may be carried out by known methods, for example, by the methods described in *Shin Jikken Kagaku Koza*, Vol. 14, [II], The Chemical Society of Japan, pp. 930-950, 1977, (Maruzen), and Protective Groups in Organic Synthesis, pp. 152-192, 1981, Theodora W. Green, John Wiley & Sons. Inc., or methods equivalent thereto.

(A-4) The compound represented by the general formula [16] is allowed to react with the compound represented by the general formula [6] by the Michael addition reaction in the presence of a base, so as to produce the compound represented by the general formula [11a]. This reaction may be carried out by known methods, for example, by the methods described in Chemical & Pharmaceutical Bulletin, Vol. 41, pp. 1659-1663, 1993; *Shin Jikken Kagaku Koza*, Vol. 14, [I], The Chemical Society of Japan, pp. 585-587, 1977, (Maruzen); and JP-A-3-99038, or methods equivalent thereto.

(A-5) The compound represented by the general formula [11a] is subjected to a common hydrolysis reaction of a nitrile, ester, or amide, so as to produce the compound represented by the general formula [2a]. This reaction may be carried out by known methods, for example, by the same method as that described in (A-3) above.

The compound represented by the general formula [5] can be produced by known methods or by appropriately combining such methods, for example, by the following production method B.

Production Method B

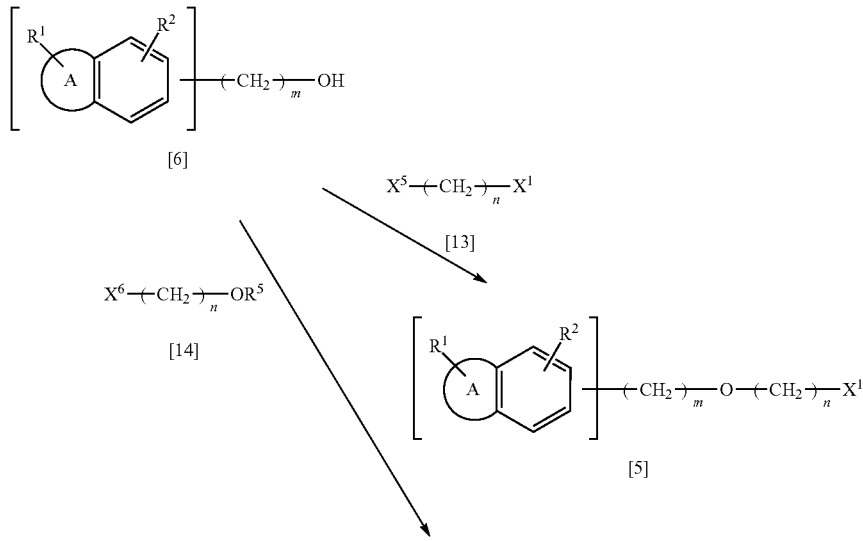

-continued

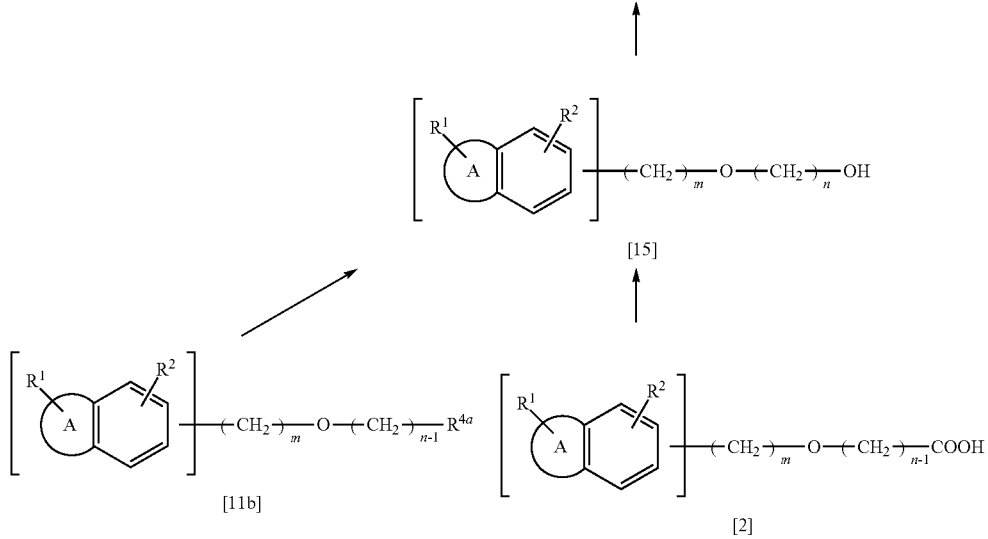

wherein $R^1$, $R^2$, $X^1$, A, m, and n have the same meanings as defined above; $R^{4a}$ represents an alkoxycarbonyl group; $R^5$ represents a hydroxyl-protecting group that is stable under basic conditions; each of $X^5$ and $X^6$ represents a leaving group.

Examples of a hydroxyl-protecting group that is stable under basic conditions may include: lower alkyl groups such as tert-butyl; lower alkenyl groups such as allyl; ar-lower alkyl groups such as benzyl, 4-methoxybenzyl, 3,4-dimethoxybenzyl, diphenylmethyl, or trityl; oxygen-containing and sulfur-containing heterocyclic groups such as tetrahydrofuryl, tetrahydropyranyl, or tetrahydrothiopyranyl; lower alkoxy-lower alkyl groups such as methoxymethyl, 2-(trimethylsilyl)ethoxymethyl, or 1-methyl-1-methoxyethyl; and substituted silyl groups such as tert-butyldimethylsilyl or diphenylmethylsilyl. (B-1) The compound represented by the general formula [13] is allowed to react with the compound represented by the general formula [6], so as to produce the compound represented by the general formula [5]. This reaction may be carried out by known methods, for example, by the methods described in Tetrahedron Letters, Vol. 38, pp. 3251-3254, 1975, and *Shin Jikken Kagaku Koza*, Vol. 14, [I], The Chemical Society of Japan, pp. 567-611, 1977, (Maruzen), or methods equivalent thereto.

(B-2) The compound represented by the general formula [14] is allowed to react with the compound represented by the general formula [6], and thereafter, a protecting group is dissociated, so as to produce the compound represented by the general formula [15]. This reaction may be carried out by known methods, for example, by the same method as Production method 3, followed by dissociation of a protecting group.

(B-3) The compound represented by the general formula [2] or the compound represented by the general formula [11b] is subjected to a common reduction reaction, so as to produce the compound represented by the general formula [15]. This reduction reaction may be carried out by known methods, for example, by the method described in *Shin Jikken Kagaku Koza*, Vol. 15, pp. 26-244, 1977, (Maruzen), or a method equivalent thereto.

(B-4) A halogenating agent or a sulfonylating agent is allowed to react with the compound represented by the general formula [15] in the presence or absence of a base, so as to produce the compound represented by the general formula [5].

Examples of a solvent used in this reaction may include: halogenated hydrocarbons such as methylene chloride or chloroform; ethers such as tetrahydrofuran or dioxane; aromatic hydrocarbons such as benzene, toluene, or xylene; sulfoxides such as dimethyl sulfoxide; amides such as N,N-dimethylformamide; esters such as ethyl acetate; and nitriles such as acetonitrile. These solvents may also be used in combination.

In addition, examples of a base used in this reaction as necessary may include organic or inorganic bases, such as triethylamine, diisopropylethylamine, 1,8-diazabicyclo[5.4.0]undec-7-ene (DBU), pyridine, potassium tert-butoxide, sodium carbonate, potassium carbonate, or sodium hydride.

Examples of a halogenating agent may include phosphorus oxychloride, phosphorous oxybromide, phosphorus trichloride, phosphorus pentachloride, carbon tetrabromide-triphenylphosphine, and thionyl chloride.

Examples of a sulfonylating agent may include methanesulfonyl chloride and p-toluenesulfonyl chloride.

Such a halogenating agent, sulfonylating agent, or base may be used to the compound represented by the general formula [15] at a molar ratio of 1 or greater:1, and preferably at a molar ratio between 1:1 and 2:1.

This reaction may be carried out generally between −50° C. and 200° C., and preferably between 0° C. and 50° C., for 10 minutes to 30 hours.

When the compounds represented by the general formulas [2], [2a], [6], [8], [10] to [16], [11a], and [11b] in the production methods A and B, comprise a hydroxyl group, an amino group, or a carboxyl group, such a hydroxyl group, an amino group, or a carboxyl group has previously been protected with a common protecting group, and after completion of the reaction, such a protecting group can be dissociated by known methods, as necessary.

Moreover, when isomers (for example, optical isomers, geometric isomers, and tautomers) are present in the compounds represented by the general formulas [2], [2a], [6], [8], [10] to [16], [11a], and [11b], all these isomers can be used. Further, hydrates, solvates, and all crystal forms can also be used.

Furthermore, the compounds represented by the general formulas [2], [2a], [6], [8], [10] to [16], [11a], and [11b], may directly be used in the subsequent reaction without being isolated.

The compound of the present invention can be formulated into pharmaceutical preparations such as oral agents (a tablet, a capsule, a powder, a granule, a fine granules, a pill, a suspension, an emulsion, a syrup, etc.), injections, or eye-drops, by adding thereto various types of pharmaceutical additives such as an excipient, a binder, a disintegrator, a disintegration inhibitor, an anticaking/antiadhesion agent, a lubricant, an absorption/adsorption carrier, a solvent, an extender, an isotonizing agent, a solubilizer, an emulsifier, a suspending agent, a thickener, a coating agent, an absorbefacient, a gelation/agglutination promoter, a light stabilizer, a preservative, an anti-moisture agent, an emulsion, suspension or dispersion stabilizer, a coloration preventing agent, a deoxidizer/antioxidant, correctives, a coloring agent, a whipping agent, an antifoaming agent, a soothing agent, an anti-static agent, or a buffer/pH adjuster.

The aforementioned various types of agents are formulated by common methods.

Oral solid preparations such as a tablet, a powder, or a granule may be prepared according to common methods, using the following pharmaceutical additives for such solid preparations, for example: excipients such as lactose, saccharose, sodium chloride, glucose, starch, calcium carbonate, kaolin, crystalline cellulose, anhydrous dicalcium phosphate, corn starch, or alginic acid; binders such as simple syrup, glucose solution, starch solution, gelatin solution, polyvinyl alcohol, polyvinylpyrrolidone, shellac, methylcellulose, ethylcellulose, sodium alginate, gum Arabic, hydroxypropylmethylcellulose, hydroxypropylcellulose, water, or ethanol; disintegrators such as dry starch, alginic acid, agar powders, starch, partial a starch, crosslinked polyvinylpyrrolidone, carboxymethylcellulose, crosslinked carboxymethylcellulose sodium, carboxymethylcellulose calcium, or sodium starch glycolate; disintegration inhibitors such as stearyl alcohol, stearic acid, cacao butter, or hydrogenated oil; anticaking/antiadhesion agents such as aluminum silicate, calcium hydrogen phosphate, magnesium oxide, talc, or silicic acid anhydride; lubricants such as carnauba wax, light anhydrous silicic acid, aluminum silicate, magnesium silicate, hardened oil, hardened vegetable oil derivative, sesame oil, white beeswax, titanium oxide, dry aluminum hydroxide gel, stearic acid, calcium stearate, magnesium stearate, talc, calcium hydrogen phosphate, sodium lauryl sulfate, or polyethylene glycol; absorption promoters such as quaternary ammonium salts, sodium lauryl sulfate, urea, or enzyme; and absorption/adsorption carriers such as starch, lactose, kaolin, bentonite, silicic acid anhydride, hydrous silicon dioxide, magnesium aluminometasilicate, or colloidal silicic acid.

Moreover, as necessary, a tablet may be processed into a tablet coated with a common coating agent, such as a sugar-coated tablet, a gelatin-coated tablet, a gastric coated tablet, an enteric coated tablet, and a water-soluble film coated tablet.

A capsule is prepared by mixing the present compound with the aforementioned various types of pharmaceuticals and filling the obtained mixture in a hard gelatin capsule or soft capsule.

Furthermore, the compound of the present invention may also be formulated into water- or oil-type suspension, solution, syrup, and elixir, by common methods, using the aforementioned various types of additives for liquid preparations, such as a solvent, an extender, an isotonizing agent, a solubilizer, an emulsifier, a suspending agent, or a thickener.

An injection may be prepared by common methods, using pharmaceutical additives for liquid preparations including: diluents such as water, ethyl alcohol, Macrogol, propylene glycol, citric acid, acetic acid, phosphoric acid, lactic acid, sodium lactate, sulfuric acid, sodium hydroxide; pH adjusters and buffers, such as sodium citrate, sodium acetate, or sodium phosphate; stabilizers such as sodium pyrosulfite, ethylenediaminetetraacetic acid, thioglycolic acid, or thiolactic acid; isotonizing agents such as common salts, glucose, mannitol, or glycerin; solubilizers such as carboxymethylcellulose sodium, propylene glycol, sodium benzoate, benzyl benzoate, urethane, ethanolamine, or glycerin; soothing agents such as calcium gluconate, chlorobutanol, glucose, or benzyl alcohol; and local anesthetics.

An eyedrop may be prepared according to common methods by appropriately mixing the compound of the present invention with preservatives such as chlorobutanol, sodium dehydroacetate, benzalkonium chloride, cetyl pyridinium chloride, phenethyl alcohol, methyl parahydroxybenzoate, or benzethonium chloride; buffers such as borax, boric acid, or potassium dihydrogen phosphate; thickeners such as methylcellulose, hydroxyethylcellulose, carboxymethylcellulose, hydroxypropylmethylcellulose, polyvinyl alcohol, carboxymethylcellulose sodium, or chondroitin sulfate; solubilizers such as polysorbate 80 or polyoxyethylene hardened caster oil 60; stabilizers such as edetate sodium or sodium bisulfite; or isotonizing agents such as sodium chloride, potassium chloride, or glycerin.

A method for administration of the aforementioned preparations is not particularly limited. It is determined as appropriate, depending on the form of a preparation, the age of a patient, the sex thereof, and the degree of the symptoms of a patient, and other conditions.

The dosage of the active ingredient of the preparation of the present invention is selected as appropriate, depending on the usage, the age of a patient, the sex thereof, the form of disease, and other conditions. In general, the present preparation may be administered at a dosage between 0.1 and 500 mg per adult per day, once or divided over several administrations.

EXAMPLES

The present invention will be described in the following test example, production examples, and formulation examples. However, these examples are not intended to limit the scope of the present invention. The mixing ratios of eluents in production examples are all represented by volume ratios. The carriers used in column chromatography are B.W. silica gel, BW-127ZH, and FL-100DX (manufactured by Fuji Silysia Chemical Ltd.).

Test Example 1

Protecting Effect of Retinal Nerve in Rat Retinal Ischemia Reperfusion Model (a) Preparation of Retinal Ischemia Reperfusion Model A rat retinal ischemia reperfusion model was prepared by a partially modified method of Steven Roth et al. (Experimental Eye Research, Vol. 65, pp. 771-779, 1997).

As experimental animals, SD rats (SPF, 9-week-old, male, approximately 300 g of body weight) were used. Such rats were anesthetized with halothane (introduction: 4%; retention: 2%; gas composition: 70% air+30% oxygen; gas flow rate: 2 L/min). The rat was placed on a fixing plate with the left body side upward. The skin located between the external acoustic foramen and the external canthus on the left side was incised, and the skin-incised portion was held with a hook. The temporal muscle was burned out with a bipolar coagulator (output: 4.5 W), and it was detached from the cranial bone and the mandibular arch. Thereafter, the optic nerve was detached under an operation microscope, and the central retinal blood vessel with the thus obtained optic nerve was tied up with a silk thread to such an extent that the silk thread did not damage the optic nerve, and thereafter, the silk thread was fixed with a vascular clip. During ischemia for 30 minutes, the incised portion of the rat was closed, and the rat was then placed in a cage without undergoing anesthesia, so that it was allowed to move freely. 30 minutes later, the vascular clip and the silk thread were removed under halothane anesthesia again, so that the blood was allowed to flow again. Thereafter, the incised portion was sutured. In order to prevent the operated eye (left eye) from infection, ofloxacin eye ointment was applied thereto, and the eyelid was sutured in order to prevent the cornea from being dried.

(b) Administration of Test Compound

A test compound dissolved in distilled water was orally administered at an amount of 10 mg/kg to the rat from 2 days after retinal ischemia reperfusion, twice a day, for 14 days. In addition, distilled water was orally administered to a control group in the same manner described above.

(c) Electroretinogram (ERG) Measurement

ERG was measured in accordance with the method of Kawakami et al. (*Gifu-dai Iki*, Vol. 48, pp. 166-175, 2000). That is to say, after adaptation to darkness for approximately 1 hour, a mixed solution consisting of 66 mg/kg ketamine hydrochloride and 5 mg/kg xylazine hydrochloride was intramuscularly injected into the muscle of thigh of the rat for anesthesia under red light. Thereafter, the rat was held on brain stereotaxis apparatus, and it was further anesthetized by eyedrop with 0.4% oxybuprocaine hydrochloride. Thereafter, contact lens electrode for ERG was applied thereto. At that time, a droplet of adjuvant used for application of special contact lens to the cornea was added dropwise to the portion between the electrode and the cornea, so that they were allowed to closely contact with each other. A ground electrode was implanted into the skin of the lower extremity. For photic stimulation, single-shot white light discharge flashing was applied by full light emission with a stroboscope (stimulation frequency: 0.017 Hz). Such a stroboscope was placed at a position of 10 cm from the anterior surface of cornea of the rat. Electric signals generated as a result of the photic stimulation were added together twice and then averaged using reaction adding/histogram analyzing apparatus. The obtained waveform was swept on a memory oscilloscope and then recorded by a thermal array recorder. ERG measurement was carried out on each eye. Since ERG was indicated with the population spike of wave (a) and wave (b), the amplitude value of ERG was defined as a value from the bottom of the wave (a) to the vertex of the wave (b). Such ERG measurement was carried out also on a normal control eye of the same individual. ERG of the ischemic eye was evaluated as a ratio to the value of normal control eye. ERG was measured after adaptation to darkness at 2 days after retinal ischemia reperfusion, and at approximately 1 hour after the final administration.

(d) Results

The ratio of the ERG amplitude value of the ischemic eye to the normal control eye was 35% in the control group, to which distilled water had been administered. In contrast, the same above ratio was 65% in the group, to which 1-(3-(2-(1-benzothiophene-5-yl)ethoxy)propyl)-3-azetidinol maleate.

Production Example 1

Production of 1-(2-(2-(1-benzothiophene-5-yl)ethoxy)ethyl)-3-azetidinol (1) 1.20 g of 2-(2-(1-benzothiophene-5-yl)ethoxy)acetic acid was dissolved in 12 ml of methylene chloride. Thereafter, 2.3 ml of triethylamine and 0.38 g of imidazole were added to the obtained solution, and the mixture was then cooled to 5° C. Thereafter, 0.41 ml of thionyl chloride was added dropwise thereto, and the obtained mixture was stirred at the same above temperature for 1 hour. The reaction mixture was cooled to −60° C., and thereafter, 0.82 ml of triethylamine and 0.72 g of 3-azetidinol hydrochloride were added thereto. The mixture was stirred at the same above temperature for 1 hour and then at a room temperature for 1.5 hours. Thereafter, water was added to the reaction mixture, and the pH thereof was adjusted to pH 1.0 by addition of 6 mol/l hydrochloric acid. Thereafter, an organic layer was separated. The organic layer was washed with a saturated saline solution and then dried over anhydrous magnesium sulfate. The solvent was distilled away under a reduced pressure, so as to obtain a yellow oil product, 2-(2-(1-benzothiophene-5-yl)ethoxy)-1-(3-hydroxy-1-azetidinyl)-1-ethanone.

(2) The above 2-(2-(1-benzothiophene-5-yl)ethoxy)-1-(3-hydroxy-1-azetidinyl)-1-ethanone was dissolved in 12 ml of tetrahydrofuran, and the obtained solution was cooled to 5° C. Thereafter, 12.7 ml of a tetrahydrofuran solution containing a 1 mol/l borane-tetrahydrofuran complex was added dropwise thereto, and the obtained mixture was stirred at a room temperature for 17 hours. Thereafter, 10 ml of acetone was added to the reaction mixture, and the obtained mixture was then stirred for 30 minutes. Thereafter, 6.0 ml of 6 mol/l hydrochloric acid was added thereto, followed by heating to reflux for 2 hours. The reaction solution was cooled, and water and ethyl acetate were added to the reaction mixture. The pH thereof was adjusted to pH 13 by addition of a 2 mol/l aqueous sodium hydroxide solution, and an organic layer was then separated. The organic layer was washed with a saturated saline solution and then dried over anhydrous magnesium sulfate. The solvent was distilled away under a reduced pressure, so as to obtain 1.13 g of a yellow oil product, 1-(2-(2-(1-benzothiophene-5-yl)ethoxy)ethyl)-3-azetidinol.

IR (neat) cm$^{-1}$: 3378, 2943, 1438, 1198, 1119, 703

NMR (CDCl$_3$) δppm: 2.66 (2H, t, J=6 Hz), 2.9-3.1 (2H, m), 2.99 (2H, t, J=7 Hz), 3.46 (2H, t, J=6 Hz), 3.6-3.7 (2H, m), 3.67 (2H, t, J=7 Hz), 4.41 (1H, qn, J=6 Hz), 7.20 (1H, dd, J=2, 8 Hz), 7.27 (1H, d, J=5 Hz), 7.41 (1H, d, J=5 Hz), 7.66 (1H, d, J=2 Hz), 7.78 (1H, d, J=8 Hz)

Production Example 2

Production of 1-(2-(2-(1-benzothiophene-5-yl)ethoxy)ethyl)-3-azetidinol hydrochloride 1.03 g of 1-(2-(2-(1-benzothiophene-5-yl)ethoxy)ethyl)-3-azetidinol was dissolved in 4.2 ml of ethyl acetate. Thereafter, 0.86 ml of an ethyl acetate solution containing 4.76 mol/l dry hydrogen chloride was added to the obtained solution, and the obtained mixture was stirred at a room temperature for 1 hour, and then at 5° C. for 1 hour. Thereafter, precipitated crystals were collected by filtration, washed with ethyl acetate, and then dried, so as to obtain 0.98 g of 1-(2-(2-(1-benzothiophene-5-yl)ethoxy)ethyl)-3-azetidinol hydrochloride.

Melting point: 101° C. to 102° C.

IR (KBr) cm$^{-1}$: 3132, 2952, 1423, 1340, 1158, 814, 701

NMR (CDCl$_3$) δppm: 2.97 (2H, t, J=7 Hz), 3.2-3.3 (2H, m), 3.69 (2H, t, J=7 Hz), 3.6-3.8 (2H, m), 3.9-4.1 (2H, m), 4.2-4.4 (2H, m), 4.6-4.8 (1H, m), 7.18 (1H, dd, J=1, 8 Hz), 7.29 (1H, d, J=5 Hz), 7.41 (1H, d, J=5 Hz), 7.65 (1H, d, J=1 Hz), 7.78 (1H, d, J=8 Hz)

Production Example 3

Production of 1-(3-(2-(1-benzothiophene-6-yl)ethoxy)propyl)-3-azetidinol 1.00 g of 6-(2-(3-chloropropoxy)ethyl)-1-benzothiophene was dissolved in 5 ml of dimethyl sulfoxide. Thereafter, 0.86 g of 3-azetidinol hydrochloride and 1.63 g of potassium carbonate were added to the obtained solution, and the obtained mixture was stirred at 75° C. for 2.5 hours, and then at 95° C. for 1.5 hours. Thereafter, the reaction solution was cooled, and thereafter, water and ethyl acetate were added to the reaction mixture. The pH of the obtained mixture was adjusted to pH 1 by addition of 6 mol/l hydrochloric acid, and a water layer was then separated. Ethyl acetate was added to the water layer, and the pH of the obtained mixture was adjusted to pH 10 by addition of a 2 mol/l aqueous sodium hydroxide solution, followed by separation of an organic layer. The organic layer was successively washed with water and a saturated saline solution, and then dried over anhydrous magnesium sulfate. Thereafter, the solvent was distilled away under a reduced pressure. The residue was purified by column chromatography (eluent; chloroform:methanol=30:1 to 5:1), so as to obtain 0.28 g of an achromatic oil product, 1-(3-(2-(1-benzothiophene-6-yl)ethoxy)propyl)-3-azetidinol.

IR (neat) cm$^{-1}$: 3398, 2940, 2867, 1197, 1107, 820, 757

NMR (CDCl$_3$) δppm: 1.60 (2H, qn, J=7 Hz), 2.45 (2H, t, J=7 Hz), 2.7-2.8 (2H, m), 2.99 (2H, t, J=7 Hz), 3.45 (2H, t, J=7 Hz), 3.5-3.6 (2H, m), 3.66 (2H, t, J=7 Hz), 4.37 (1H, qn, J=6 Hz), 7.23 (1H, dd, J=1, 8 Hz), 7.29 (1H, d, J=5 Hz), 7.37 (1H, d, J=5 Hz), 7.73 (1H, d, J=1 Hz), 7.74 (1H, d, J=8 Hz)

Production Example 4

Production of 1-(3-(2-(1-benzothiophene-6-yl)ethoxy)propyl)-3-azetidinol hydrochloride 0.28 g of 1-(3-(2-(1-benzothiophene-6-yl)ethoxy)propyl)-3-azetidinol was dissolved in 3.0 ml of ethyl acetate. Thereafter, 0.35 ml of an ethyl acetate solution containing 3.25 mol/l dry hydrogen chloride was added to the obtained solution, and the obtained mixture was stirred at a room temperature for 1 hour. Subsequently, the solvent was distilled away under a reduced pressure, so as to obtain 0.30 g of a light yellow oil product, 1-(3-(2-(1-benzothiophene-6-yl)ethoxy)propyl)-3-azetidinol hydrochloride.

IR (neat) cm$^{-1}$: 3264, 2866, 2596, 1398, 1109, 1048, 821

NMR (CDCl$_3$) δppm: 1.81 (2H, qn, J=6 Hz), 2.92 (2H, t, J=6 Hz), 2.98 (2H, t, J=6 Hz), 3.46 (2H, t, J=6 Hz), 3.68 (2H, t, J=6 Hz), 3.8-3.9 (2H, m), 3.8-4.0 (2H, m), 4.4-4.6 (1H, m), 7.23 (1H, dd, J=1, 8 Hz), 7.31 (1H, d, J=5 Hz), 7.39 (1H, d, J=5 Hz), 7.74 (1H, d, J=1 Hz), 7.76 (1H, d, J=8 Hz)

Production Example 5

Production of 1-(3-(2-(1-benzothiophene-2-yl)ethoxy)propyl)-3-azetidinol

An achromatic oil product, 1-(3-(2-(1-benzothiophene-2-yl)ethoxy)propyl)-3-azetidinol was obtained in the same manner as in Production Example 3.

IR (neat) cm$^{-1}$: 3366, 2942, 2856, 1458, 1436, 1113, 750

NMR (CDCl$_3$) δppm: 1.64 (2H, qn=7 Hz), 2.49 (2H, t, J=7 Hz), 2.7-2.8 (2H, m), 3.15 (2H, t, J=7 Hz), 3.50 (2H, t, J=7 Hz), 3.5-3.7 (2H, m), 3.71 (2H, t, J=7 Hz), 4.3-4.4 (1H, m), 7.06 (1H, s), 7.2-7.4 (2H, m), 7.67 (1H, dd, J=1, 7 Hz), 7.77 (1H, dd, J=1, 7 Hz)

Production Example 6

Production of 1-(3-(2-(1-benzothiophene-2-yl)ethoxy)propyl)-3-azetidinol hydrochloride A light yellow oil product, 1-(3-(2-(1-benzothiophene-2-yl)ethoxy)propyl)-3-azetidinol hydrochloride was obtained in the same manner as in Production Example 4.

IR (neat) cm$^{-1}$: 3290, 2868, 1457, 1436, 1113, 751

NMR (CDCl$_3$) δppm: 1.83 (2H, qn, J=6 Hz), 2.91 (2H, t, J=6 Hz), 3.16 (2H, t, J=6 Hz), 3.52 (2H, t, J=6 Hz), 3.74 (2H, t, J=6 Hz), 3.7-3.8 (2H, m), 3.7-3.9 (2H, m), 4.3-4.5 (1H, m), 7.09 (1H, s), 7.27 (1H, dt, J=1, 8 Hz), 7.33 (1H, dt, J=1, 8 Hz), 7.69 (1H, dd, J=1, 8 Hz), 7.78 (1H, dd, J=1, 8 Hz)

Production Example 7

Production of 1-(3-(2-(1-benzothiophene-7-yl)ethoxy)propyl)-3-azetidinol

An achromatic oil product, 1-(3-(2-(1-benzothiophene-7-yl)ethoxy)propyl)-3-azetidinol was obtained in the same manner as in Production Example 3.

IR (neat) cm$^{-1}$: 3386, 2942, 2856, 1458, 1105, 796, 755, 700

NMR (CDCl$_3$) δppm: 1.61 (2H, qn, J=7 Hz), 2.45 (2H, t, J=7 Hz), 2.7-2.8 (2H, m), 3.17 (2H, t, J=7 Hz), 3.48 (2H, t, J=7 Hz), 3.5-3.7 (2H, m), 3.79 (2H, t, J=7 Hz), 4.3-4.5 (1H, m), 7.20 (1H, dd, J=1, 8 Hz), 7.32 (1H, t, J=8 Hz), 7.36 (1H, d, J=5 Hz), 7.43 (1H, d, J=5 Hz), 7.70 (1H, dd, J=1, 8 Hz)

Production Example 8

Production of 1-(3-(2-(1-benzothiophene-7-yl)ethoxy)propyl)-3-azetidinol hydrochloride An achromatic crystal, 1-(3-(2-(1-benzothiophene-7-yl)ethoxy)propyl)-3-azetidinol hydrochloride was obtained in the same manner as in Production Example 2.

Melting point: 105° C. to 106° C.

IR (KBr) cm$^{-1}$: 3252, 2806, 2620, 1398, 1130, 1106, 811, 708

NMR (CDCl$_3$) δppm: 1.82 (2H, qn, J=6 Hz), 2.8-3.0 (2H, m), 3.16 (2H, t, J=6 Hz), 3.47 (2H, t, J=6 Hz), 3.83 (2H, t, J=6 Hz), 3.7-4.1 (4H, m), 4.5-4.7 (1H, m), 7.21 (1H, d, J=8 Hz), 7.36 (1H, t, J=8 Hz), 7.38 (1H, d, J=5 Hz), 7.46 (1H, d, J=5 Hz), 7.73 (1H, d, J=8 Hz)

Production Example 9

Production of 1-(3-(2-(1-benzothiophene-5-yl)ethoxy)propyl)-3-azetidinol (1) 5.00 g of 3-(2-(1-benzothiophene-5-yl)ethoxy)propionic acid was suspended in 12.5 ml of toluene, and 0.1 ml of N,N-dimethylformamide was then added thereto. Thereafter, 1.68 ml of thionyl chloride was added dropwise thereto at 15° C., and the obtained mixture was then stirred at a room temperature for 1 hour. This reaction mixture was added dropwise to 25 ml of an aqueous solution containing 4.44 g of 3-hydroxyazetidine-1/2 tartrate and 3.76 g of sodium hydroxide at 10° C., and the mixture was then stirred at a room temperature for 1 hour. Thereafter, ethyl acetate was added to the reaction mixture, so as to separate an organic layer. The organic layer was successively washed with diluted hydrochloric acid and a saturated saline solution, and then dried over anhydrous magnesium sulfate. The solvent was then distilled away under a reduced pressure. The residue was purified by column chromatography (eluent; chloroform:acetone=3:1 to 1:1), and then crystallized from diisopropyl ether, so as to obtain 5.48 g of an achromatic crystal, 3-(2-(1-benzothiophene-5-yl)ethoxy)-1-(3-hydroxy-1-azetidinyl)-1-propanone.

IR (KBr) cm$^{-1}$: 3316, 2875, 1610, 1481, 1112, 992, 706

NMR (CDCl$_3$) δppm: 2.2-2.4 (2H, m), 2.98 (2H, t, J=7 Hz), 3.6-3.8 (5H, m), 3.8-4.0 (1H, m), 4.1-4.3 (2H, m), 4.4-4.4 (1H, m), 7.20 (1H, dd, J=1, 8 Hz), 7.28 (1H, dd, J=1, 5 Hz), 7.41 (1H, d, J=5 Hz), 7.6-7.7 (1H, m), 7.79 (1H, d, J=8 Hz)

(2) 5.00 g of 3-(2-(1-benzothiophene-5-yl)ethoxy)-1-(3-hydroxy-1-azetidinyl)-1-propanone was dissolved in 20 ml of tetrahydrofuran, and 1.09 g of sodium borohydride was then added thereto. Thereafter, 4.25 ml of a boron trifluoride-tetrahydrofuran complex was added dropwise thereto at 10° C., and the obtained mixture was then stirred at the same temperature for 1 hour and then at 40° C. for 3 hours. Thereafter, the reaction solution was cooled to 10° C. Thereafter, 30 ml of 6 mol/l hydrochloric acid was added dropwise to the reaction mixture, followed by reflux for 1 hour. After cooling, the solvent was concentrated under a reduced pressure, and ethyl acetate was added thereto. The pH of the mixture was adjusted to pH 9.4 by addition of a 20% aqueous sodium hydroxide solution, and an organic layer was then separated. The organic layer was successively washed with water and a saturated saline solution, and then dried over anhydrous magnesium sulfate. The solvent was then distilled away under a reduced pressure. The residue was purified by column chromatography (eluent; chloroform:methanol=20:1 to 10:1), and then crystallized from toluene-diisopropyl ether (1:3; 14 ml), so as to obtain 2.31 g of 1-(3-(2-(1-benzothiophene-5-yl)ethoxy)propyl)-3-azetidinol.

IR (KBr) cm$^{-1}$: 3095, 2944, 2769, 1361, 1191, 1098, 810, 709

NMR (CDCl$_3$) δppm: 1.61 (2H, qn, J=7 Hz), 2.45 (2H, t, J=7 Hz), 2.7-2.9 (2H, m), 2.99 (2H, t, J=7 Hz), 3.45 (2H, t, J=7 Hz), 3.5-3.6 (2H, m), 3.66 (2H, t, J=7 Hz), 4.3-4.4 (1H, m), 7.22 (1H, dd, J=1, 8 Hz), 7.28 (1H, d, J=5 Hz), 7.41 (1H, d, J=5 Hz), 7.67 (1H, d, J=1 Hz), 7.79 (1H, d, J=8 Hz)

Production Example 10

(A) Production of 1-(3-(2-(1-benzothiophene-5-yl)ethoxy)propyl)-3-azetidinol hydrochloride An achromatic crystal, 1-(3-(2-(1-benzothiophene-5-yl)ethoxy)propyl)-3-azetidinol hydrochloride, was obtained in the same manner as in Production Example 2.

Melting point: 71° C. to 73° C.

IR (KBr) cm$^{-1}$: 3301, 2937, 2809, 2631, 1125, 1099, 818, 765, 710

NMR (CDCl$_3$) δppm: 1.8-1.9 (2H, m), 2.98 (2H, t, J=7 Hz), 2.9-3.1 (2H, m), 3.48 (2H, t, J=6 Hz), 3.69 (2H, t, J=7 Hz), 3.6-4.4 (4H, m), 4.5-4.7 (1H, m), 7.22 (1H, dd, J=1, 8 Hz), 7.31 (1H, d, J=5 Hz), 7.44 (1H, d, J=5 Hz), 7.68 (1H, d, J=1 Hz), 7.81 (1H, d, J=8 Hz)

(B) Production of 1-(3-(2-(1-benzothiophene-5-yl)ethoxy)propyl)-3-azetidinol 1/2 fumarate 5.00 g of 1-(3-(2-(1-benzothiophene-5-yl)ethoxy)propyl)-3-azetidinol was dissolved in 10.0 ml of ethanol, and the obtained solution was then heated to 70° C. Thereafter, 0.99 g of fumaric acid was added to the solution, and the obtained mixture was stirred for 30 minutes. Thereafter, 30.0 ml of ethyl acetate was added dropwise to the solution, and the obtained mixture was stirred at 60° C. for 15 minutes and then cooled to 5° C. over 1 hour. Thereafter, the solution was further stirred at the same above temperature for 1 hour. Thereafter, precipitated crystals were collected by filtration and were then washed with ethyl acetate, followed by drying, so as to obtain 5.83 g of an achromatic crystal, 1-(3-(2-(1-benzothiophene-5-yl)ethoxy)propyl)-3-azetidinol 1/2 fumarate.

IR (KBr) cm$^{-1}$: 3258, 2936, 2862, 1578, 1360, 1114, 1109, 707, 665

NMR (DMSO-d$_6$) δppm: 1.5-1.6 (2H, m), 2.60 (2H, t, J=7 Hz), 2.91 (2H, t, J=7 Hz), 2.9-3.1 (2H, m), 3.39 (2H, t, J=7 Hz), 3.60 (2H, t, J=7 Hz), 3.6-3.8 (2H, m), 4.1-4.3 (1H, m), 6.50 (1H, s), 7.25 (1H, dd, J=1, 8 Hz), 7.39 (1H, d, J=5 Hz), 7.72 (1H, d, J=5 Hz), 7.73 (1H, d, J=1 Hz), 7.89 (1H, d, J=8 Hz)

(C) Production of 1-(3-(2-(1-benzothiophene-5-yl)ethoxy)propyl)-3-azetidinol maleate 8.00 g of 1-(3-(2-(1-benzothiophene-5-yl)ethoxy)propyl)-3-azetidinol was dissolved in 56 ml of acetone. Thereafter, 3.19 g of maleic acid was added thereto, and the obtained mixture was heated to 60° C. for dissolution. The reaction mixture was gradually cooled, and it was then stirred at 5° C. for 30 minutes. Thereafter, precipitated crystals were collected by filtration, so as to obtain 9.89 g of an achromatic crystal, 1-(3-(2-(1-benzothiophene-5-yl)ethoxy)propyl)-3-azetidinol maleate.

NMR (DMSO-d$_6$) δppm: 1.6-1.8 (2H, m), 2.93 (2H, t, J=7 Hz), 3.13 (2H, t, J=7 Hz), 3.43 (2H, t, J=6 Hz), 3.63 (2H, t, J=7 Hz), 3.7-3.9 (2H, m), 4.1-4.3 (2H, m), 4.4-4.5 (1H, m), 6.04 (2H, s), 7.26 (1H, dd, J=1, 8 Hz), 7.40 (1H, d, J=5 Hz), 7.7-7.8 (1H, m), 7.74 (1H, d, J=5 Hz), 7.92 (1H, d, J=8 Hz)

Production Example 11

Production of 1-(3-(2-(1-benzothiophene-4-yl)ethoxy)propyl)-3-azetidinol

An achromatic oil product, 1-(3-(2-(1-benzothiophene-4-yl)ethoxy)propyl)-3-azetidinol was obtained in the same manner as in Production Example 3.

IR (neat) cm$^{-1}$: 3368, 2946, 2856, 1457, 1107, 759

NMR (CDCl$_3$) δppm: 1.60 (2H, qn, J=7 Hz), 2.44 (2H, t, J=7 Hz), 2.7-2.9 (2H, m), 3.22 (2H, t, J=7 Hz), 3.45 (2H, t, J=7 Hz), 3.5-3.6 (2H, m), 3.70 (2H, t, J=7 Hz), 4.3-4.5 (1H, m), 7.19 (1H, d, J=7 Hz), 7.28 (1H, t, J=7 Hz), 7.44 (1H, d, J=6 Hz), 7.46 (1H, d, J=6 Hz), 7.76 (1H, d, J=7 Hz)

Production Example 12

Production of 1-(3-(2-(1-benzothiophene-4-yl)ethoxy)propyl)-3-azetidinol hydrochloride A light yellow oil product, 1-(3-(2-(1-benzothiophene-4-yl)ethoxy)propyl)-3-azetidinol hydrochloride was obtained in the same manner as in Production Example 4.

IR (neat) cm$^{-1}$: 3302, 2966, 2877, 2594, 1412, 1108, 766

NMR (CDCl$_3$) δppm: 1.78 (2H, qn, J=6 Hz), 2.82 (2H, t, J=7 Hz), 3.21 (2H, t, J=6 Hz), 3.43 (2H, t, J=6 Hz), 3.73 (2H, t, J=6 Hz), 3.7-3.9 (2H, m), 3.8-4.0 (2H, m), 4.5-4.7 (1H, m), 7.21 (1H, d, J=7 Hz), 7.30 (1H, t, J=7 Hz), 7.49 (2H, s), 7.78 (1H, d, J=7 Hz)

Production Example 13

Production of 1-(3-(2-(1-benzothiophene-3-yl)ethoxy)propyl)-3-azetidinol 1.00 g of 3-(2-(3-chloropropoxy)ethyl)-1-benzothiophene was dissolved in 5 ml of dimethyl sulfoxide. Thereafter, 1.10 g of 3-azetidinol trifluoroacetate and 1.63 g of potassium carbonate were added to the obtained solution, and the mixture was then stirred at 70° C. for 2 hours. After cooling, water and ethyl acetate were added to the reaction mixture. The pH of the mixture was adjusted to pH 1 by addition of 6 mol/l hydrochloric acid, and a water layer was then separated. Ethyl acetate was added to the water layer, and the pH of the obtained mixture was adjusted to pH 10 by addition of a 2 mol/l aqueous sodium hydroxide solution, followed by separation of an organic layer. The organic layer was successively washed with water and a saturated saline solution, and then dried over anhydrous magnesium sulfate. Thereafter, the solvent was distilled away under a reduced pressure. The residue was purified by column chromatography (eluent; chloroform: methanol=30:1 to 10:1), so as to obtain 0.55 g of an achromatic oil product, 1-(3-(2-(1-benzothiophene-3-yl)ethoxy)propyl)-3-azetidinol.

IR (neat) cm$^{-1}$: 3368, 2942, 2845, 1427, 1191, 1109, 759

NMR (CDCl$_3$) δppm: 1.62 (2H, qn, J=7 Hz), 2.47 (2H, t, J=7 Hz), 2.7-2.9 (2H, m), 3.11 (2H, t, J=7 Hz), 3.48 (2H, t, J=6 Hz), 3.5-3.7 (2H, m), 3.74 (2H, t, J=7 Hz), 4.3-4.5 (1H, m), 7.18 (1H, s), 7.33 (1H, dt, J=1, 7 Hz), 7.39 (1H, dt, J=1, 7 Hz), 7.77 (1H, dd, J=1, 7 Hz), 7.86 (1H, dd, J=1, 7 Hz)

Production Example 14

Production of 1-(3-(2-(1-benzothiophene-3-yl)ethoxy)propyl)-3-azetidinol hydrochloride A light yellow oil product, 1-(3-(2-(1-benzothiophene-3-yl)ethoxy)propyl)-3-azetidinol hydrochloride was obtained in the same manner as in Production Example 4.

IR (neat) cm$^{-1}$: 3284, 2966, 2596, 1428, 1112, 1049, 765, 734

NMR (CDCl$_3$) δppm: 1.83 (2H, qn, J=6 Hz), 2.96 (2H, t, J=6 Hz), 3.12 (2H, t, J=6 Hz), 3.48 (2H, t, J=6 Hz), 3.76 (2H, t, J=6 Hz), 3.8-3.9 (2H, m), 3.9-4.1 (2H, m), 4.5-4.7 (1H, m), 7.21 (1H, s), 7.35 (1H, dt, J=1, 7 Hz), 7.40 (1H, dt, J=1, 7 Hz), 7.78 (1H, dd, J=1.7 Hz), 7.86 (1H, dd, J=1, 7 Hz)

Production Example 15

Production of N-(1-(3-(2-(1-benzothiophene-5-yl)ethoxy)propyl)-3-azetidinyl)acetamide 0.80 g of 5-(2-(3-chloropropoxy)ethyl)-1-benzothiophene was dissolved in 8 ml of N,N-dimethylformamide. Thereafter, 1.20 g of N-(3-azetidinyl)acetamide was added to the obtained solution, and the obtained mixture was stirred at 90° C. for 12 hours. After cooling, water and ethyl acetate were added to the reaction mixture, and an organic layer was separated. The organic layer was successively washed with water and a saturated saline solution, and then dried over anhydrous magnesium sulfate. Thereafter, the solvent was distilled away under a reduced pressure. The residue was purified by column chromatography (eluent; chloroform:methanol=7:1), so as to obtain 0.39 g of a light yellow oil product, N-(1-(3-(2-(1-benzothiophene-5-yl)ethoxy)propyl)-3-azetidinyl)acetamide.

IR (neat) cm$^{-1}$: 3276, 2941, 2860, 1654, 1559, 1111, 756, 703

NMR (CDCl$_3$) δppm: 1.59 (2H, qn, J=7 Hz), 1.97 (3H, s), 2.42 (2H, t, J=7 Hz), 2.7-2.9 (2H, m), 2, 98 (2H, t, J=7 Hz), 3.45 (2H, t, J=7 Hz), 3.4-3.6 (2H, m), 3.66 (2H, t, J=7 Hz), 4.4-4.5 (1H, m), 7.22 (1H, dd, J=1, 8 Hz), 7.29 (1H, d, J=5 Hz), 7.42 (1H, d, J=5 Hz), 7.67 (1H, d, J=1 Hz), 7.80 (1H, d, J=8 Hz)

Production Example 16

Production of 1-(2-(2-(1-benzothiophene-6-yl)ethoxy)ethyl)-3-pyrrolidinol (1) 0.74 g of 2-(2-(1-benzothiophene-6-yl)ethoxy)acetic acid was dissolved in 7.4 ml of methylene chloride. Thereafter, 1.36 ml of triethylamine and 0.22 g of imidazole were added to the obtained solution. Subsequently, the mixture was cooled to 5° C. Thereafter, 0.24 ml of thionyl chloride was added dropwise thereto, and the obtained mixture was stirred at the same above temperature for 1 hour. After the reaction mixture was cooled to −50° C., 0.45 ml of triethylamine and 0.32 ml of 3-pyrrolidinol were added thereto. The mixture was stirred at the same above temperature for 1 hour and then at a room temperature for 1 hour. Thereafter, water was added to the reaction mixture, and an organic layer was separated. The organic layer was successively washed with 1 mol/l hydrochloric acid, then with a 2 mol/l aqueous sodium hydroxide solution, and then with a saturated saline solution. The resultant was then dried over anhydrous magnesium sulfate. Subsequently, the solvent was distilled away under a reduced pressure, so as to obtain a light yellow oil product, 2-(2-(1-benzothiophene-6-yl)ethoxy)-1-(3-hydroxy-1-pyrrolidinyl)-1-ethanone.

IR (neat) cm$^{-1}$: 3386, 2942, 1636, 1106, 758

(2) The above 2-(2-(1-benzothiophene-6-yl)ethoxy)-1-(3-hydroxy-1-pyrrolidinyl)-1-ethanone was dissolved in 7.4 ml of tetrahydrofuran. Thereafter, 7.4 ml of a tetrahydrofuran solution containing a 1 mol/l borane-tetrahydrofuran complex was added dropwise to the obtained solution while cooling on ice, and the obtained mixture was then stirred at a room temperature for 17 hours. Thereafter, 10 ml of acetone was added to the reaction mixture, and the obtained mixture was then stirred for 30 minutes. Thereafter, 1.5 ml of 6 mol/l hydrochloric acid was added thereto, and the obtained mixture was heated to reflux for 2 hours. After the reaction mixture was cooled, water and ethyl acetate were added thereto, and a water layer was separated. Thereafter, ethyl acetate was added to the water layer. The pH of the obtained mixture was adjusted to pH 9.5 by addition of a 2 mol/l aqueous sodium hydroxide solution, followed by separation of an organic layer. The organic layer was successively washed with water and a saturated saline solution, and then dried over anhydrous magnesium sulfate. Thereafter, the solvent was distilled away under a reduced pressure. The residue was purified by column chromatography (eluent; chloroform:methanol=30:1 to 20:1), so as to obtain 0.53 g of a yellow oil product, 1-(2-(2-(1-benzothiophene-6-yl)ethoxy)ethyl)-3-pyrrolidinol.

IR (neat) cm$^{-1}$: 3386, 2940, 2867, 1110, 820, 756

NMR (CDCl$_3$) δppm: 1.6-1.8 (1H, m), 2.0-2.2 (1H, m), 2.31 (1H, dt, J=7, 9 Hz), 2.53 (1H, dd, J=5, 10 Hz), 2.6-2.7 (3H, m), 2.85 (1H, dt, J=5, 9 Hz), 3.01 (2H, t, J=7 Hz), 3.58 (2H, t, J=6 Hz), 3.71 (2H, t, J=7 Hz), 4.2-4.3 (1H, m), 7.23 (1H, d, J=8 Hz), 7.29 (1H, d, J=5 Hz), 7.37 (1H, d, J=5 Hz), 7.73 (1H, d, J=8 Hz), 7.73 (1H, s)

Production Example 17

Production of 1-(2-(2-(1-benzothiophene-6-yl)ethoxy)ethyl)-3-pyrrolidinol oxalate 0.48 g of 1-(2-(2-(1-benzothiophene-6-yl)ethoxy)ethyl)-3-pyrrolidinol was dissolved in 2.0 ml of ethyl acetate. Thereafter, 2.8 ml of an ethyl acetate solution containing 0.15 g of oxalic acid was added to the obtained solution, and the mixture was stirred at a room temperature for 1 hour and then at 5° C. for 1 hour. Thereafter, precipitated crystals were collected by filtration and were then washed with ethyl acetate, followed by drying, so as to obtain 0.42 g of an achromatic crystal, 1-(2-(2-(1-benzothiophene-6-yl)ethoxy)ethyl)-3-pyrrolidinol oxalate.

IR (KBr) cm$^{-1}$: 3384, 2862, 2687, 1717, 1636, 1400, 1200, 1114, 720

NMR (DMSO-d$_6$) δppm: 1.7-1.8 (1H, m), 1.9-2.1 (1H, m), 2.96 (2H, t, J=7 Hz), 3.0-3.2 (1H, m), 3.1-3.4 (5H, m), 3.6-3.8 (4H, m), 4.3-4.4 (1H, m), 7.29 (1H, d, J=8 Hz), 7.41 (1H, d, J=5 Hz), 7.68 (1H, d, J=5 Hz), 7.80 (1H, d, J=8 Hz), 7.87 (1H, s)

Production Example 18

Production of 1-(2-(2-(1-benzothiophene-5-yl)ethoxy)ethyl)-3-pyrrolidinol 2-(2-(1-benzothiophene-5-yl)ethoxy)-1-(3-hydroxy-1-pyrrolidinyl)-1-ethanone was obtained in the same manner as in Production Example 16(1).

NMR (CDCl$_3$) δppm: 1.6-2.2 (2H, m), 2.9-4.0 (8H, m), 4.0-4.2 (2H, m), 4.2-4.5 (1H, m), 7.1-7.4 (2H, m), 7.42 (1H, d, J=5 Hz), 7.69 (1H, s), 7.79 (1H, d, J=8 Hz)

Subsequently, a light yellow oil product, 1-(2-(2-(1-benzothiophene-5-yl)ethoxy)ethyl)-3-pyrrolidinol was obtained in the same manner as in Production Example 16(2).

IR (neat) cm$^{-1}$: 3386, 2941, 2864, 1438, 1112, 755, 702

NMR (CDCl$_3$) δppm: 1.5-2.0 (1H, m), 2.0-2.9 (7H, m), 3.00 (2H, t, J=7 Hz), 3.58 (2H, t, J=6 Hz), 3.71 (2H, t, J=7 Hz), 4.2-4.4 (1H, m), 7.21 (1H, d, J=8 Hz), 7.28 (1H, d, J=5 Hz), 7.42 (1H, d, J=5 Hz), 7.67 (1H, s), 7.79 (1H, d, J=8 Hz)

Production Example 19

Production of 1-(2-(2-(1-benzothiophene-5-yl)ethoxy)ethyl)-3-pyrrolidinol oxalate An achromatic crystal, 1-(2-(2-(1-benzothiophene-5-yl)ethoxy)ethyl)-3-pyrrolidinol oxalate was obtained in the same manner as in Production Example 17.

IR (KBr) cm$^{-1}$: 3347, 2943, 2687, 1719, 1404, 1119, 720

NMR (CDCl$_3$) δppm: 1.7-2.2 (2H, m), 2.9-3.8 (6H, m), 2.94 (2H, t, J=6 Hz), 3.68 (4H, t, J=6 Hz), 4.2-4.5 (1H, m), 7.17 (1H, d, J=8 Hz), 7.26 (1H, d, J=5 Hz), 7.42 (1H, d, J=5 Hz), 7.62 (1H, s), 7.78 (1H, d, J=8 Hz)

Production Example 20

Production of 1-(2-(2-(1-benzothiophene-4-yl)ethoxy)ethyl)-3-pyrrolidinol

An oil product, 2-(2-(1-benzothiophene-4-yl)ethoxy)-1-(3-hydroxy-1-pyrrolidinyl)-1-ethanone was obtained in the same manner as in Production Example 16(1).

IR (neat) cm$^{-1}$: 3374, 2944, 1637, 1107, 761

Subsequently, a light yellow oil product, 1-(2-(2-(1-benzothiophene-4-yl)ethoxy)ethyl)-3-pyrrolidinol was obtained in the same manner as in Production Example 16(2).

IR (neat) cm$^{-1}$: 3376, 2939, 2867, 1452, 1413, 1111, 760

NMR (CDCl$_3$) δppm: 1.6-1.8 (1H, m), 2.1-2.2 (1H, m), 2.30 (1H, dt, J=6, 9 Hz), 2.53 (1H, dd, J=5, 10 Hz), 2.6-2.7 (3H, m), 2.85 (1H, dt, J=5, 9 Hz), 3.25 (2H, t, J=7 Hz), 3.58 (2H, t, J=6 Hz), 3.75 (2H, t, J=7 Hz), 4.2-4.4 (1H, m), 7.20 (1H, d, J=7 Hz), 7.27 (1H, t, J=7 Hz), 7.44 (1H, d, J=6 Hz), 7.46 (1H, d, J=6 Hz), 7.75 (1H, d, J=7 Hz)

Production Example 21

Production of 1-(2-(2-(1-benzothiophene-4-yl)ethoxy)ethyl)-3-pyrrolidinol hydrochloride 0.63 g of 1-(2-(2-(1-benzothiophene-4-yl)ethoxy)ethyl)-3-pyrrolidinol was dissolved in 5.0 ml of ethyl acetate. Thereafter, 0.80 ml of an ethyl acetate solution containing 3.25 mol/l dry hydrogen chloride was added to the obtained solution. The mixture was stirred at a room temperature for 1 hour and then at 5° C. for 1 hour. Thereafter, precipitated crystals were collected by filtration. The precipitated crystals were washed with ethyl acetate and then dried, so as to obtain 0.43 g of an achromatic crystal, 1-(2-(2-(1-benzothiophene-4-yl)ethoxy)ethyl)-3-pyrrolidinol hydrochloride.

IR (KBr) cm$^{-1}$: 3229, 2872, 2625, 1451, 1413, 1119, 771

NMR (DMSO-d$_6$) δppm: 1.7-2.2 (2H, m), 2.9-3.6 (6H, m), 3.22 (2H, t, J=7 Hz), 3.74 (4H, t, J=7 Hz), 4.3-4.4 (1H, m), 7.27 (1H, d, J=8 Hz), 7.30 (1H, t, J=8 Hz), 7.61 (1H, d, J=5 Hz), 7.77 (1H, d, J=5 Hz), 7.86 (1H, d, J=8 Hz)

Production Example 22

Production of 1-(2-(2-(1-benzothiophene-7-yl)ethoxy)ethyl)-3-pyrrolidinol

An oil product, 2-(2-(1-benzothiophene-7-yl)ethoxy)-1-(3-hydroxy-1-pyrrolidinyl)-1-ethanone was obtained in the same manner as in Example 16(1).

NMR (CDCl$_3$) δppm: 1.8-2.0 (2H, m), 3.1-3.3 (3H, m), 3.3-3.6 (3H, m), 3.8-4.0 (2H, m), 4.0-4.2 (2H, m), 4.3-4.5 (1H, m), 7.23 (1H, d, J=7 Hz), 7.3-7.4 (2H, m), 7.4-7.5 (1H, m), 7.6-7.8 (1H, m)

Subsequently, an achromatic oil product, 1-(2-(2-(1-benzothiophene-7-yl)ethoxy)ethyl)-3-pyrrolidinol was obtained in the same manner as in Example 16(2).

IR (neat) cm$^{-1}$: 3385, 2941, 2867, 1459, 1395, 1106, 795, 754, 701

NMR (CDCl$_3$) δppm: 1.6-1.8 (1H, m), 2.1-2.2 (1H, m), 2.30 (1H, dt, J=7, 9 Hz), 2.52 (1H, dd, J=5, 10 Hz), 2.6-2.7 (3H, m), 2.85 (1H, dt, J=5, 9 Hz), 3.19 (2H, t, J=7 Hz), 3.59 (2H, t, J=6 Hz), 3.84 (2H, t, J=7 Hz), 4.2-4.4 (1H, m), 7.20 (1H, d, J=8 Hz), 7.32 (1H, t, J=8 Hz), 7.35 (1H, d, J=5 Hz), 7.42 (1H, d, J=5 Hz), 7.69 (1H, d, J=8 Hz)

Production Example 23

Production of 1-(2-(2-(1-benzothiophene-7-yl)ethoxy)ethyl)-3-pyrrolidinol hydrochloride An achromatic crystal, 1-(2-(2-(1-benzothiophene-7-yl)ethoxy)ethyl)-3-pyrrolidinol hydrochloride was obtained in the same manner as in Production Example 21.

IR (KBr) cm$^{-1}$: 3283, 2938, 2706, 1395, 1358, 1125, 810, 720

NMR (DMSO-d$_6$) δppm: 1.7-2.2 (2H, m), 2.8-3.7 (6H, m), 3.12 (2H, t, J=7 Hz), 3.7-3.8 (2H, m), 3.82 (2H, t, J=7 Hz), 4.3-4.4 (1H, m), 7.29 (1H, d, J=7 Hz), 7.36 (1H, t, J=7 Hz), 7.49 (1H, d, J=5 Hz), 7.76 (1H, d, J=5 Hz), 7.77 (1H, d, J=7 Hz)

Production Example 24

Production of 1-(2-(2-(1-benzothiophene-2-yl)ethoxy)ethyl)-3-pyrrolidinol 2-(2-(1-benzothiophene-2-yl)ethoxy)-1-(3-hydroxy-1-pyrrolidinyl)-1-ethanone was obtained in the same manner as in Example 16(1).

NMR (CDCl$_3$) δppm: 1.8-2.0 (2H, m), 3.1-3.3 (3H, m), 3.3-3.7 (3H, m), 3.8-4.0 (2H, m), 4.1-4.2 (2H, m), 4.2-4.5 (1H, m), 7.10 (1H, s), 7.2-7.4 (2H, m), 7.6-7.7 (1H, m), 7.7-7.8 (1H, m)

Subsequently, a light yellow oil product, 1-(2-(2-(1-benzothiophene-2-yl)ethoxy)ethyl)-3-pyrrolidinol was obtained in the same manner as in Example 16(2).

IR (neat) cm$^{-1}$: 3396, 2939, 1458, 1438, 1113, 747, 727

NMR (CDCl$_3$) δppm: 1.6-1.8 (1H, m), 2.1-2.2 (1H, m), 2.34 (1H, dt, J=6, 9 Hz), 2.55 (1H, dd, J=5, 10 Hz), 2.6-2.8 (3H, m), 2.85 (1H, dt, J=5, 9 Hz), 3.18 (2H, dt, J=1, 7 Hz), 3.62 (2H, t, J=6 Hz), 3.77 (2H, t, J=7 Hz), 4.2-4.4 (1H, m), 7.07 (1H, s), 7.26 (1H, dt, J=1, 8 Hz), 7.31 (1H, dt, J=1, 8 Hz), 7.67 (1H, dd, J=1, 8 Hz), 7.76 (1H, dd, J=1, 8 Hz)

Production Example 25

Production of 1-(2-(2-(1-benzothiophene-2-yl)ethoxy)ethyl)-3-pyrrolidinol oxalate An achromatic crystal, 1-(2-(2-(1-benzothiophene-2-yl)ethoxy)ethyl)-3-pyrrolidinol oxalate was obtained in the same manner as in Production Example 17.

IR (KBr) cm$^{-1}$: 3432, 2871, 1716, 1436, 1127, 827, 760, 706

NMR (DMSO-d$_6$) δppm: 1.7-1.8 (1H, m), 1.9-2.2 (1H, m), 3.0-3.4 (8H, m), 3.73 (4H, t, J=6 Hz), 4.2-4.4 (1H, m), 7.23 (1H, s), 7.28 (1H, t, J=7 Hz), 7.33 (1H, t, J=7 Hz), 7.74 (1H, d, J=7 Hz), 7.87 (1H, d, J=7 Hz)

Production Example 26

Production of 1-(2-(2-(1-benzothiophene-3-yl)ethoxy)ethyl)-3-pyrrolidinol

An oil product, 2-(2-(1-benzothiophene-3-yl)ethoxy)-1-(3-hydroxy-1-pyrrolidinyl)-1-ethanone was obtained in the same manner as in Example 16(1).

NMR (CDCl$_3$) δppm: 1.8-1.9 (1H, m), 1.9-2.0 (1H, m), 3.1-3.6 (6H, m), 3.8-4.0 (2H, m), 4.09 (1H, s), 4.13 (1H, s), 4.3-4.5 (1H, m), 7.26 (1H, s), 7.3-7.4 (2H, m), 7.77 (1H, d, J=8 Hz), 7.85 (1H, d, J=8 Hz)

Subsequently, a light yellow oil product, 1-(2-(2-(1-benzothiophene-3-yl)ethoxy)ethyl)-3-pyrrolidinol was obtained in the same manner as in Example 16(2).

IR (neat) cm$^{-1}$: 3388, 2934, 1426, 1112, 761, 733

NMR (CDCl$_3$) δppm: 1.6-1.8 (1H, m), 2.1-2.2 (1H, m), 2.33 (1H, dt, J=6, 9 Hz), 2.56 (1H, dd, J=5, 10 Hz), 2.6-2.8 (3H, m), 2.87 (1H, dt, J=5, 9 Hz), 3.14 (2H, dt, J=1, 7 Hz), 3.61 (2H, t, J=6 Hz), 3.80 (2H, t, J=7 Hz), 4.3-4.4 (1H, m), 7.20 (1H, s), 7.34 (1H, dt, J=1, 7 Hz), 7.38 (1H, dt, J=1, 7 Hz), 7.77 (1H, dd, J=1, 7 Hz), 7.85 (1H, dd, J=1, 7 Hz)

Production Example 27

Production of 1-(2-(2-(1-benzothiophene-3-yl)ethoxy)ethyl)-3-pyrrolidinol oxalate An achromatic crystal, 1-(2-(2-(1-benzothiophene-3-yl)ethoxy)ethyl)-3-pyrrolidinol oxalate was obtained in the same manner as in Production Example 17.

IR (KBr) cm$^{-1}$: 3363, 2922, 2691, 1718, 1636, 1427, 1404, 1119, 767, 721

NMR (DMSO-d$_6$) δμm: 1.7-1.8 (1H, m), 2.0-2.2 (1H, m), 3.10 (2H, t, J=7 Hz), 3.1-3.4 (6H, m), 3.72 (2H, t, J=5 Hz), 3.78 (2H, t, J=7 Hz), 4.3-4.4 (1H, m), 7.37 (1H, t, J=8 Hz), 7.42 (1H, t, J=8 Hz), 7.51 (1H, s), 7.85 (1H, d, J=8 Hz), 7.98 (1H, d, J=8 Hz)

Production Example 28

Production of 1-(2-(2-(1-naphthyl)ethoxy)ethyl)-3-pyrrolidinol

A yellow oil product, 2-(2-(1-naphthyl)ethoxy)-1-(3-hydroxy-1-pyrrolidinyl)-1-ethanone was obtained in the same manner as in Production Example 16(1).

IR (neat) cm$^{-1}$: 3392, 2946, 1645, 1133, 800, 779

Subsequently, a light yellow oil product, 1-(2-(2-(1-naphthyl)ethoxy)ethyl)-3-pyrrolidinol was obtained in the same manner as in Production Example 16(2).

IR (neat) cm$^{-1}$: 3395, 2944, 1107, 778

NMR (CDCl$_3$) δppm: 1.5-1.9 (1H, m), 2.0-2.5 (3H, m), 2.5-3.0 (4H, m), 3.37 (2H, t, J=7 Hz), 3.59 (2H, t, J=6 Hz), 3.80 (2H, t, J=7 Hz), 4.2-4.4 (1H, m), 7.4-7.6 (4H, m), 7.6-8.0 (2H, m), 8.0-8.2 (1H, m)

Production Example 29

Production of 1-(2-(2-(1-naphthyl)ethoxy)ethyl)-3-pyrrolidinol oxalate

An achromatic crystal, 1-(2-(2-(1-naphthyl)ethoxy)ethyl)-3-pyrrolidinol oxalate was obtained in the same manner as in Production Example 17.

IR (KBr) cm$^{-1}$: 3366, 1400, 1116, 780, 720

NMR (DMSO-d$_6$) δppm: 1.6-2.3 (2H, m), 2.7-3.5 (8H, m), 3.5-3.9 (4H, m), 4.2-4.5 (1H, m), 7.4-7.6 (4H, m), 7.7-8.0 (2H, m), 8.0-8.2 (1H, m)

Production Example 30

Production of (3S)-1-(2-(2-(1-benzothiophene-5-yl)ethoxy)ethyl)-3-pyrrolidinol

A light yellow oil product, 2-(2-(1-benzothiophene-5-yl)ethoxy)-1-((3S)-3-hydroxy-1-pyrrolidinol))-1-ethanone was obtained in the same manner as in Production Example 16(1).

Subsequently, a light yellow oil product, (3S)-1-(2-(2-(1-benzothiophene-5-yl)ethoxy)ethyl)-3-pyrrolidinol was obtained in the same manner as in Production Example 16(2).

IR (neat) cm$^{-1}$: 3386, 2936, 2867, 1438, 1111, 755, 702

NMR (CDCl$_3$) δppm: 1.5-2.0 (1H, m), 2.0-3.0 (5H, m), 2.66 (2H, t, J=6 Hz), 3.00 (2H, t, J=7 Hz), 3.58 (2H, t, J=6 Hz), 3.71 (2H, t, J=7 Hz), 4.2-4.4 (1H, m), 7.21 (1H, d, J=8 Hz), 7.28 (1H, d, J=5 Hz), 7.42 (1H, d, J=5 Hz), 7.67 (1H, s), 7.79 (1H, d, J=8 Hz)

Production Example 31

Production of (3S)-1-(2-(2-(1-benzothiophene-5-yl)ethoxy)ethyl)-3-pyrrolidinol oxalate An achromatic crystal, (3S)-1-(2-(2-(1-benzothiophene-5-yl)ethoxy)ethyl)-3-pyrrolidinol oxalate was obtained in the same manner as in Production Example 17.
IR (KBr) cm$^{-1}$: 3366, 2941, 2867, 2686, 1718, 1701, 1404, 1114, 720
NMR (DMSO-d$_6$) δppm: 1.5-2.2 (2H, m), 2.8-3.5 (8H, m), 3.70 (4H, t, J=6 Hz), 4.2-4.5 (1H, m), 7.28 (1H, d, J=8 Hz), 7.40 (1H, d, J=5 Hz), 7.73 (1H, d, J=5 Hz), 7.76 (1H, s), 7.91 (1H, d, J=8 Hz)

Production Example 32

Production of (3R)-1-(2-(2-(1-benzothiophene-5-yl)ethoxy)ethyl)-3-pyrrolidinol

An achromatic crystal, 2-(2-(1-benzothiophene-5-yl)ethoxy)-1-((3R)-3-hydroxy-1-pyrrolidinyl))-1-ethanone was obtained in the same manner as in Production Example 16(1).
IR (KBr) cm$^{-1}$: 3408, 2937, 1637, 1137, 1108, 812, 703
Subsequently, a light yellow oil product, (3R)-1-(2-(2-(1-benzothiophene-5-yl)ethoxy)ethyl)-3-pyrrolidinol was obtained in the same manner as in Production Example 16(2).
IR (neat) cm$^{-1}$: 3373, 2940, 1438, 1111, 755, 702
NMR (CDCl$_3$) δppm: 1.5-2.0 (1H, m), 2.0-3.0 (5H, m), 2.68 (2H, t, J=6 Hz), 3.01 (2H, t, J=7 Hz), 3.59 (2H, t, J=6 Hz), 3.71 (2H, t, J=7 Hz), 4.2-4.4 (1H, m), 7.21 (1H, d, J=8 Hz), 7.28 (1H, d, J=5 Hz), 7.42 (1H, d, J=5 Hz), 7.67 (1H, s), 7.79 (1H, d, J=8 Hz)

Production Example 33

Production of (3R)-1-(2-(2-(1-benzothiophene-5-yl)ethoxy)ethyl)-3-pyrrolidinol oxalate An achromatic crystal, (3R)-1-(2-(2-(1-benzothiophene-5-yl)ethoxy)ethyl)-3-pyrrolidinol oxalate was obtained in the same manner as in Production Example 17.
IR (KBr) cm$^{-1}$: 3318, 2870, 1718, 1114, 720
NMR (DMSO-d$_6$) δppm: 1.5-2.2 (2H, m), 2.8-3.5 (8H, m), 3.70 (4H, t, J=6 Hz), 4.2-4.5 (1H, m), 7.28 (1H, d, J=8 Hz), 7.40 (1H, d, J=5 Hz), 7.73 (1H, d, J=5 Hz), 7.76 (1H, s), 7.91 (1H, d, J=8 Hz)

Production Example 34

Production of (3S)-1-(2-(2-(1-benzothiophene-6-yl)ethoxy)ethyl)-3-pyrrolidinol

An achromatic oil product, 2-(2-(1-benzothiophene-6-yl)ethoxy)-1-((3S)-3-hydroxy-1-pyrrolidinyl))-1-ethanone was obtained in the same manner as in Production Example 16(1).
IR (neat) cm$^{-1}$: 3385, 2944, 1637, 1133, 820, 699
Subsequently, an achromatic oil product, (3S)-1-(2-(2-(1-benzothiophene-6-yl)ethoxy)ethyl)-3-pyrrolidinol was obtained in the same manner as in Production Example 16(2).
IR (neat) cm$^{-1}$: 3385, 2940, 2867, 1110, 820, 757
NMR (CDCl$_3$) δ ppm: 1.6-1.8 (1H, m), 2.1-2.2 (1H, m), 2.32 (1H, dt, J=6, 9 Hz), 2.54 (1H, dd, J=5, 10 Hz), 2.6-2.7 (3H, m), 2.85 (1H, dt, J=5, 9 Hz), 3.01 (2H, t, J=7 Hz), 3.58 (2H, t, J=6 Hz), 3.71 (2H, t, J=7 Hz), 4.2-4.3 (1H, m), 7.23 (1H, d, J=8 Hz), 7.29 (1H, d, J=5 Hz), 7.37 (1H, d, J=5 Hz), 7.73 (1H, d, J=8 Hz), 7.74 (1H, s)

Production Example 35

Production of (3S)-1-(2-(2-(1-benzothiophene-6-yl)ethoxy)ethyl)-3-pyrrolidinol oxalate An achromatic crystal, (3S)-1-(2-(2-(1-benzothiophene-6-yl)ethoxy)ethyl)-3-pyrrolidinol oxalate was obtained in the same manner as in Production Example 17.
IR (KBr) cm$^{-1}$: 3364, 2938, 2692, 1718, 1400, 1201, 1114, 720
NMR (DMSO-d$_6$) δppm: 1.7-1.8 (1H, m), 1.9-2.1 (1H, m), 2.96 (2H, t, J=7 Hz), 3.0-3.1 (1H, m), 3.1-3.3 (5H, m), 3.70 (4H, t, J=7 Hz), 4.2-4.3 (1H, m), 7.29 (1H, d, J=8 Hz), 7.41 (1H, d, J=5 Hz), 7.68 (1H, d, J=5 Hz), 7.80 (1H, d, J=8 Hz), 7.87 (1H, s)

Production Example 36

Production of (3R)-1-(2-(2-(1-benzothiophene-6-yl)ethoxy)ethyl)-3-pyrrolidinol

An oil product, 2-(2-(1-benzothiophene-6-yl)ethoxy)-1-((3R)-3-hydroxy-1-pyrrolidinyl))-1-ethanone was obtained in the same manner as in Production Example 16(1).
IR (neat) cm$^{-1}$: 3386, 2940, 1637, 1107, 820, 758
Subsequently, an achromatic oil product, (3R)-1-(2-(2-(1-benzothiophene-6-yl)ethoxy)ethyl)-3-pyrrolidinol was obtained in the same manner as in Production Example 16(2).
IR (neat) cm$^{-1}$: 3385, 2940, 2867, 1110, 820, 757
NMR (CDCl$_3$) δppm: 1.6-1.8 (1H, m), 2.1-2.2 (1H, m), 2.32 (1H, dt, J=6, 9 Hz), 2.54 (1H, dd, J=5, 10 Hz), 2.6-2.7 (3H, m), 2.85 (1H, dt, J=5, 9 Hz), 3.01 (2H, t, J=7 Hz), 3.58 (2H, t, J=6 Hz), 3.71 (2H, t, J=7 Hz), 4.2-4.3 (1H, m), 7.23 (1H, d, J=8 Hz), 7.29 (1H, d, J=5 Hz), 7.37 (1H, d, J=5 Hz), 7.73 (1H, d, J=8 Hz), 7.74 (1H, s)

Production Example 37

Production of (3R)-1-(2-(2-(1-benzothiophene-6-yl)ethoxy)ethyl)-3-pyrrolidinol oxalate An achromatic crystal, (3R)-1-(2-(2-(1-benzothiophene-6-yl)ethoxy)ethyl)-3-pyrrolidinol oxalate was obtained in the same manner as in Production Example 17.
IR (KBr) cm$^{-1}$: 3364, 2938, 2688, 1718, 1400, 1201, 1114, 720
NMR (DMSO-d$_6$) δppm: 1.7-1.8 (1H, m), 1.9-2.1 (1H, m), 2.96 (2H, t, J=7 Hz), 3.0-3.1 (1H, m), 3.1-3.3 (5H, m), 3.70 (4H, t, J=7 Hz), 4.2-4.3 (1H, m), 7.29 (1H, d, J=8 Hz), 7.41 (1H, d, J=5 Hz), 7.68 (1H, d, J=5 Hz), 7.80 (1H, d, J=8 Hz), 7.87 (1H, s)

Production Example 38

Production of (3R)-1-(2-(2-(1-benzothiophene-3-yl)ethoxy)ethyl)-3-pyrrolidinol 2-(2-(1-benzothiophene-3-yl)ethoxy)-1-((3R)-3-hydroxy-1-pyrrolidinyl))-1-ethanone was obtained in the same manner as in Production Example 16(1).
NMR (CDCl$_3$) δppm: 1.8-1.9 (1H, m), 1.9-2.0 (1H, m), 3.1-3.4 (3H, m), 3.3-3.7 (3H, m), 3.8-4.0 (2H, m), 4.0-4.2

(2H, m), 4.3-4.5 (1H, m), 7.27 (½H, s), 7.28 (½H, s), 7.3-7.5 (2H, m), 7.7-7.8 (1H, m), 7.8-7.9 (1H, m)

Subsequently, a yellow oil product, (3R)-1-(2-(2-(1-benzothiophene-3-yl)ethoxy)ethyl)-3-pyrrolidinol was obtained in the same manner as in Production Example 16(2).

IR (neat) cm$^{-1}$: 3386, 2942, 1458, 1429, 1113, 759, 733

NMR (CDCl$_3$) δppm: 1.6-1.8 (1H, m), 2.1-2.2 (1H, m), 2.34 (1H, dt, J=6, 9 Hz), 2.55 (1H, dd, J=5, 10 Hz), 2.6-2.8 (3H, m), 2.85 (1H, dt, J=5, 9 Hz), 3.14 (2H, t, J=7 Hz), 3.61 (2H, t, J=6 Hz), 3.80 (2H, t, J=7 Hz), 4.2-4.4 (1H, m), 7.21 (1H, s), 7.34 (1H, dt, J=1, 7 Hz), 7.38 (1H, dt, J=1, 7 Hz), 7.76 (1H, dd, J=1, 7 Hz), 7.85 (1H, dd, J=1, 7 Hz)

Production Example 39

Production of (3R)-1-(2-(2-(1-benzothiophene-3-yl)ethoxy)ethyl)-3-pyrrolidinol hydrochloride 0.99 g of (3R)-1-(2-(2-(1-benzothiophene-3-yl)ethoxy)ethyl)-3-pyrrolidinol was dissolved in 5.0 ml of ethyl acetate. Thereafter, 1.10 ml of an ethyl acetate solution containing 3.25 mol/l dry hydrogen chloride was added to the obtained solution, and the obtained mixture was then stirred at a room temperature for 1 hour. Thereafter, the solvent was distilled away under a reduced pressure, so as to obtain 1.05 g of a light yellow oil product, (3R)-1-(2-(2-(1-benzothiophene-3-yl)ethoxy)ethyl)-3-pyrrolidinol hydrochloride.

IR (neat) cm$^{-1}$: 3368, 2946, 1560, 1430, 1121, 765, 734

NMR (CDCl$_3$) δppm: 1.9-2.1 (1H, m), 2.1-2.3 (1H, m), 2.8-3.0 (2H, m), 3.1-3.2 (4H, m), 3.29 (1H, d, J=12 Hz), 3.3-3.5 (1H, m), 3.8-3.9 (4H, m), 4.3-4.4 (1H, m), 7.24 (1H, s), 7.35 (1H, t, J=8 Hz), 7.40 (1H, t, J=8 Hz), 7.76 (1H, d, J=8 Hz), 7.86 (1H, d, J=8 Hz)

Production Example 40

Production of 1-(2-(2-(1-benzothiophene-5-yl)ethoxy)ethyl)-4-piperidinol

An oil product, 2-(2-(1-benzothiophene-5-yl)ethoxy)-1-(4-hydroxy-1-piperidinyl)-1-ethanone was obtained in the same manner as in Production Example 16(1).

Subsequently, a yellow oil product, 1-(2-(2-(1-benzothiophene-5-yl)ethoxy)ethyl)-4-piperidinol was obtained in the same manner as in Production Example 16(2).

IR (neat) cm$^{-1}$: 3386, 2939, 1110, 1071, 754, 701

NMR (CDCl$_3$) δppm: 1.5-2.3 (6H, m), 2.5-3.0 (2H, m), 2.56 (2H, t, J=6 Hz), 3.00 (2H, t, J=7 Hz), 3.5-3.9 (1H, m), 3.58 (2H, t, J=6 Hz), 3.70 (2H, t, J=7 Hz), 7.19 (1H, d, J=8 Hz), 7.27 (1H, d, J=5 Hz), 7.41 (1H, d, J=5 Hz), 7.65 (1H, s), 7.78 (1H, d, J=8 Hz)

Production Example 41

Production of 1-(2-(2-(1-benzothiophene-5-yl)ethoxy)ethyl)-4-piperidinol hydrochloride A light brown crystal, 1-(2-(2-(1-benzothiophene-5-yl)ethoxy)ethyl)-4-piperidinol hydrochloride was obtained in the same manner as in Production Example 21.

IR (KBr) cm$^{-1}$: 3312, 2946, 2691, 1457, 1124, 1043, 769, 712

NMR (CDCl$_3$) δppm: 1.5-2.5 (4H, m), 2.8-3.2 (6H, m), 2.99 (2H, t, J=6 Hz), 3.76 (2H, t, J=6 Hz), 3.8-4.2 (3H, m), 7.19 (1H, d, J=8 Hz), 7.30 (1H, d, J=5 Hz), 7.44 (1H, d, J=5 Hz), 7.67 (1H, s), 7.80 (1H, d, J=8 Hz)

Production Example 42

Production of 1-(2-(2-(1-benzothiophene-5-yl)ethoxy)ethyl)-3-piperidinol

A yellow oil product, 2-(2-(1-benzothiophene-5-yl)ethoxy)-1-(3-hydroxy-1-piperidinyl)-1-ethanone was obtained in the same manner as in Production Example 16(1).

IR (neat) cm$^{-1}$: 3408, 2938, 1637, 1114, 704

Subsequently, a yellow oil product, 1-(2-(2-(1-benzothiophene-5-yl)ethoxy)ethyl)-3-piperidinol was obtained in the same manner as in Production Example 16(2).

IR (neat) cm$^{-1}$: 3387, 2937, 1438, 1109, 703

NMR (CDCl$_3$) δppm: 1.4-2.0 (4H, m), 2.0-2.7 (6H, m), 2.57 (2H, t, J=6 Hz), 3.00 (2H, t, J=7 Hz), 3.56 (2H, t, J=6 Hz), 3.6-3.9 (1H, m), 3.70 (2H, t, J=7 Hz), 7.20 (1H, d, J=8 Hz), 7.28 (1H, d, J=5 Hz), 7.42 (1H, d, J=5 Hz), 7.66 (1H, s), 7.79 (1H, d, J=8 Hz)

Production Example 43

Production of 1-(2-(2-(1-benzothiophene-5-yl)ethoxy)ethyl)-3-piperidinol hydrochloride An achromatic crystal, 1-(2-(2-(1-benzothiophene-5-yl)ethoxy)ethyl)-3-piperidinol hydrochloride was obtained in the same manner as in Production Example 21.

IR (KBr) cm$^{-1}$: 3260, 2949, 2638, 1433, 1129, 1045, 702, 668

NMR (CDCl$_3$) δppm: 1.5-2.0 (4H, m), 2.1-2.8 (2H, m), 2.99 (2H, t, J=6 Hz), 3.1-3.6 (4H, m), 3.76 (2H, t, J=6 Hz), 3.8-4.1 (3H, m), 7.20 (1H, d, J=8 Hz), 7.30 (1H, d, J=5 Hz), 7.44 (1H, d, J=5 Hz), 7.67 (1H, s), 7.80 (1H, d, J=8 Hz)

Production Example 44

Production of 1-(2-(2-(1-benzofuran-5-yl)ethoxy)ethyl)-4-piperidinol 2-(2-(1-benzofuran-5-yl)ethoxy)-1-(4-hydroxy-1-piperidinyl)-1-ethanone was obtained in the same manner as in Production Example 16(1).

IR (neat) cm$^{-1}$: 3406, 2931, 1636, 1110, 771, 740

Subsequently, an achromatic oil product, 1-(2-(2-(1-benzofuran-5-yl)ethoxy)ethyl)-4-piperidinol was obtained in the same manner as in Production Example 16(2)

IR (neat) cm$^{-1}$: 3359, 2939, 1468, 1111, 1073, 882, 768, 739

NMR (CDCl$_3$)$_5$ ppm: 1.5-2.3 (6H, m), 2.5-3.0 (2H, m), 2.57 (2H, t, J=6 Hz), 2.97 (2H, t, J=7 Hz), 3.5-3.8 (1H, m), 3.58 (2H, t, J=6 Hz), 3.68 (2H, t, J=7 Hz), 6.71 (1H, dd, J=1, 2 Hz), 7.13 (1H, dd, J=2, 8 Hz), 7.40 (1H, d, J=8 Hz), 7.42 (1H, dd, J=1, 2 Hz), 7.55 (1H, d, J=2 Hz)

Production Example 45

Production of 1-(2-(2-(1-benzofuran-5-yl)ethoxy)ethyl)-4-piperidinol hydrochloride A light yellow oil product, 1-(2-(2-(1-benzofuran-5-yl)ethoxy)ethyl)-4-piperidinol hydrochloride was obtained in the same manner as in Production Example 39.

IR (neat) cm$^{-1}$: 3366, 2938, 2638, 1458, 1126, 776, 742

NMR (CDCl$_3$) δppm: 1.6-2.4 (4H, m), 2.8-3.2 (8H, m), 3.71 (2H, t, J=6 Hz), 3.7-4.1 (3H, m), 6.72 (1H, dd, J=1, 2 Hz), 7.12 (1H, dd, J=2, 8 Hz), 7.44 (1H, d, J=8 Hz), 7.42 (1H, dd, J=1, 2 Hz), 7.60 (1H, d, J=2 Hz)

Production Example 46

Production of 1-(2-(2-(1-benzofuran-5-yl)ethoxy)ethyl)-3-pyrrolidinol (1) 1.28 g of 2-(2-(1-benzofuran-5-yl)ethoxy)acetic acid was dissolved in 13.0 ml of tetrahydrofuran. The obtained solution was cooled to 5° C. Thereafter, 1.41 g of 1,1'-carbonyldiimidazole was added thereto, and the obtained mixture was then stirred at a room temperature for 2 hours. Thereafter, 1.22 ml of triethylamine and 0.72 ml of 3-pyrrolidinol were added to the reaction mixture, followed by stirring at a room temperature for 2 hours. Thereafter, water and ethyl acetate were added to the reaction mixture. The pH of the obtained mixture was adjusted to pH 1 by addition of 6 mol/l hydrochloric acid, and an organic layer was then separated. The organic layer was successively washed with a saturated sodium bicarbonate solution and a saturated saline solution, and then dried over anhydrous magnesium sulfate. Subsequently, the solvent was distilled away under a reduced pressure, so as to obtain 1.39 g of an achromatic oil product, 2-(2-(1-benzofuran-5-yl)ethoxy)-1-(3-hydroxy-1-pyrrolidinyl)-1-ethanone.

IR (neat) cm$^{-1}$: 3398, 2943, 1637, 1467, 1128, 1030, 771, 741

(2) 1.39 g of 2-(2-(1-benzofuran-5-yl)ethoxy)-1-(3-hydroxy-1-pyrrolidinyl)-1-ethanone was dissolved in 14.0 ml of tetrahydrofuran. Thereafter, 14.4 ml of a tetrahydrofuran solution containing a 1 mol/l borane-tetrahydrofuran complex was added dropwise to the obtained solution while cooling on ice, and the obtained mixture was then stirred at a room temperature for 17 hours. Thereafter, 8.0 ml of 6 mol/l hydrochloric acid was added to the reaction mixture, and the obtained mixture was heated to reflux for 1 hour. After cooling, water and ethyl acetate were added to the reaction mixture. The pH of the obtained mixture was adjusted to pH 10 by addition of a 2 mol/l aqueous sodium hydroxide solution, and an organic layer was separated. The organic layer was successively washed with water and a saturated saline solution, and then dried over anhydrous magnesium sulfate. Thereafter, the solvent was distilled away under a reduced pressure. The residue was purified by column chromatography (eluent; chloroform:methanol=30:1 to 10:1), so as to obtain 0.96 g of an achromatic oil product, 1-(2-(2-(1-benzofuran-5-yl)ethoxy)ethyl)-3-pyrrolidinol.

IR (neat) cm$^{-1}$: 3386, 2941, 1468, 1261, 1110, 1030, 882, 769, 738

NMR (CDCl$_3$) δppm: 1.5-2.0 (1H, m), 1.9-3.0 (5H, m), 2.68 (2H, t, J=6 Hz), 2.98 (2H, t, J=7 Hz), 3.58 (2H, t, J=6 Hz), 3.70 (2H, t, J=7 Hz), 4.2-4.4 (1H, m), 6.71 (1H, dd, J=1, 2 Hz), 7.14 (1H, d, J=8 Hz), 7.42 (1H, d, J=8 Hz), 7.4-7.5 (1H, m), 7.59 (1H, d, J=2 Hz)

Production Example 47

Production of 1-(2-(2-(1-benzofuran-5-yl)ethoxy)ethyl)-3-piperidinol oxalate

An achromatic crystal, 1-(2-(2-(1-benzofuran-5-yl)ethoxy)ethyl)-3-piperidinol oxalate was obtained in the same manner as in Production Example 17.

IR (KBr) cm$^{-1}$: 3418, 2945, 2698, 1715, 1197, 1111, 720

NMR (DMSO-d$_6$) δppm: 1.6-2.3 (2H, m), 2.92 (2H, t, J=7 Hz), 3.0-3.5 (6H, m), 3.5-3.8 (4H, m), 4.2-4.5 (1H, m), 6.89 (1H, dd, J=1, 2 Hz), 7.19 (1H, dd, J=1, 8 Hz), 7.50 (1H, d, J=8 Hz), 7.5-7.6 (1H, m), 7.94 (1H, d, J=2 Hz)

Production Example 48

Production of (3R*,4R*)-1-(2-(2-(1-benzothiophene-5-yl)ethoxy)ethyl)-3,4-pyrrolidinediol A yellow oil product, 2-(2-(1-benzothiophene-5-yl)ethoxy)-1-((3R*,4R*)-3,4-dihydroxy-1-pyrrolidinyl)-1-ethanone was obtained in the same manner as in Production Example 46(1).

IR (neat) cm$^{-1}$: 3370, 2935, 2874, 1636, 1131, 756, 701

Subsequently, a yellow oil product, (3R*,4R*)-1-(2-(2-(1-benzothiophene-5-yl)ethoxy)ethyl)-3,4-pyrrolidinediol was obtained in Production Example 46(2).

IR (neat) cm$^{-1}$: 3386, 2938, 2866, 1438, 1113, 756, 703

NMR (CDCl$_3$) δppm: 2.5-3.0 (5H, m), 3.00 (2H, t, J=7 Hz), 3.2-3.7 (1H, m), 3.56 (2H, t, J=6 Hz), 3.71 (2H, t, J=7 Hz), 3.9-4.4 (2H, m), 7.20 (1H, d, J=8 Hz), 7.28 (1H, d, J=5 Hz), 7.43 (1H, d, J=5 Hz), 7.66 (1H, s), 7.80 (1H, d, J=8 Hz)

Production Example 49

Production of (3R*,4R*)-1-(2-(2-(1-benzothiophene-5-yl)ethoxy)ethyl)-3,4-pyrrolidinediol oxalate An achromatic crystal, (3R*,4R*)-1-(2-(2-(1-benzothiophene-5-yl)ethoxy)ethyl)-3,4-pyrrolidinediol oxalate was obtained in the same manner as in Production Example 17.

IR (KBr) cm$^{-1}$: 3309, 2929, 1718, 1617, 1199, 1104, 702

NMR (DMSO-d$_6$) δppm: 2.8-3.2 (6H, m), 3.2-3.8 (6H, m), 4.1-4.4 (2H, m), 7.26 (1H, d, J=8 Hz), 7.39 (1H, d, J=5 Hz), 7.72 (1H, d, J=5 Hz), 7.75 (1H, s), 7.90 (1H, d, J=8 Hz)

Production Example 50

Production of 1-(2-(2-(5-methoxy-1-benzofuran-6-yl)ethoxy)ethyl)-3-pyrrolidinol

An achromatic oil product, 2-(2-(5-methoxy-1-benzofuran-6-yl)ethoxy)-1-(3-hydroxy-1-pyrrolidinyl)-1-ethanone was obtained in the same manner as in Production Example 46(1).

IR (neat) cm$^{-1}$: 3394, 2941, 1637, 1465, 1197, 1131, 1015, 841, 759

Subsequently, an achromatic oil product, 1-(2-(2-(5-methoxy-1-benzofuran-6-yl)ethoxy)ethyl)-3-pyrrolidinol was obtained in Production Example 46(2).

IR (neat) cm$^{-1}$: 3386, 2940, 1466, 1430, 1198, 1131, 1015, 837, 762

NMR (CDCl$_3$) δppm: 1.5-2.4 (3H, m), 2.5-3.0 (5H, m), 2.99 (2H, t, J=7 Hz), 3.59 (2H, t, J=6 Hz), 3.67 (2H, t, J=7 Hz), 3.85 (3H, s), 4.2-4.4 (1H, m), 6.68 (1H, d, J=2 Hz), 6.99 (1H, s), 7.34 (1H, s), 7.54 (1H, d, J=2 Hz)

Production Example 51

Production of 1-(2-(2-(5-methoxy-1-benzofuran-6-yl)ethoxy)ethyl)-3-piperidinol oxalate An achromatic crystal, 1-(2-(2-(5-methoxy-1-benzofuran-6-yl)ethoxy)ethyl)-3-piperidinol oxalate was obtained in the same manner as in Production Example 17.

IR (KBr) cm$^{-1}$: 3396, 2942, 2691, 1718, 1636, 1465, 1198, 1130, 720

NMR (DMSO-d$_6$) δppm: 1.7-2.3 (2H, m), 2.8-3.6 (6H, m), 2.91 (2H, t, J=6 Hz), 3.5-3.9 (4H, m), 3.83 (3H, s), 4.2-4.5 (1H, m), 6.86 (1H, d, J=2 Hz), 7.17 (1H, s), 7.43 (1H, s), 7.88 (1H, d, J=2 Hz)

Production Example 52

Production of 1-(2-(2-(6-methoxy-1-benzofuran-5-yl)ethoxy)ethyl)-3-pyrrolidinol

An achromatic oil product, 2-(2-(6-methoxy-1-benzofuran-5-yl)ethoxy)-1-(3-hydroxy-1-pyrrolidinyl)-1-ethanone was obtained in the same manner as in Production Example 46(1).
IR (neat) cm$^{-1}$: 3381, 2944, 1638, 1475, 1201, 1125, 1011, 758
Subsequently, an achromatic oil product, 1-(2-(2-(6-methoxy-1-benzofuran-5-yl)ethoxy)ethyl)-3-pyrrolidinol was obtained in Production Example 46(2).
IR (neat) cm$^{-1}$: 3398, 2938, 1475, 1202, 1094, 757, 730
NMR (CDCl$_3$) δppm: 1.5-2.4 (3H, m), 2.5-3.0 (5H, m), 2.98 (2H, t, J=7 Hz), 3.59 (2H, t, J=6 Hz), 3.68 (2H, t, J=7 Hz), 3.86 (3H, s), 4.2-4.4 (1H, m), 6.65 (1H, d, J=2 Hz), 7.00 (1H, s), 7.35 (1H, s), 7.50 (1H, d, J=2 Hz)

Production Example 53

Production of 1-(2-(2-(6-methoxy-1-benzofuran-5-yl)ethoxy)ethyl)-3-pyrrolidinol hydrochloride An achromatic oil product, 1-(2-(2-(6-methoxy-1-benzofuran-5-yl)ethoxy)ethyl)-3-pyrrolidinol hydrochloride was obtained in the same manner as in Production Example 39.
IR (neat) cm$^{-1}$: 3377, 2938, 2694, 1475, 1202, 1124, 1093, 1011
NMR (CDCl$_3$) δppm: 1.7-2.2 (2H, m), 2.8-3.6 (6H, m), 2.96 (2H, t, J=6 Hz), 3.5-4.2 (4H, m), 3.86 (3H, s), 4.3-4.6 (1H, m), 6.6-6.7 (1H, m), 7.01 (1H, s), 7.34 (1H, d, J=1 Hz), 7.51 (1H, d, J=2 Hz)

Production Example 54

Production of 1-(2-(2-(1-benzothiophene-5-yl)ethoxy)ethyl)-3-pyrrolidinamine (1) 1.00 g of 2-(2-(1-benzothiophene-5-yl)ethoxy)acetic acid was dissolved in 10.0 ml of tetrahydrofuran. The obtained solution was cooled to 5° C. Thereafter, 1.03 g of 1,1'-carbonyldiimidazole was added thereto, and the obtained mixture was then stirred at a room temperature for 1 hour. The reaction solution was cooled to 5° C. Thereafter, 0.88 ml of triethylamine and 1.18 g of tert-butyl=3-pyrrolidinyl carbamate were added to the reaction mixture, followed by stirring at a room temperature for 1 hour. Thereafter, water and ethyl acetate were added to the reaction mixture. The pH of the obtained mixture was adjusted to pH 4 by addition of 6 mol/l hydrochloric acid, and an organic layer was then separated. The organic layer was successively washed with a saturated sodium bicarbonate solution and a saturated saline solution, and then dried over anhydrous magnesium sulfate. Subsequently, the solvent was distilled away under a reduced pressure, so as to obtain 2.00 g of a light yellow oil product, tert-butyl=1-(2-(2-(1-benzothiophene-5-yl)ethoxy)acetyl)-3-pyrrolidinyl carbamate.
(2) 2.00 g of the obtained tert-butyl=1-(2-(2-(1-benzothiophene-5-yl)ethoxy)acetyl)-3-pyrrolidinyl carbamate was dissolved in 2.0 ml of tetrahydrofuran.

The obtained solution was cooled to 5° C. Thereafter, 10.6 ml of a tetrahydrofuran solution containing a 1 mol/l borane-tetrahydrofuran complex was added dropwise to the obtained solution, and the obtained mixture was then stirred at a room temperature for 17 hours. Thereafter, 3.5 ml of 6 mol/l hydrochloric acid was added to the reaction mixture, and the obtained mixture was heated to reflux for 3 hours. After the reaction mixture was cooled, water and ethyl acetate were added thereto. The pH of the obtained mixture was adjusted to pH 10 by addition of a 5 mol/l aqueous sodium hydroxide solution, and an organic layer was separated. The organic layer was washed with a saturated saline solution and then dried over anhydrous magnesium sulfate. Thereafter, the solvent was distilled away under a reduced pressure. The residue was purified by column chromatography (eluent; chloroform: methanol=30:1 to 15:1), so as to obtain 1.01 g of a light yellow oil product, 1-(2-(2-(1-benzothiophene-5-yl)ethoxy)ethyl)-3-pyrrolidinamine.
IR (neat) cm$^{-1}$: 3358, 2938, 2861, 1438, 1112, 1052, 755, 703
NMR (CDCl$_3$) δppm: 1.2-1.7 (1H, m), 1.9-3.0 (7H, m), 2.01 (2H, s), 3.00 (2H, t, J=7 Hz), 3.3-3.7 (1H, m), 3.57 (2H, t, J=6 Hz), 3.71 (2H, t, J=7 Hz), 7.20 (1H, d, J=8 Hz), 7.28 (1H, d, J=5 Hz), 7.41 (1H, d, J=5 Hz), 7.66 (1H, s), 7.78 (1H, d, J=8 Hz)

Production Example 55

Production of 1-(2-(2-(1-benzothiophene-5-yl)ethoxy)ethyl)-3-pyrrolidinamine dioxalate 0.71 g of 1-(2-(2-(1-benzothiophene-5-yl)ethoxy)ethyl)-3-pyrrolidinamine was dissolved in 3.0 ml of ethyl acetate. Thereafter, 4.0 ml of an ethyl acetate solution containing 0.44 g of oxalic acid was added to the obtained solution, and the obtained mixture was stirred at a room temperature for 1 hour and then at 5° C. for 1 hour. Thereafter, precipitated crystals were collected by filtration, washed with ethyl acetate, and then dried, so as to obtain 1.03 g of an achromatic crystal, 1-(2-(2-(1-benzothiophene-5-yl)ethoxy)ethyl)-3-pyrrolidinamine dioxalate.
IR (KBr) cm$^{-1}$: 3447, 2938, 1406, 1279, 1115, 720
NMR (DMSO-d$_6$) δppm: 1.7-2.5 (2H, m), 2.8-3.5 (8H, m), 3.5-4.0 (5H, m), 7.27 (1H, d, J=8 Hz), 7.40 (1H, d, J=5 Hz), 7.72 (1H, d, J=5 Hz), 7.75 (1H, s), 7.90 (1H, d, J=8 Hz)

Production Example 56

Production of 1-(2-(2-(1-benzofuran-5-yl)ethoxy)ethyl)-3-pyrrolidinamine

In the same manner as in Production Example 54(1), tert-butyl=1-(2-(2-(1-benzofuran-5-yl)ethoxy)acetyl)-3-pyrrolidinyl carbamate was obtained.
Subsequently, a yellow oil product, 1-(2-(2-(1-benzofuran-5-yl)ethoxy)ethyl)-3-pyrrolidinamine was obtained in the same manner as in Production Example 54(2).
IR (neat) cm$^{-1}$: 3356, 2938, 1467, 1261, 1111, 1030, 882, 769, 740
NMR (CDCl$_3$) δppm: 1.2-1.7 (1H, m), 2.02 (2H, s), 2.1-3.0 (7H, m), 2.98 (2H, t, J=7 Hz), 3.3-3.7 (1H, m), 3.57 (2H, t, J=6 Hz), 3.69 (2H, t, J=7 Hz), 6.71 (1H, dd, J=1, 2 Hz), 7.15 (1H, dd, J=1, 7 Hz), 7.40 (1H, d, J=7 Hz), 7.4-7.5 (1H, m), 7.59 (1H, d, J=2 Hz)

Production Example 57

Production of 1-(2-(2-(1-benzofuran-5-yl)ethoxy) ethyl)-3-pyrrolidinamine oxalate An achromatic crystal, 1-(2-(2-(1-benzofuran-5-yl) ethoxy)ethyl)-3-pyrrolidinamine oxalate was obtained in the same manner as in Production Example 17.
IR (KBr) cm$^{-1}$: 3408, 2952, 1615, 1311, 1127, 769
NMR (DMSO-d$_6$) δppm: 1.5-1.9 (1H, m), 1.8-2.4 (1H, m), 2.1-3.0 (6H, m), 2.89 (2H, t, J=7 Hz), 3.4-3.8 (5H, m), 6.89 (1H, dd, J=1, 2 Hz), 7.18 (1H, d, J=8 Hz), 7.50 (1H, d, J=8 Hz), 7.4-7.6 (1H, m), 7.94 (1H, d, J=2 Hz)

Production Example 58

Production of 1-(3-(2-(1-benzothiophene-5-yl) ethoxy)propyl)-3-pyrrolidinol 1.20 g of 5-(2-(3-chloropropoxy)ethyl)-1-benzothiophene was dissolved in 12 ml of N,N-dimethylformamide. Thereafter, 0.82 g of 3-pyrrolidinol and 1.30 g of potassium carbonate were added to the obtained solution, and the mixture was then stirred at 85° C. for 2.5 hours. After the reaction mixture was cooled, water and ethyl acetate were added thereto, and an organic layer was separated. The organic layer was successively washed with water and a saturated saline solution, and then dried over anhydrous magnesium sulfate. Thereafter, the solvent was distilled away under a reduced pressure. The residue was purified by column chromatography (eluent; chloroform:methanol=20:1 to 10:1), so as to obtain 0.78 g of an achromatic oil product, 1-(3-(2-(1-benzothiophene-5-yl) ethoxy)propyl)-3-pyrrolidinol.
IR (neat) cm$^{-1}$: 3386, 2943, 1438, 1106, 1052, 755, 701
NMR (CDCl$_3$) δppm: 1.5-2.0 (3H, m), 2.0-3.0 (7H, m), 2.98 (2H, t, J=7 Hz), 3.49 (2H, t, J=6 Hz), 3.67 (2H, t, J=7 Hz), 4.2-4.4 (1H, m), 7.1-7.3 (2H, m), 7.41 (1H, d, J=6 Hz), 7.66 (1H, s), 7.78 (1H, d, J=8 Hz)

Production Example 59

Production of 1-(3-(2-(1-benzothiophene-5-yl) ethoxy)propyl)-3-pyrrolidinol hydrochloride An achromatic crystal, 1-(3-(2-(1-benzothiophene-5-yl) ethoxy)propyl)-3-pyrrolidinol hydrochloride was obtained in the same manner as in Production Example 21.
IR (KBr) cm$^{-1}$: 3368, 2937, 2695, 1438, 1108, 821, 764, 708
NMR (CDCl$_3$) δppm: 1.8-2.3 (4H, m), 2.3-3.6 (6H, m), 2.96 (2H, t, J=6 Hz), 3.50 (2H, t, J=6 Hz), 3.68 (2H, t, J=7 Hz), 4.3-4.7 (1H, m), 7.21 (1H, d, J=8 Hz), 7.30 (1H, d, J=5 Hz), 7.43 (1H, d, J=5 Hz), 7.67 (1H, s), 7.80 (1H, d, J=8 Hz)

Production Example 60

Production of 1-(3-(2-(1-benzofuran-5-yl)ethoxy) propyl)-3-pyrrolidinol

A light yellow oil product, 1-(3-(2-(1-benzofuran-5-yl) ethoxy)propyl)-3-pyrrolidinol was obtained in the same manner as in Production Example 58.
IR (neat) cm$^{-1}$: 3386, 2942, 1467, 1261, 1108, 1030, 883, 740
NMR (CDCl$_3$) δppm: 1.5-2.0 (3H, m), 2.0-3.0 (7H, m), 2.95 (2H, t, J=7 Hz), 3.49 (2H, t, J=6 Hz), 3.65 (2H, t, J=7 Hz), 4.2-4.4 (1H, m), 6.71 (1H, dd, J=1, 2 Hz), 7.14 (1H, dd, J=1, 8 Hz), 7.3-7.5 (2H, m), 7.58 (1H, d, J=2 Hz)

Production Example 61

Production of 1-(3-(2-(1-benzofuran-5-yl)ethoxy) propyl)-3-pyrrolidinol hydrochloride A light yellow oil product, 1-(3-(2-(1-benzofuran-5-yl) ethoxy)propyl)-3-pyrrolidinol hydrochloride was obtained in the same manner as in Production Example 39.
IR (neat) cm$^{-1}$: 3339, 2941, 2605, 1468, 1262, 1110, 773, 742
NMR (CDCl$_3$) δppm: 1.6-2.4 (4H, m), 2.4-4.0 (12H, m), 4.4-4.8 (1H, m), 6.72 (1H, d, J=2 Hz), 7.12 (1H, d, J=8 Hz), 7.3-7.6 (2H, m), 7.59 (1H, d, J=2 Hz)

Production Example 62

Production of 1-(3-(2-(6-fluoro-1-benzothiophene-5-yl)ethoxy)propyl)-3-pyrrolidinol A yellow oil product, 1-(3-(2-(6-fluoro-1-benzothiophene-5-yl)ethoxy)propyl)-3-pyrrolidinol was obtained in the same manner as in Production Example 58.
IR (neat) cm$^{-1}$: 3422, 2952, 1458, 1257, 1106, 838, 747, 711
NMR (CDCl$_3$) δppm: 1.5-3.0 (10H, m), 3.00 (2H, t, J=7 Hz), 3.4-3.6 (2H, m), 3.68 (2H, t, J=7 Hz), 4.2-4.4 (1H, m), 7.23 (1H, d, J=5 Hz), 7.36 (1H, d, J=5 Hz), 7.51 (1H, d, J=10 Hz), 7.66 (1H, d, J=7 Hz)

Production Example 63

Production of 1-(3-(2-(6-fluoro-1-benzothiophene-5-yl)ethoxy)propyl)-3-pyrrolidinol hydrochloride A yellow oil product, 1-(3-(2-(6-fluoro-1-benzothiophene-5-yl)ethoxy)propyl)-3-pyrrolidinol hydrochloride was obtained in the same manner as in Production Example 39.
IR (neat) cm$^{-1}$: 3377, 2954, 2702, 1458, 1257, 1107, 750, 712
NMR (CDCl$_3$) δppm: 1.8-2.3 (4H, m), 2.8-3.6 (8H, m), 3.53 (2H, t, J=6 Hz), 3.69 (2H, t, J=7 Hz), 4.3-4.4 (1H, m), 7.27 (1H, d, J=5 Hz), 7.39 (1H, d, J=5 Hz), 7.52 (1H, d, J=10 Hz), 7.67 (1H, d, J=7 Hz)

Production Example 64

Production of (3R,4S)-1-(3-(2-(1-benzothiophene-5-yl)ethoxy)propyl)-3,4-pyrrolidinediol An achromatic oil product, (3R,4S)-1-(3-(2-(1-benzothiophene-5-yl)ethoxy)propyl)-3,4-pyrrolidinediol was obtained in the same manner as in Production Example 58.
IR (neat) cm$^{-1}$: 3387, 2940, 1438, 1159, 1108, 1051, 703
NMR (CDCl$_3$) δppm: 1.5-1.9 (2H, m), 2.4-2.8 (6H, m), 2.98 (2H, t, J=7 Hz), 3.47 (2H, t, J=6 Hz), 3.67 (2H, t, J=7 Hz), 4.1-4.3 (2H, m), 7.20 (1H, dd, J=1, 8 Hz), 7.27 (1H, d, J=5 Hz), 7.42 (1H, d, J=5 Hz), 7.65 (1H, d, J=1 Hz), 7.79 (1H, d, J=8 Hz)

Production Example 65

Production of (3R,4S)-1-(3-(2-(1-benzothiophene-5-yl)ethoxy)propyl)-3,4-pyrrolidinediol hydrochloride An achromatic crystal, (3R,4S)-1-(3-(2-(1-benzothiophene-5-yl)ethoxy)propyl)-3,4-pyrrolidinediol hydrochloride was obtained in the same manner as in Production Example 21.

IR (KBr) cm$^{-1}$: 3381, 2871, 2602, 1120, 808, 768, 718
NMR (DMSO-d$_6$) δppm: 1.8-2.0 (2H, m), 2.8-3.8 (12H, m), 3.9-4.3 (2H, m), 7.25 (1H, dd, J=2, 8 Hz), 7.39 (1H, d, J=5 Hz), 7.72 (1H, d, J=5 Hz), 7.73 (1H, d, J=2 Hz), 7.90 (1H, d, J=8 Hz)

Production Example 66

Production of 1-(3-(2-(1-benzothiophene-5-yl)ethoxy)propyl)-4-piperidinol

A light yellow oil product, 1-(3-(2-(1-benzothiophene-5-yl)ethoxy)propyl)-4-piperidinol was obtained in the same manner as in Production Example 58.

IR (neat) cm$^{-1}$: 3385, 2935, 1438, 1364, 1111, 755, 701
NMR (CDCl$_3$) δppm: 1.4-2.2 (8H, m), 2.1-2.5 (2H, m), 2.5-3.0 (2H, m), 2.98 (2H, t, J=7 Hz), 3.48 (2H, t, J=6 Hz), 3.5-3.8 (1H, m), 3.67 (2H, t, J=7 Hz), 7.1-7.3 (2H, m), 7.42 (1H, d, J=5 Hz), 7.66 (1H, s), 7.79 (1H, d, J=8 Hz)

Production Example 67

Production of 1-(3-(2-(1-benzothiophene-5-yl)ethoxy)propyl)-4-piperidinol oxalate An achromatic crystal, 1-(3-(2-(1-benzothiophene-5-yl)ethoxy)propyl)-4-piperidinol oxalate was obtained in the same manner as in Production Example 17.

IR (KBr) cm$^{-1}$: 3420, 2866, 1718, 1616, 1190, 1120, 705
NMR (DMSO-d$_6$) δppm: 1.5-2.0 (6H, m), 2.8-3.1 (8H, m), 3.4-3.8 (1H, m), 3.44 (2H, t, J=6 Hz), 3.64 (2H, t, J=6 Hz), 7.24 (1H, d, J=8 Hz), 7.40 (1H, d, J=5 Hz), 7.6-7.8 (2H, m), 7.91 (1H, d, J=8 Hz)

Production Example 68

Production of 1-(2-(2-(2-naphthyl)ethoxy)ethyl)-3-pyrrolidinol 0.80 g of 2-(2-(2-naphthyl)ethoxy)ethyl=methanesulfonate was dissolved in 8 ml of N,N-dimethylformamide. Thereafter, 0.45 ml of 3-pyrrolidinol and 0.75 g of potassium carbonate were added to the obtained solution, and the mixture was stirred at 90° C. for 2 hours. After the reaction mixture was cooled, water and ethyl acetate were added, and an organic layer was separated. The organic layer was successively washed with water and a saturated saline solution, and then dried over anhydrous magnesium sulfate. Thereafter, the solvent was distilled away under a reduced pressure. The residue was purified by column chromatography (eluent; chloroform:methanol=8:1 to 5:1), so as to obtain 0.51 g of an achromatic oil product, 1-(2-(2-(2-naphthyl)ethoxy)ethyl)-3-pyrrolidinol.

IR (neat) cm$^{-1}$: 3422, 2938, 1112, 820, 749
NMR (CDCl$_3$) δppm: 1.5-1.9 (1H, m), 2.0-2.5 (3H, m), 2.5-3.0 (4H, m), 3.05 (2H, t, J=7 Hz), 3.59 (2H, t, J=6 Hz), 3.75 (2H, t, J=7 Hz), 4.2-4.4 (1H, m), 7.2-7.6 (4H, m), 7.6-8.0 (3H, m)

Production Example 69

Production of 1-(2-(2-(2-naphthyl)ethoxy)ethyl)-3-pyrrolidinol oxalate

An achromatic crystal, 1-(2-(2-(2-naphthyl)ethoxy)ethyl)-3-pyrrolidinol oxalate was obtained in the same manner as in Production Example 17.

IR (KBr) cm$^{-1}$: 3366, 2945, 1405, 1113, 820, 720
NMR (DMSO-d$_6$) δppm: 1.6-2.3 (2H, m), 2.7-3.5 (8H, m), 3.5-3.9 (4H, m), 4.2-4.5 (1H, m), 7.4-7.6 (3H, m), 7.7-8.0 (4H, m)

Production Example 70

Production of (3R,4S)-1-(2-(2-(1-benzothiophene-5-yl)ethoxy)ethyl)-3,4-pyrrolidinediol 2.50 g of 2-(2-(1-benzothiophene-5-yl)ethoxy)ethyl =methanesulfonate was dissolved in 25 ml of N,N-dimethylformamide. Thereafter, 1.40 g of (3R,4S)-3,4-pyrrolidinediol hydrochloride and 4.70 ml of triethylamine were added to the obtained solution, and the mixture was then stirred at 90° C. for 1 hour. After cooling, water and ethyl acetate were added to the reaction mixture. The pH of the obtained mixture was adjusted to pH 10 by addition of a 2 mol/l aqueous sodium hydroxide solution, and an organic layer was then separated. The organic layer was successively washed with water and a saturated saline solution, and then dried over anhydrous magnesium sulfate. The solvent was then distilled away under a reduced pressure. The residue was purified by column chromatography (eluent; chloroform:methanol=8:1 to 5:1), so as to obtain 0.84 g of a yellow oil product, (3R,4S)-1-(2-(2-(1-benzothiophene-5-yl)ethoxy)ethyl)-3,4-pyrrolidinediol.

IR (neat) cm$^{-1}$: 3390, 2940, 1438, 1111, 1050, 703
NMR (CDCl$_3$) δppm: 2.5-3.0 (6H, m), 3.00 (2H, t, J=7 Hz), 3.55 (2H, t, J=6 Hz), 3.70 (2H, t, J=7 Hz), 4.0-4.3 (2H, m), 7.21 (1H, dd, J=1, 8 Hz), 7.28 (1H, d, J=5 Hz), 7.43 (1H, d, J=5 Hz), 7.66 (1H, d, J=1 Hz), 7.80 (1H, d, J=8 Hz)

Production Example 71

Production of (3R,4S)-1-(2-(2-(1-benzothiophene-5-yl)ethoxy)ethyl)-3,4-pyrrolidinediol hydrochloride An achromatic crystal, (3R,4S)-1-(2-(2-(1-benzothiophene-5-yl)ethoxy)ethyl)-3,4-pyrrolidinediol hydrochloride was obtained in the same manner as in Production Example 21.

IR (KBr) cm$^{-1}$: 3194, 2854, 1365, 1348, 1130, 1111, 820, 712
NMR (DMSO-d$_6$) δppm: 2.8-4.0 (12H, m), 3.9-4.3 (2H, m), 7.2-7.5 (2H, m), 7.7-8.2 (3H, m)

Production Example 72

Production of tert-butyl=1-(3-(2-(1-benzothiophene-5-yl)ethoxy)propyl)-3-pyrrolidinyl carbamate 0.70 g of 3-(2-(1-benzothiophene-5-yl)ethoxy)propyl=methanesulfonate was dissolved in 7 ml of N,N-dimethylformamide. Thereafter, 1.03 g of tert-butyl=3-pyrrolidinyl carbamate carbonate and 1.86 ml of triethylamine were added to the obtained solution, and the mixture was then stirred at 90° C. for 2 hours. After cooling, water and ethyl acetate were added to the reaction mixture. The pH of the obtained mixture was adjusted to pH 10 by addition of 6 mol/l hydrochloric acid, and an organic layer was then separated. The organic layer was successively washed with water and a saturated saline solution, and then dried over anhydrous magnesium sulfate. Thereafter, the solvent was then distilled away under a reduced pressure, so as to obtain 1.12 g of a yellow oil product, tert-butyl=1-(3-(2-(1-benzothiophene-5-yl)ethoxy)propyl)-3-pyrrolidinyl carbamate.

NMR (CDCl$_3$) δppm: 1.2-1.9 (3H, m), 1.44 (9H, s), 1.9-3.0 (7H, m), 2.99 (2H, t, J=7 Hz), 3.49 (2H, t, J=6 Hz), 3.67 (2H, t, J=7 Hz), 4.0-4.3 (1H, m), 7.19 (1H, d, J=8 Hz), 7.27 (1H, d, J=5 Hz), 7.42 (1H, d, J=5 Hz), 7.66 (1H, s), 7.79 (1H, d, J=8 Hz)

Production Example 73

Production of 1-(3-(2-(1-benzothiophene-5-yl)ethoxy)propyl)-3-pyrrolidinamine 1.12 g of tert-butyl=1-(3-(2-(1-benzothiophene-5-yl)ethoxy)propyl)-3-pyrrolidinyl carbamate was dissolved in 7.0 ml of ethyl acetate. Thereafter, 1.86 ml of 6 mol/l hydrochloric acid was added to the obtained solution, and the mixture was then heated to reflux for 1 hour. After cooling, water and ethyl acetate were added to the reaction mixture. The pH of the obtained mixture was adjusted to pH 10 by addition of a 2 mol/l aqueous sodium hydroxide solution, and an organic layer was then separated. The organic layer was successively washed with water and a saturated saline solution, and then dried over anhydrous magnesium sulfate. The solvent was then distilled away under a reduced pressure. The residue was purified by column chromatography (eluent; chloroform:methanol=30:1 to 20:1), so as to obtain 0.38 g of a light yellow oil product, 1-(3-(2-(1-benzothiophene-5-yl)ethoxy)propyl)-3-pyrrolidinamine.

IR (neat) cm$^{-1}$: 3357, 2937, 2861, 2796, 1146, 1108, 755, 701

NMR (CDCl$_3$) δppm: 1.2-1.9 (4H, m), 1.9-2.8 (7H, m), 2.97 (2H, t, J=7 Hz), 3.48 (2H, t, J=6 Hz), 3.66 (2H, t, J=7 Hz), 7.19 (1H, d, J=8 Hz), 7.23 (1H, d, J=5 Hz), 7.39 (1H, d, J=5 Hz), 7.64 (1H, s), 7.77 (1H, d, J=8 Hz)

Production Example 74

Production of 1-(3-(2-(1-benzothiophene-5-yl)ethoxy)propyl)-3-pyrrolidinamine oxalate An achromatic crystal, 1-(3-(2-(1-benzothiophene-5-yl)ethoxy)propyl)-3-pyrrolidinamine oxalate was obtained in the same manner as in Production Example 17.

IR (KBr) cm$^{-1}$: 3390, 2871, 1614, 1310, 1122, 766

NMR (DMSO-d$_6$) δppm: 1.5-1.9 (2H, m), 1.9-2.9 (8H, m), 2.92 (2H, t, J=7 Hz), 3.3-3.7 (1H, m), 3.43 (2H, t, J=6 Hz), 3.62 (2H, t, J=7 Hz), 7.25 (1H, d, J=8 Hz), 7.39 (1H, d, J=5 Hz), 7.72 (1H, d, J=5 Hz), 7.73 (1H, s), 7.90 (1H, d, J=8 Hz)

Production Example 75

Production of N-(1-(3-(2-(1-benzothiophene-5-yl)ethoxy)propyl)-3-pyrrolidinyl)acetamide 0.50 g of 1-(3-(2-(1-benzothiophene-5-yl)ethoxy)propyl)-3-pyrrolidinamine was dissolved in 5 ml of methylene chloride. The obtained solution was cooled to −60° C. Thereafter, 0.27 ml of triethylamine and 0.14 ml of acetyl chloride were added thereto, and the obtained mixture was stirred at a room temperature for 1 hour. Thereafter, water and ethyl acetate were added to the reaction mixture, and an organic layer was then separated. The organic layer was washed with a saturated saline solution and then dried over anhydrous magnesium sulfate. The solvent was then distilled away under a reduced pressure. The residue was purified by column chromatography (eluent; chloroform:methanol=50:1 to 10:1), so as to obtain 0.55 g of a yellow oil product, N-(1-(3-(2-(1-benzothiophene-5-yl)ethoxy)propyl)-3-pyrrolidinyl)acetamide.

IR (neat) cm$^{-1}$: 3292, 2946, 1654, 1560, 1110, 757, 702

NMR (CDCl$_3$) δppm: 1.5-1.7 (1H, m), 1.7-1.8 (2H, m), 1.94 (3H, s), 2.13 (1H, q, J=9 Hz), 2.2-2.3 (1H, m), 2.4-2.5 (3H, m), 2.59 (1H, dd, J=2, 10 Hz), 2.86 (1H, dt, J=4, 9 Hz), 2.99 (2H, t, J=7 Hz), 3.49 (2H, t, J=6 Hz), 3.67 (2H, t, J=7 Hz), 4.3-4.5 (1H, m), 5.8-5.9 (1H, m), 7.22 (1H, dd, J=1, 8 Hz), 7.28 (1H, d, J=5 Hz), 7.42 (1H, d, J=5 Hz), 7.67 (1H, d, J=1 Hz), 7.79 (1H, d, J=8 Hz)

Production Example 76

Production of N-(1-(3-(2-(1-benzothiophene-5-yl)ethoxy)propyl)-3-pyrrolidinyl)acetamide hydrochloride A light brown crystal, N-(1-(3-(2-(1-benzothiophene-5-yl)ethoxy)propyl)-3-pyrrolidinyl)acetamide hydrochloride was obtained in the same manner as in Production Example 21.

IR (KBr) cm$^{-1}$: 3422, 2868, 2475, 1664, 1542, 1343, 1117, 711

NMR (CDCl$_3$) δppm: 1.9-2.1 (3H, m), 2.05 (3H, s), 2.3-2.4 (1H, m), 2.4-2.5 (1H, m), 2.6-2.7 (1H, m), 2.8-2.9 (2H, m), 2.97 (2H, t, J=6 Hz), 3.4-3.5 (1H, m), 3.51 (2H, t, J=6 Hz), 3.6-3.7 (1H, m), 3.70 (2H, t, J=6 Hz), 4.6-4.8 (1H, m), 7.22 (1H, dd, J=1, 8 Hz), 7.31 (1H, d, J=5 Hz), 7.46 (1H, d, J=5 Hz), 7.67 (1H, s), 7.81 (1H, d, J=8 Hz)

Production Example 77

Production of N-(1-(3-(2-(1-benzothiophene-5-yl)ethoxy)propyl)-3-pyrrolidinyl)methanesulfonamide A yellow oil product, N-(1-(3-(2-(1-benzothiophene-5-yl)ethoxy)propyl)-3-pyrrolidinyl)methanesulfonamide was obtained in the same manner as in Production Example 75.

IR (neat) cm$^{-1}$: 3270, 2927, 2856, 1320, 1148, 1110, 756

NMR (CDCl$_3$) δppm: 1.6-1.8 (3H, m), 2.1-2.3 (2H, m), 2.44 (2H, t, J=7 Hz), 2.50 (1H, dd, J=6, 10 Hz), 2.60 (1H, dd, J=3, 10 Hz), 2.77 (1H, dt, J=4, 9 Hz), 2.94 (3H, s), 2.99 (2H, t, J=7 Hz), 3.48 (2H, t, J=6 Hz), 3.68 (2H, t, J=7 Hz), 3.9-4.0 (1H, m), 4.6-4.8 (1H, m), 7.22 (1H, dd, J=1, 8 Hz), 7.28 (1H, d, J=5 Hz), 7.42 (1H, d, J=5 Hz), 7.67 (1H, d, J=1 Hz), 7.79 (1H, d, J=8 Hz)

Production Example 78

Production of N-(1-(3-(2-(1-benzothiophene-5-yl)ethoxy)propyl)-3-pyrrolidinyl)methanesulfonamide oxalate An achromatic crystal, N-(1-(3-(2-(1-benzothiophene-5-yl)ethoxy)propyl)-3-pyrrolidinyl)methanesulfonamide oxalate was obtained in the same manner as in Production Example 17.

IR (KBr) cm$^{-1}$: 3250, 2868, 1718, 1314, 1165, 1119, 707

NMR (DMSO-d$_6$) δppm: 1.8-2.0 (3H, m), 2.2-2.3 (1H, m), 2.93 (2H, t, J=7 Hz), 2.97 (3H, s), 3.0-3.1 (3H, m), 3.1-3.2 (1H, m), 3.2-3.3 (1H, m), 3.4-3.5 (1H, m), 3.45 (2H, t, J=6 Hz), 3.63 (2H, t, J=7 Hz), 4.0-4.1 (1H, m), 7.26 (1H, dd, J=1, 8 Hz), 7.40 (1H, d, J=5 Hz), 7.4-7.6 (1H, m), 7.72 (1H, d, J=5 Hz), 7.74 (1H, d, J=1 Hz), 7.90 (1H, d, J=8 Hz)

Production Example 79

Production of 1-(3-(2-(1-benzothiophene-5-yl)ethoxy)propyl)-N,N-dimethyl-3-pyrrolidinamine 0.43 g of 1-(3-(2-(1-benzothiophene-5-yl)ethoxy)propyl)-3-pyrrolidinamine was dissolved in 8.6 ml of methanol. The obtained solution was cooled to 5° C. Thereafter, 0.35 ml of 37% formalin and 0.09 g of sodium borohydride were added thereto, and the obtained mixture was stirred at a room temperature for 17 hours. Thereafter, 2.6 ml of 2 mol/l hydrochloric acid was added to the reaction mixture under cooling on ice, and the obtained mixture was then stirred at a room temperature for 30 minutes. Thereafter, water and ethyl acetate were added to the reaction mixture, and a water layer was then separated. After ethyl acetate was added to the water layer, the pH of the mixture was adjusted to pH 9.5 by addition of a 2 mol/l aqueous sodium hydroxide solution, and an organic layer was separated. The organic layer was washed with a saturated saline solution and then dried over anhydrous magnesium sulfate. The solvent was then distilled away under a reduced pressure. The residue was purified by column chromatography (eluent; chloroform:methanol=50:1 to 10:1), so as to obtain 0.39 g of a yellow oil product, 1-(3-(2-(1-benzothiophene-5-yl)ethoxy)propyl)-N,N-dimethyl-3-pyrrolidinamine.

IR (neat) cm$^{-1}$: 2945, 2862, 2786, 1458, 1111, 700

NMR (CDCl$_3$) δppm: 1.6-1.8 (3H, m), 1.9-2.0 (1H, m), 2.20 (6H, s), 2.2-2.3 (1H, m), 2.3-2.5 (2H, m), 2.50 (1H, dt, J=8, 12 Hz), 2.7-2.8 (2H, m), 2.8-2.9 (1H, m), 2.99 (2H, t, J=7 Hz), 3.49 (2H, t, J=7 Hz), 3.67 (2H, t, J=7 Hz), 7.22 (1H, dd, J=1, 8 Hz), 7.28 (1H, d, J=5 Hz), 7.41 (1H, d, J=5 Hz), 7.67 (1H, d, J=1 Hz), 7.79 (1H, d, J=8 Hz)

Production Example 80

Production of 1-(3-(2-(1-benzothiophene-5-yl)ethoxy)propyl)-N,N-dimethyl-3-pyrrolidinamine dihydrochloride 0.39 g of 1-(3-(2-(1-benzothiophene-5-yl)ethoxy)propyl)-N,N-dimethyl-3-pyrrolidinamine was dissolved in 4.0 ml of ethyl acetate. Thereafter, 0.80 ml of an ethyl acetate solution containing 3.25 mol/l dry hydrogen chloride was added to the obtained solution, and the mixture was stirred at a room temperature for 1 hour and then at 5° C. for 1 hour. Thereafter, precipitated crystals were collected by filtration. The crystals were washed with ethyl acetate and then dried, so as to obtain 0.32 g of an achromatic crystal, 1-(3-(2-(1-benzothiophene-5-yl)ethoxy)propyl)-N,N-dimethyl-3-pyrrolidinamine dihydrochloride.

IR (KBr) cm$^{-1}$: 2936, 1437, 1101, 701

NMR (CDCl$_3$) δppm: 1.9-2.1 (2H, m), 2.4-2.6 (2H, m), 2.84 (6H, s), 2.98 (2H, t, J=7 Hz), 3.1-3.2 (2H, m), 3.4-3.9 (4H, m), 3.54 (2H, t, J=5 Hz), 3.72 (2H, dt, J=3, 7 Hz), 4.2-4.3 (1H, m), 7.24 (1H, d, J=8 Hz), 7.35 (1H, d, J=5 Hz), 7.43 (1H, d, J=5 Hz), 7.71 (1H, s), 7.84 (1H, d, J=8 Hz)

Reference Example 1

Production of 3-(2-(1-benzothiophene-4-yl)ethoxy)-1-propanol 2.2 g of 2-(1-benzothiophene-4-yl)-1-ethanol was suspended in 2.2 ml of toluene and 8.8 ml of a 50% (W/V) aqueous sodium hydroxide solution. Thereafter, 4.41 g of 2-(3-chloropropoxy)tetrahydro-2H-pyran and 0.42 g of tetra-n-butyl ammonium hydrogen sulfate were added to the suspension, and the obtained mixture was then heated to reflux for 2 hours. After cooling, water and toluene were added to the reaction mixture, and an organic layer was separated. The organic layer was successively washed with water and a saturated saline solution, and then dried over anhydrous magnesium sulfate. Subsequently, the solvent was distilled away under a reduced pressure, so as to obtain 6.50 g of a light brown oil mixture consisting of 2-(3-(2-(1-benzothiophene-4-yl)ethoxy)propoxy)tetrahydro-2H-pyran and 2-(3-chloropropoxy)tetrahydro-2H-pyran.

6.50 g of this mixture was dissolved in 8.0 ml of methanol. Thereafter, 8.0 ml of water and 0.70 g of p-toluenesulfonic acid monohydrate were added to the obtained solution. The obtained mixture was then stirred at a room temperature for 12 hours. Thereafter, ethyl acetate and a saturated sodium bicarbonate solution were added to the reaction mixture, and an organic layer was then separated. The organic layer was successively washed with water and a saturated saline solution, and then dried over anhydrous magnesium sulfate. The solvent was then distilled away under a reduced pressure. The residue was purified by column chromatography (eluent; toluene:ethyl acetate=4:1 to 3:1), so as to obtain 1.42 g of an oil product, 3-(2-(1-benzothiophene-4-yl)ethoxy)-1-propanol.

IR (neat) cm$^{-1}$: 3394, 2943, 2867, 1413, 1110, 761

NMR (CDCl$_3$) δppm: 1.81 (2H, qn, J=6 Hz), 2.1 (1H, brs), 3.26 (2H, t, J=7 Hz), 3.63 (2H, t, J=6 Hz), 3.69 (2H, t, J=7 Hz), 3.76 (2H, t, J=6 Hz), 7.0-7.4 (2H, m), 7.45 (2H, s), 7.77 (1H, dd, J=2, 7 Hz)

Reference Example 2

The following compound was obtained in the same manner as in Reference Example 1.

3-(2-(1-benzothiophene-2-yl)ethoxy)-1-propanol

NMR (CDCl$_3$) δppm: 1.68 (1H, brs), 1.86 (2H, qn, J=6 Hz), 3.17 (2H, t, J=6 Hz), 3.67 (2H, t, J=6 Hz), 3.76 (4H, t, J=6 Hz), 7.07 (1H, s), 7.2-7.4 (2H, m), 7.67 (1H, d, J=8 Hz), 7.77 (1H, d, J=8 Hz)

3-(2-(1-benzothiophene-3-yl)ethoxy)-1-propanol

IR (neat) cm$^{-1}$: 3395, 2942, 2867, 1427, 1113, 762, 732

NMR (CDCl$_3$) δppm: 1.83 (2H, qn, J=6 Hz), 2.27 (1H, t, J=6 Hz), 3.13 (2H, t, J=7 Hz), 3.65 (2H, t, J=6 Hz), 3.74 (2H, t, J=6 Hz), 3.78 (2H, t, J=7 Hz), 7.18 (1H, s), 7.34 (1H, dt, J=1, 7 Hz), 7.39 (1H, dt, J=1, 7 Hz), 7.76 (1H, dd, J=1, 7 Hz), 7.86 (1H, dd, J=1, 7 Hz)

3-(2-(1-benzothiophene-5-yl)ethoxy)-1-propanol

IR (neat) cm$^{-1}$: 3398, 2939, 2866, 1438, 1110, 704

NMR (CDCl$_3$) δppm: 1.82 (2H, qn, J=6 Hz), 2.29 (1H, t, J=6 Hz), 3.00 (2H, t, J=7 Hz), 3.64 (2H, t, J=6 Hz), 3.71 (2H, t, J=7 Hz), 3.73 (2H, q, J=6 Hz), 7.22 (1H, dd, J=1, 8 Hz), 7.28 (1H, d, J=5 Hz), 7.42 (1H, d, J=5 Hz), 7.66 (1H, d, J=1 Hz), 7.80 (1H, d, J=8 Hz)

3-(2-(1-benzothiophene-6-yl)ethoxy)-1-propanol

IR (neat) cm$^{-1}$: 3389, 2942, 2865, 1397, 1111, 819, 693

NMR (CDCl$_3$) δppm: 1.82 (2H, qn, J=6 Hz), 2.24 (1H, t, J=6 Hz), 3.00 (2H, t, J=7 Hz), 3.64 (2H, t, J=6 Hz), 3.71 (2H, t, J=7 Hz), 3.74 (2H, q, J=6 Hz), 7.21 (1H, d, J=8 Hz), 7.28

(1H, d, J=5 Hz), 7.38 (1H, d, J=5 Hz), 7.70 (1H, s), 7.75 (1H, d, J=8 Hz)
3-(2-(1-benzothiophene-7-yl)ethoxy)-1-propanol Reference Example 3

Production of
4-(2-(3-chloropropoxy)ethyl)-1-benzothiophene 1.40 g of 3-(2-(1-benzothiophene-4-yl)ethoxy)-1-propanol was dissolved in 7.0 ml of methylene chloride. Thereafter, 1.10 ml of thionyl chloride and 0.05 ml of N,N-dimethylformamide were added to the obtained solution, and the obtained mixture was then heated to reflux for 5 hours. Subsequently, the solvent was distilled away under a reduced pressure. The residue was purified by column chromatography (eluent; hexane:ethyl acetate=20:1), so as to obtain 1.43 g of a yellow oil product, 4-(2-(3-chloropropoxy)ethyl)-1-benzothiophene.

IR (neat) cm$^{-1}$: 2867, 1413, 1113, 760
NMR (CDCl$_3$) δppm: 1.99 (2H, qn, J=6 Hz), 3.23 (2H, t, J=7 Hz), 3.58 (2H, t, J=6 Hz), 3.59 (2H, t, J=6 Hz), 3.75 (2H, t, J=7 Hz), 7.18 (1H, dd, J=2, 7 Hz), 7.29 (1H, t, J=7 Hz), 7.1-7.3 (2H, m), 7.45 (2H, s), 7.76 (1H, dd, J=2, 8 Hz)

Reference Example 4

The following compound was obtained in the same manner as in Reference Example 3.
2-(2-(3-chloropropoxy)ethyl)-1-benzothiophene
NMR (CDCl$_3$) δppm: 2.04 (2H, qn, J=6 Hz), 3.16 (2H, t, J=7 Hz), 3.62 (2H, t, J=6 Hz), 3.66 (2H, t, J=6 Hz), 3.75 (2H, t, J=7 Hz), 7.06 (1H, s), 7.25 (1H, dt, J=1, 7 Hz), 7.30 (1H, dt, J=1, 7 Hz), 7.67 (1H, dd, J=1, 7 Hz), 7.77 (1H, dd, J=1, 7 Hz)
3-(2-(3-chloropropoxy)ethyl)-1-benzothiophene
IR (neat) cm$^{-1}$: 2865, 1427, 1115, 762, 732
NMR (CDCl$_3$) δppm: 2.02 (2H, qn, J=6 Hz), 3.13 (2H, t, J=7 Hz), 3.61 (2H, t, J=6 Hz), 3.62 (2H, t, J=6 Hz), 3.79 (2H, t, J=7 Hz), 7.19 (1H, s), 7.34 (1H, dt, J=1, 7 Hz), 7.39 (1H, dt, J=1, 7 Hz), 7.77 (1H, dd, J=1, 7 Hz), 7.86 (1H, dd, J=1, 7 Hz)
5-(2-(3-chloropropoxy)ethyl)-1-benzothiophene
IR (neat) cm$^{-1}$: 2864, 1438, 1113, 755, 701
NMR (CDCl$_3$) δppm: 2.01 (2H, qn, J=6 Hz), 3.00 (2H, t, J=7 Hz), 3.59 (2H, t, J=6 Hz), 3.61 (2H, t, J=6 Hz), 3.70 (2H, t, J=7 Hz), 7.22 (1H, dd, J=1, 8 Hz), 7.28 (1H, d, J=5 Hz), 7.42 (1H, d, J=5 Hz), 7.68 (1H, d, J=1 Hz), 7.79 (1H, d, J=8 Hz)
6-(2-(3-chloropropoxy)ethyl)-1-benzothiophene
IR (neat) cm$^{-1}$: 2864, 1113, 820, 761, 695, 652
NMR (CDCl$_3$) δppm: 2.00 (2H, qn, J=6 Hz), 3.00 (2H, t, J=7 Hz), 3.58 (2H, t, J=6 Hz), 3.61 (2H, t, J=6 Hz), 3.70 (2H, t, J=7 Hz), 7.21 (1H, d, J=8 Hz), 7.28 (1H, d, J=5 Hz), 7.37 (1H, d, J=5 Hz), 7.72 (1H, s), 7.73 (1H, d, J=8 Hz)
7-(2-(3-chloropropoxy)ethyl)-1-benzothiophene
IR (neat) cm$^{-1}$: 2866, 1460, 1395, 1115, 795, 701
NMR (CDCl$_3$) δppm: 2.00 (2H, qn, J=6 Hz), 3.17 (2H, t, J=7 Hz), 3.60 (4H, t, J=6 Hz), 3.82 (2H, t, J=7 Hz), 7.20 (1H, d, J=8 Hz), 7.33 (1H, t, J=8 Hz), 7.35 (1H, d, J=5 Hz), 7.42 (1H, d, J=5 Hz), 7.70 (1H, d, J=8 Hz)

Reference Example 5

Production of 3-(2-(1-benzothiophene-5-yl)ethoxy)propyl=methanesulfonate 2.03 g of 3-(2-(1-benzothiophene-5-yl)ethoxy)-1-propanol was dissolved in 16.8 ml of methylene chloride. Thereafter, 2.43 ml of methanesulfonyl chloride, 4.37 ml of triethylamine, and 0.10 g of 4-(dimethylamino)pyridine were added to the obtained solution, while cooling on ice. The obtained mixture was stirred at the same temperature for 30 minutes and then at a room temperature for 12 hours. Thereafter, methyl chloride and water were added to the reaction mixture, and an organic layer was separated. The organic layer was successively washed with water and a saturated saline solution, and then dried over anhydrous magnesium sulfate. The solvent was then distilled away under a reduced pressure. The residue was purified by column chromatography (eluent; hexane:ethyl acetate=5:1), so as to obtain 1.40 g of 3-(2-(1-benzothiophene-5-yl)ethoxy)propyl=methanesulfonate.

IR (neat) cm$^{-1}$: 2937, 2866, 1352, 1174, 1114, 943, 705, 529
NMR (CDCl$_3$) δppm: 1.97 (2H, qn, J=6 Hz), 2.81 (3H, s), 2.98 (2H, t, J=7 Hz), 3.54 (2H, t, J=6 Hz), 3.70 (2H, t, J=6 Hz), 4.26 (2H, t, J=7 Hz), 7.20 (1H, dd, J=1, 8 Hz), 7.28 (1H, d, J=5 Hz), 7.42 (1H, d, J=5 Hz), 7.65 (1H, d, J=1 Hz), 7.79 (1H, d, J=8 Hz)

Reference Example 6

Production of 2-(2-(6-methoxy-1-benzofuran-5-yl)ethoxy)acetic acid and 2-(2-(5-methoxy-1-benzofuran-6-yl)ethoxy)acetic acid (1) Production of 2,4-dimethoxyphenethyl=acetate 15.0 g of 2-(2,4-dimethoxyphenyl)-1-ethanol was dissolved in 150 ml of methylene chloride. Thereafter, 9.32 ml of acetic anhydride, 13.8 ml of triethylamine, and 0.10 g of 4-(dimethylamino)pyridine were added to the obtained solution, while cooling on ice. The obtained mixture was stirred at the same temperature for 30 minutes and then at a room temperature for 12 hours. Thereafter, water was added to the reaction mixture. The pH of the mixture was adjusted to pH 1.5 by addition of 6 mol/l hydrochloric acid, and an organic layer was separated. The organic layer was successively washed with water and a saturated saline solution, and then dried over anhydrous magnesium sulfate. The solvent was then distilled away under a reduced pressure. The residue was purified by column chromatography (eluent; hexane:ethyl acetate=5:1), so as to obtain 17.2 g of an achromatic oil product, 2,4-dimethoxyphenethyl=acetate.

IR (neat) cm$^{-1}$: 2958, 1736, 1509, 1243, 1035, 834
NMR (CDCl$_3$) δppm: 2.03 (3H, s), 2.87 (2H, t, J=7 Hz), 3.80 (6H, s), 4.22 (2H, t, J=7 Hz), 6.41 (1H, d, J=9 Hz), 6.46 (1H, s), 7.05 (1H, d, J=9 Hz)

Also, 2,5-dimethoxyphenethyl=acetate was obtained in the same above manner.
IR (neat) cm$^{-1}$: 2952, 1736, 1502, 1226, 1048, 802, 710
NMR (CDCl$_3$) δppm: 2.01 (3H, s), 2.90 (2H, t, J=7 Hz), 3.74 (3H, s), 3.76 (3H, s), 4.25 (2H, t, J=7 Hz), 6.74 (3H, s)

(2) Production of
5-acetyl-2,4-dimethoxyphenethyl=acetate 17.0 g of 2,4-dimethoxyphenethyl=acetate was dissolved in 170 ml of methylene chloride. Thereafter, 5.93 ml of acetyl chloride and 12.1 g of aluminum chloride were added to the obtained solution, while cooling on ice. The obtained mixture was stirred at the same temperature for 1 hour. Thereafter, the reaction mixture was poured into ice water, and an organic layer was separated. The organic layer was successively washed with water and a saturated saline solution, and then dried over anhydrous magnesium sulfate. The solvent was then distilled away under a reduced pressure. Diisopropyl ether was added to the residue, and precipitated crystals were then collected by filtration. The obtained crystals were washed with diisopropyl ether and then dried, so as to obtain 13.9 g of a yellow crystal, 5-acetyl-2,4-dimethoxyphenethyl=acetate.

NMR (CDCl$_3$) δppm: 2.01 (3H, s), 2.57 (3H, s), 2.88 (2H, t, J=7 Hz), 3.90 (3H, s), 3.93 (3H, s), 4.21 (2H, t, J=7 Hz), 6.42 (1H, s), 7.68 (1H, s)

Also, 4-acetyl-2,5-dimethoxyphenethyl=acetate was obtained in the same above manner.

(3) Production of 5-acetyl-4-hydroxy-2-methoxyphenethyl=acetate 13.9 g of 5-acetyl-2,4-dimethoxyphenethyl=acetate was dissolved in 70 ml of acetonitrile. Thereafter, 13.9 g of aluminum chloride and 7.82 g of sodium iodide were added to the obtained solution, while cooling on ice. The obtained mixture was stirred at 50° C. for 3 hours. Thereafter, the reaction mixture was poured into ice water, ethyl acetate was then added to the obtained mixture, and an organic layer was then separated. The organic layer was successively washed with water and a saturated saline solution, and then dried over anhydrous magnesium sulfate. The solvent was then distilled away under a reduced pressure, so as to obtain 13.3 g of a yellow oil product, 5-acetyl-4-hydroxy-2-methoxyphenethyl=acetate.

Also, 4-acetyl-5-hydroxy-2-methoxyphenethyl=acetate was obtained in the same above manner.

(4) Production of 1-(2-hydroxy-5-(2-hydroxyethyl)-4-methoxyphenyl)-1-ethanone 13.3 g of the above 5-acetyl-4-hydroxy-2-methoxyphenethyl=acetate was dissolved in 30 ml of ethanol. Thereafter, 21 ml of a 5 mol/l aqueous sodium hydroxide solution was added to the obtained solution, and the obtained mixture was stirred at a room temperature for 17 hours. Thereafter, water and ethyl acetate were added to the reaction mixture, and the pH of the obtained mixture was adjusted to pH 1 by addition of 6 mol/l hydrochloric acid. Thereafter, an organic layer was separated. The organic layer was successively washed with water and a saturated saline solution, and then dried over anhydrous magnesium sulfate. The solvent was then distilled away under a reduced pressure. Diisopropyl ether was added to the residue, and precipitated crystals were then collected by filtration. The obtained crystals were washed with diisopropyl ether and then dried, so as to obtain 8.30 g of a yellow crystal, 1-(2-hydroxy-5-(2-hydroxyethyl)-4-methoxyphenyl)-1-ethanone.

Also, 1-(2-hydroxy-4-(2-hydroxyethyl)-5-methoxyphenyl)-1-ethanone was obtained in the same above manner.

NMR (CDCl$_3$) δppm: 1.6-1.8 (1H, m), 2.61 (3H, s), 2.90 (2H, t, J=7 Hz), 3.8-4.1 (2H, m), 3.84 (3H, s), 6.84 (1H, s), 7.06 (1H, s), 11.98 (1H, s)

(5) Production of 2-bromo-1-(2-hydroxy-5-(2-hydroxyethyl)-4-methoxyphenyl)-1-ethanone 10.0 g of 1-(2-hydroxy-5-(2-hydroxyethyl)-4-methoxyphenyl)-1-ethanone was dissolved in 100 ml of methylene chloride. Thereafter, 2.94 ml of bromine was added dropwise to the obtained solution. The obtained mixture was stirred at a room temperature for 1 hour. Thereafter, the reaction mixture was poured into ice water, and an organic layer was separated. The organic layer was successively washed with water and a saturated saline solution, and then dried over anhydrous magnesium sulfate. The solvent was then distilled away under a reduced pressure, so as to obtain 16.4 g of a yellow oil product, 2-bromo-1-(2-hydroxy-5-(2-hydroxyethyl)-4-methoxyphenyl)-1-ethanone.

Also, 2-bromo-1-(2-hydroxy-4-(2-hydroxyethyl)-5-methoxyphenyl)-1-ethanone was obtained in the same above manner.

IR (neat) cm$^{-1}$: 3376, 2941, 1644, 1496, 1243, 1034, 757, 690

NMR (CDCl$_3$) δppm: 1.5-1.8 (1H, m), 2.91 (2H, t, J=7 Hz), 3.8-4.1 (2H, m), 3.85 (3H, s), 4.40 (2H, s), 6.89 (1H, s), 7.07 (1H, s), 11.51 (1H, s)

(6) 2-(6-methoxy-1-benzofuran-5-yl)-1-ethanol 16.4 g of the above 2-bromo-1-(2-hydroxy-5-(2-hydroxyethyl)-4-methoxyphenyl)-1-ethanone was dissolved in 70 ml of methanol. Thereafter, 17.3 g of sodium acetate was added to the obtained solution, and the obtained mixture was then heated to reflux for 5 minutes. After cooling, water and ethyl acetate were added to the reaction mixture, and an organic layer was separated. The organic layer was successively washed with water and a saturated saline solution, and then dried over anhydrous magnesium sulfate. The solvent was then distilled away under a reduced pressure. The residue was dissolved in 150 ml of methanol. Thereafter, 6.30 g of sodium borohydride was dividedly added to the obtained solution, and the obtained mixture was stirred at a room temperature for 1 hour. Subsequently, 6 mol/l hydrochloric acid was added to the reaction solution, so that the pH thereof was adjusted to pH 1. The obtained solution was further stirred at a room temperature for 1 hour. This reaction mixture was concentrated under a reduced pressure. Thereafter, water and ethyl acetate were added thereto, and an organic layer was separated. The organic layer was successively washed with water and a saturated saline solution, and then dried over anhydrous magnesium sulfate. The solvent was then distilled away under a reduced pressure. The residue was purified by column chromatography (eluent: hexane:ethyl acetate=4:1), so as to obtain 1.48 g of a light yellow crystal, 2-(6-methoxy-1-benzofuran-5-yl)-1-ethanol.

NMR (CDCl$_3$) δppm: 1.79 (1H, brs), 2.97 (2H, t, J=7 Hz), 3.84 (2H, t, J=7 Hz), 3.86 (3H, s), 6.66 (1H, d, J=3 Hz), 7.03 (1H, s), 7.35 (1H, s), 7.51 (1H, d, J=3 Hz)

Also, 2-(5-methoxy-1-benzofuran-6-yl)-1-ethanol was obtained in the same above manner.

NMR (CDCl$_3$) δppm: 2.04 (1H, brs), 2.98 (2H, t, J=6 Hz), 3.86 (2H, t, J=6 Hz), 3.86 (3H, s), 6.68 (1H, d, J=2 Hz), 7.02 (1H, s), 7.31 (1H, s), 7.55 (1H, d, J=2 Hz)

(7) Production of 2-(2-(6-methoxy-1-benzofuran-5-yl)ethoxy)acetic acid 1.75 g of 2-(6-methoxy-1-benzofuran-5-yl)-1-ethanol was dissolved in a mixed solution consisting of 7.0 ml of tert-butanol and 1.75 ml of N,N-dimethylformamide. Thereafter, 2.2 g of 1-chloroacetylpiperidine and 1.54 g of potassium tert-butoxide were added to the obtained solution, while cooling on ice. The obtained mixture was stirred at the same temperature for 30 minutes and then at a room temperature for 2 hours. Thereafter, water and ethyl acetate were added to the reaction mixture. The pH of the obtained mixture was adjusted to pH 1 by addition of 6 mol/l hydrochloric acid, and an organic layer was separated. The organic layer was successively washed with water and a saturated saline solution, and then dried over anhydrous magnesium sulfate. The solvent was then distilled away under a reduced pressure. The residue was dissolved in 10.5 ml of a 90% aqueous ethanol solution. Thereafter, 0.91 g of sodium hydroxide was added thereto, and the obtained mixture was then heated to reflux for 3 hours. After cooling, water and ethyl acetate were added to the reaction mixture. The pH of the obtained mixture was adjusted to pH 1 by addition of 6 mol/l hydrochloric acid, and an organic layer was separated. The organic layer was successively washed with water and a saturated saline solution, and then dried over anhydrous magnesium sulfate. The solvent was then distilled away under a reduced pressure. Thereafter, diisopropyl ether was added to the residue, and precipitated crystals were then collected by filtration. The obtained crystals were washed with diisopropyl ether and then dried, so as to obtain 1.42 g of a yellow crystal, 2-(2-(6-methoxy-1-benzofuran-5-yl)ethoxy)acetic acid.

IR (neat) cm$^{-1}$: 2939, 1734, 1426, 1252, 1200, 1148, 1094, 1022, 771

NMR (DMSO-d$_6$) δppm: 2.88 (2H, t, J=7 Hz), 3.64 (2H, t, J=7 Hz), 3.82 (3H, s), 4.01 (2H, s), 6.81 (1H, d, J=2 Hz), 7.22 (1H, s), 7.44 (1H, s), 7.82 (1H, d, J=2 Hz)

Also, 2-(2-(5-methoxy-1-benzofuran-6-yl)ethoxy)acetic acid was obtained in the same above manner.

NMR (DMSO-d$_6$) δppm: 2.90 (2H, t, J=7 Hz), 3.66 (2H, t, J=7 Hz), 3.82 (3H, s), 4.02 (2H, s), 6.86 (1H, d, J=2 Hz), 7.15 (1H, s), 7.46 (1H, s), 7.88 (1H, d, J=2 Hz)

Reference Example 7

Production of 3-(2-(1-benzothiophene-5-yl)ethoxy)propionic acid (1) 29 mg of potassium hydroxide, 83 mg of tetra-n-butyl ammonium bromide, and 5.67 ml of tert-butyl acrylate were added to 4.60 g of 2-(1-benzothiophene-5-yl)-1-ethanol, and the obtained mixture was then stirred at 45° C. to 50° C. for 2 hours. After cooling, water and toluene were added to the reaction mixture. The pH of the mixture was adjusted to pH 1 by addition of 6 mol/l hydrochloric acid, and an organic layer was separated. The organic layer was washed with water and then dried over anhydrous magnesium sulfate. The solvent was then distilled away under a reduced pressure. The residue was purified by column chromatography (eluent; hexane:ethyl acetate=5:1), so as to obtain 7.70 g of an achromatic oil product, 3-(2-(1-benzothiophene-5-yl)ethoxy)propionic acid tert-butyl.

IR (neat) cm$^{-1}$: 2978, 2867, 1729, 1368, 1159, 1112, 702

NMR (CDCl$_3$) δppm: 1.43 (9H, s), 2.49 (2H, t, J=6 Hz), 2.99 (2H, t, J=7 Hz), 3.70 (2H, t, J=6 Hz), 3.70 (2H, t, J=7 Hz), 7.21 (1H, dd, J=2, 8 Hz), 7.27 (1H, dd, J=1, Hz), 7.41 (1H, d, J=5 Hz), 7.6-7.7 (1H, m), 7.78 (1H, d, J=8 Hz)

(2) 7.60 g of 3-(2-(1-benzothiophene-5-yl)ethoxy)propionic acid tert-butyl was dissolved in 22.8 ml of toluene. Thereafter, 94 mg of p-toluenesulfonic acid monohydrate was added thereto, and the obtained mixture was heated to reflux for 6 hours. After cooling, water and ethyl acetate were added to the reaction mixture, and an organic layer was separated. The organic layer was dried over anhydrous magnesium sulfate. The solvent was then distilled away under a reduced pressure. The residue was crystallized from a toluene-cyclohexane mixed solution (1:4; 23 ml), so as to obtain 5.30 g of a light red crystal, 3-(2-(1-benzothiophene-5-yl)ethoxy)propionic acid.

IR (KBr) cm$^{-1}$: 2860, 1719, 1273, 1128, 706

NMR (CDCl$_3$) δppm: 2.63 (2H, t, J=6 Hz), 3.00 (2H, t, J=7 Hz), 3.73 (2H, t, J=7 Hz), 3.74 (2H, t, J=6 Hz), 7.20 (1H, dd, J=1, 8 Hz), 7.28 (1H, dd, J=1, 5 Hz), 7.41 (1H, d, J=5 Hz), 7.6-7.7 (1H, m), 7.79 (1H, d, J=8 Hz)

Formulation Example 1

Component (i): A mixture consisting of 50 mg of 1-(3-(2-(1-benzothiophene-5-yl)ethoxy)propyl)-3-azetidinol maleate (hereinafter referred to as compound A), 20 mg of lactose, 25 mg of corn starch, and 40 mg of Avicel PH101 (manufactured by Asahi Kasei Corp.)

Component (ii): 10 mg of Kollidon CL (manufactured by BASF), 10 mg of Avicel PH302 (manufactured by Asahi Kasei Corp.), 18 mg of light anhydrous silicic acid, and 2 mg of magnesium stearate Component (i) was kneaded with a 5% polyvinylpyrrolidone K30 aqueous solution and then dried at 60° C. Thereafter, component (ii) was mixed with the above mixture. The obtained mixture was formulated into a round tablet with a weight of 175 mg and a diameter of 8 mm, thereby obtaining a tablet containing 50 mg of compound A.

Formulation Example 2

Component (i): A mixture consisting of 50 mg of compound A, 20 mg of lactose, and 53 mg of corn starch Component (ii): 7 mg of Kollidon CL (manufactured by BASF), 18 mg of Avicel PH302 (manufactured by Asahi Kasei Corp.), and 2 mg of magnesium stearate Component (i) was kneaded with a 50 polyvinylpyrrolidone K30 aqueous solution and then dried at 60° C. Thereafter, component (ii) was mixed with the above mixture. 150 mg of the obtained mixture was filled in a size-3 gelatin capsule, so as to obtain a capsule agent.

Formulation Example 3

1 g of compound A was weighed. 80 ml of a parenteral solution (Japanese Pharmacopoeia) was added to the obtained compound for dissolution. A 0.1 mol/l aqueous sodium dihydrogen phosphate solution and a 0.1 mol/l aqueous sodium phosphate solution were added to the above solution, so that the pH of the mixture was adjusted to pH 7.5. Thereafter, an appropriate amount of sodium chloride was added as an isotonizing agent to the obtained solution. A parenteral solution was further added thereto, so as to obtain exactly 100 ml of a solution. This solution was filtrated through a membrane filter (pore size: 0.2 μm) under aseptic environment, so as to obtain a solution used as eyedrop. The obtained solution was filled in a polyethylene eyedrop bottle (volume: 5 ml) under aseptic environment, and the bottle was then hermetically closed, so as to obtain an eyedrop agent containing 1 w/v % compound A.

Formulation 4

1 g of compound A was weighed. 80 ml of a parenteral solution (Japanese Pharmacopoeia) was added to the obtained compound for dissolution. A 0.1 mol/l aqueous potassium dihydrogen phosphate solution and a 0.1 mol/l aqueous sodium dihydrogen phosphate solution were added to the above solution, so that the pH of the mixture was adjusted to pH 7.5. Thereafter, an appropriate amount of sodium chloride was added as an isotonizing agent to the obtained solution. A parenteral solution was further added thereto, so as to obtain exactly 100 ml of a solution. This solution was filtrated through a membrane filter (pore size: 0.2 μm) under aseptic environment, so as to obtain a solution used as eyedrop. The obtained solution was filled in a polyethylene eyedrop bottle (volume: 5 ml) under aseptic environment, and the bottle was then hermetically closed, so as to obtain an eyedrop agent containing 1 w/v % compound A.

INDUSTRIAL APPLICABILITY

The alkyl ether derivative represented by the general formula [1] or a salt thereof shows the effect of protecting retinal nerve cells, and thus it is useful as a preventive and/or remedy for retinal nerve diseases such as glaucoma, diabetic retinopathy, retinal artery obstruction, retinal venous obstruction, macular degeneration, and retinopathy of prematurity.

The invention claimed is:
1. A method for treating macular degeneration comprising administering to a subject in need thereof an alkyl ether derivative, wherein the alkyl ether derivative is 1-(3-(2-(1-benzothiophen-5-yl)ethoxy)propyl)-3-azetidinol or its pharmacologically acceptable salt.
2. The method according to claim 1, wherein the alkyl ether derivative is 1-(3-(2-(1-benzothiophen-5-yl)ethoxy)propyl)-3-azetidinol maleate.

* * * * *